United States Patent
Koronyo et al.

(10) Patent No.: US 11,058,720 B2
(45) Date of Patent: Jul. 13, 2021

(54) METHODS OF TREATING OR PREVENTING ALZHEIMER'S DISEASE AND ASSOCIATED CONDITIONS

(71) Applicant: CEDARS-SINAI MEDICAL CENTER, Los Angeles, CA (US)

(72) Inventors: Maya Koronyo, Los Angeles, CA (US); Altanchimeg Rentsendorj, West Hollywood, CA (US); Yosef Koronyo, Los Angeles, CA (US); Keith Black, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 212 days.

(21) Appl. No.: 16/303,053

(22) PCT Filed: May 22, 2017

(86) PCT No.: PCT/US2017/033875
§ 371 (c)(1),
(2) Date: Nov. 19, 2018

(87) PCT Pub. No.: WO2017/201539
PCT Pub. Date: Nov. 23, 2017

(65) Prior Publication Data
US 2019/0290687 A1 Sep. 26, 2019

Related U.S. Application Data

(60) Provisional application No. 62/339,681, filed on May 20, 2016.

(51) Int. Cl.
| | |
|---|---|
| *A61K 35/15* | (2015.01) |
| *A61P 25/28* | (2006.01) |
| *A61K 31/7088* | (2006.01) |
| *A61K 38/02* | (2006.01) |
| *A61K 38/18* | (2006.01) |
| *A61K 38/19* | (2006.01) |

(52) U.S. Cl.
CPC .......... *A61K 35/15* (2013.01); *A61K 31/7088* (2013.01); *A61K 38/02* (2013.01); *A61K 38/18* (2013.01); *A61K 38/19* (2013.01); *A61P 25/28* (2018.01)

(58) Field of Classification Search
CPC .... A61K 35/15; A61K 31/7088; A61K 38/02; A61K 38/18; A61K 38/19; A61K 45/06; A61K 38/07; A61P 25/28
See application file for complete search history.

(56) References Cited

U.S. PATENT DOCUMENTS

| | | | |
|---|---|---|---|
| 4,882,165 A | 11/1989 | Hunt et al. | |
| 4,946,788 A | 8/1990 | Delespesse et al. | |
| 5,585,089 A | 12/1996 | Queen et al. | |
| 8,828,404 B2 * | 9/2014 | Eisenbach-Schwartz | A61K 39/0007 424/185.1 |
| 2004/0235720 A1 | 11/2004 | Boschert et al. | |
| 2006/0057110 A1 * | 3/2006 | Eisenbach-Schwartz | A61P 25/22 424/93.1 |
| 2011/0008328 A1 | 1/2011 | Bingham et al. | |

FOREIGN PATENT DOCUMENTS

| | | |
|---|---|---|
| WO | WO-0193828 A1 | 12/2001 |
| WO | WO-2006004749 A2 | 1/2006 |
| WO | WO-2006087579 A1 | 8/2006 |
| WO | WO-2015195605 A1 | 12/2015 |
| WO | WO-2017201539 A1 | 11/2017 |

OTHER PUBLICATIONS

Begum-Haque et al. J Neuroimmunol. Jan. 15, 2013;254(1-2):117-24 (Year: 2013).*
Brown, Amanda: Osteopontin: A Key Link Between Immunity, Inflammation and the Central Nervous System. Translational Neuroscience. 3(3):288-293 (2012).
Chan et al.: Osteopontin expression in acute immune response mediates hippocampal synaptogenesis and adaptive outcome following cortical brain injury. Experimental Neurology. 261:757-771 (2014).
European Patent Application No. 17800340.6 Extended European Search Report dated Dec. 16, 2019.
Gliem et al.: Macrophage-derived osteopontin induces reactive astrocyte polarization and promotes re-establishment of the blood brain barrier after ischemic stroke. GLIA. 63(12):2198-2207 (2015).
Meller et al.: Neuroprotection by osteopontin in stroke. Journal of Cerebral Blood Flow & Metabolism. Nature Publising Group. 25(2):217-225 (2005).
Schwartz et al.: Prospects for Therapeutic Vaccination with Glatiramer Acetate for Neurodegenerative Diseases such as Alzheimer's Disease. Drug Development Research. 56(2):143-149 (2002).
Van Velthoven et al.: Osteopontin enhances endogenous repair after neonatal hypoxic-ischemic brain injury. Stroke. 42(8):2294-2301 (2011).
Bird et al.: Single-chain antigen-binding proteins; Science, 242:423-42, 1988.
Butovsky et al.: Glatiramer acetate fights against Alzheimer's disease by inducing dendritic-like microglia expressing insulin-like growth factor 1.; 103(31):11784-11789 (2006).
Cafiso, Biochem Biophys Acta 649:129 (1981).

(Continued)

*Primary Examiner* — Kimberly Ballard
*Assistant Examiner* — Stacey M MacFarlane
(74) *Attorney, Agent, or Firm* — Wilson Sonsini Goodrich & Rosati

(57) ABSTRACT

The present invention describes a method of treating, preventing, reducing the likelihood of or alleviating a symptom of Alzheimer's disease and associated conditions by increasing OPN expression. The invention further provides for a method of improving cognitive function in a subject in need thereof.

22 Claims, 33 Drawing Sheets

(56) References Cited

OTHER PUBLICATIONS

Comi et al.:Osteopontin is Increased in the Cerebrospinal Fluid of Patients with Alzheimer's Disease and Its Levels Correlate with Cognitive Decline; Journal of Alzheimer's disease: JAD 19:1143-1148 (2010).

Gabizon et al.: Liposomes as in Vivo Carriers of Adriamycin: Reduced Cardiac Uptake and Preserved Antitumor Activity in Mice_ Cancer Research 42, 4734-4739 (1982).

Greenfield, Antibodies A Laboratory Manual 2nd ed., Cold Spring Harbor Press (Cold Spring Harbor N.Y., 2013); .

Holliger and Hudson. Engineered antibody fragments and the rise of single domains. Nat. Biotechnol. 23(9):1126-36, 2005 .

Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988 .

Jankowsky et al.: Co-expression of multiple transgenes in mouse CNS: a comparison of strategies; Biomol Eng; 17(16):157-65 (2001).

Jankowsky et al.: Mutant presenilins specifically elevate the levels of the 42 residue beta-amyloid peptide in vivo: evidence for augmentation of a 42-specific gamma secretase; Hum Mol Genet; 13(2);159-70 (2004).

Juliano: Interactions of Proteins and Drugs with Liposomes, in Liposomes, Ibid.

Kohler and Milstein, Derivation of specific antibody-producing tissue culture and tumor lines by cell fusion. Eur. J. Immunol. 6: 511-519, 1976 .

Koronyo et al., Therapeutic effects of glatiramer acetate and grafted CD115+monocytes in a mouse model of Alzheimer's disease. Brain. 138(Pt 8):2399-2422 (2015).

Li et al., IFN-gamma induction of osteopontin expression in human monocytoid cells. Journal of Interferon Cytokine Research. 23(5):259-265 (2003).

Maya et al., Immunomodulatory factor induced by GA mediates macrophage clearance of pathogenic Ab forms and enhances synaptic preservation. Alzheimer's & Dementia: The Journal of the Alzheimer's Association 12(7):P361 (2016).

Ostro et al.: Use of liposomes as injectable-drug delivery systems; Am J. Hosp. Pharm. 46(8):1576-1587 (1989).

PCT/US2017/033875 International Search Report and Written Opinion dated Aug. 14, 2017.

Rentsendorj et al.: A novel role for osteopontin in macrophage-mediated amyloid-β clearance in Alzheimer's models. Brain, Behavior, and Immunity 67:1630-180 (2018) .

Riechmann et al. Reshaping human antibodies for therapy. Nature, 332.6162 (1988): 323-7.

Sambrook, et al. Molecular Cloning: A Laboratory Manual. 4th Edition, 2012.

Singleton, Dictionary of Microbiology and Molecular Biology 3.sup.rd ed., revised ed., J. Wiley & Sons (New York, N.Y. 2006); .

Smith, March's Advanced Organic Chemistry Reactions, Mechanisms and Structure 7.sup.th ed., J. Wiley & Sons (New York, N.Y. 2013); .

Szoka: Comparative properties and methods of preparation of lipid vesicles (liposomes); Ann Rev Biophys Eng 9:467 (1980).

Tomlinson I. and Holliger P. Methods for generating multivalent and bispecific antibody fragments. Methods Enzymol 326:461-479, 2000 .

Ward et al. Binding activities of a repertoire of single immunoglobulin variable domains secreted from *Escherichia coli*. Nature 334:544-54, 1989 .

Weber et al., Phosphorylation-dependent interaction of osteopontin with its receptors regulates macrophage migration and activation. Journal of Leukocyte Biology. 72:752-761 (2002).

\* cited by examiner

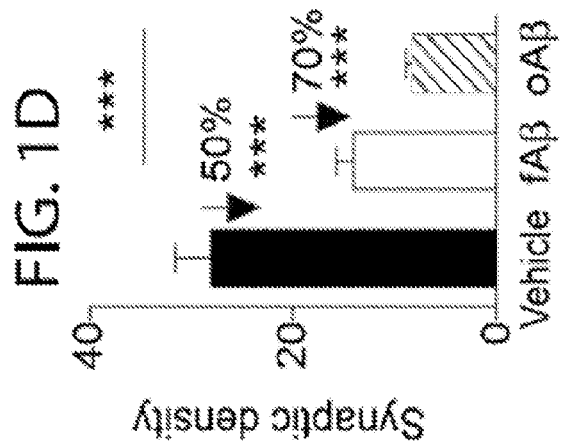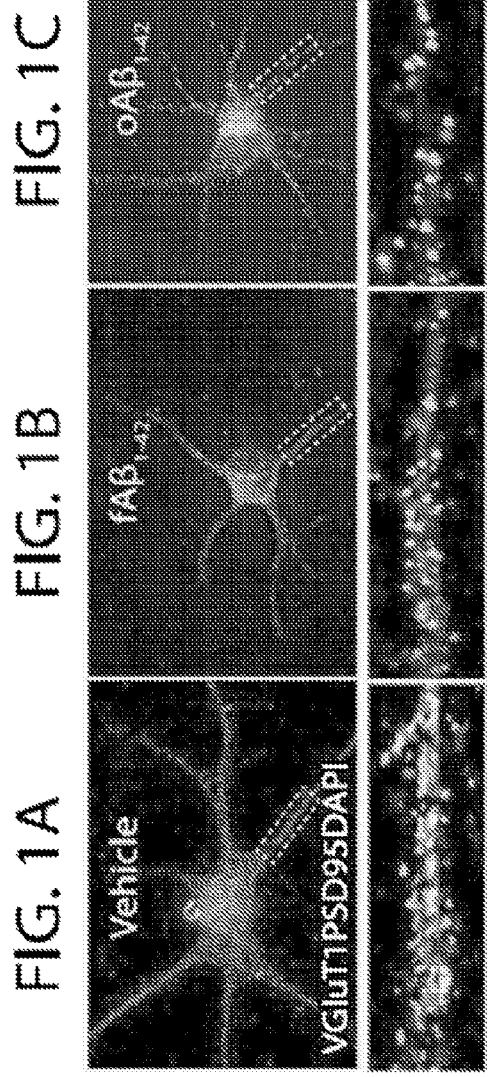

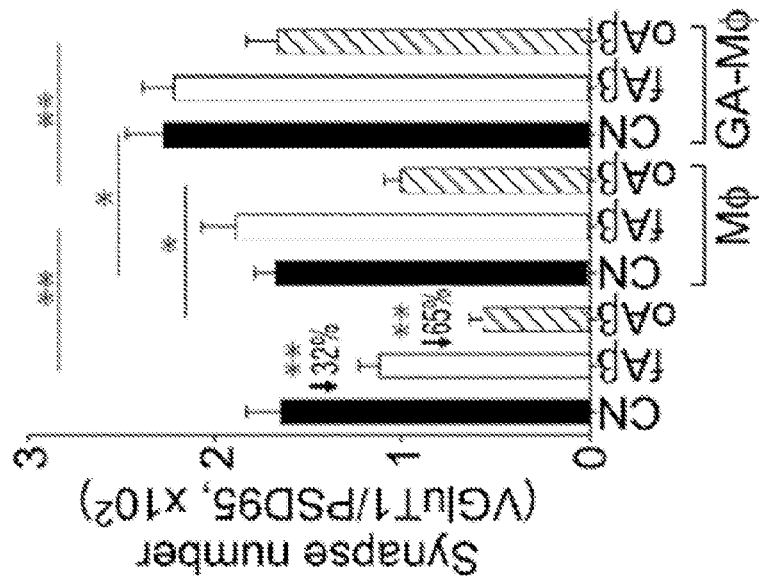
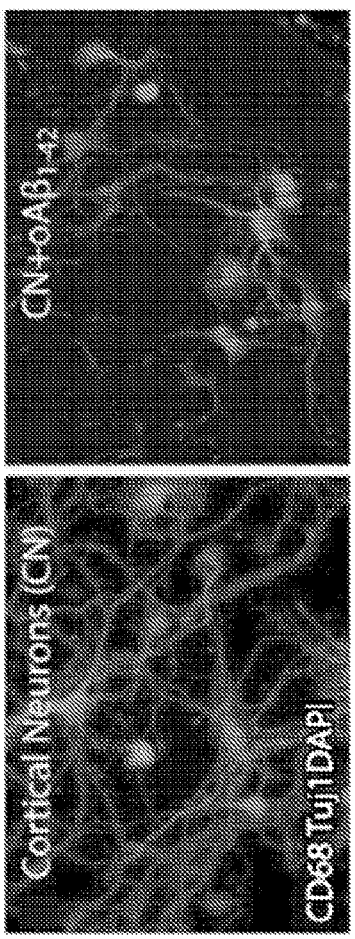
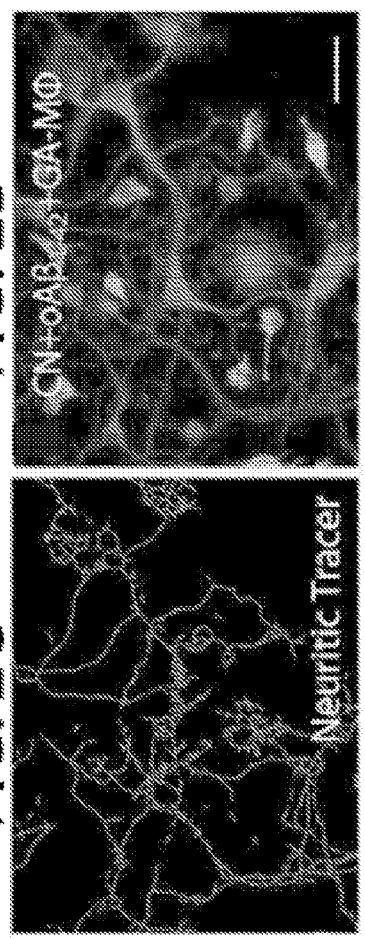

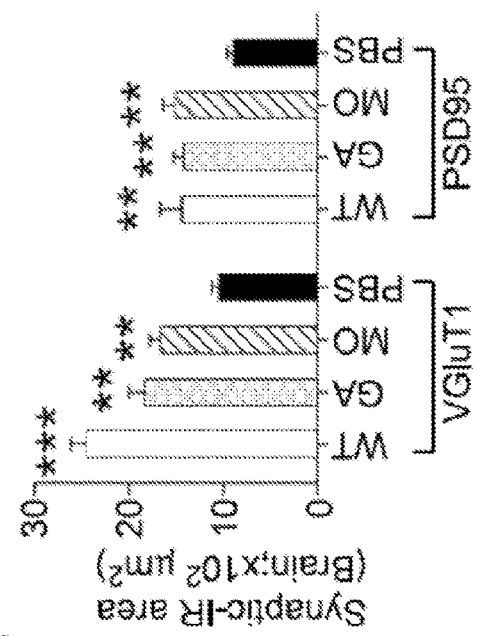
FIG. 3A
Coronal brain sections
(Bregma; -2.5, -2.65, -2.8)
FIG. 3B
FIG. 3C
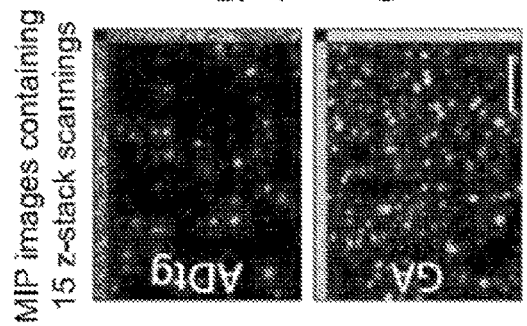
FIG. 3D
MIP images containing
15 z-stack scannings
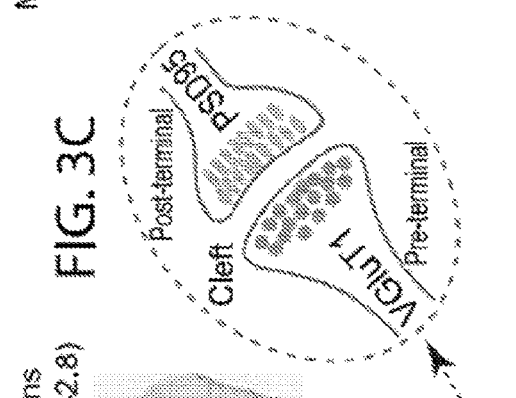
FIG. 3E
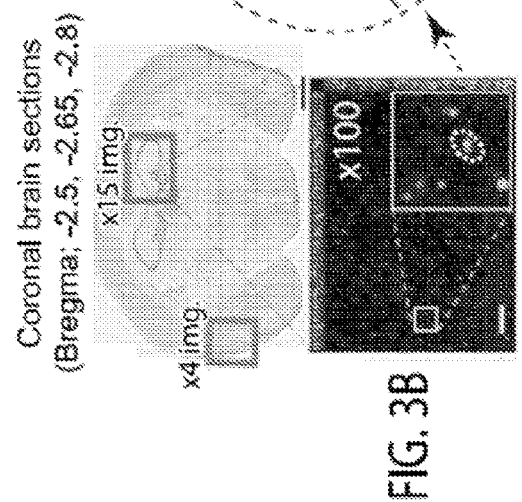

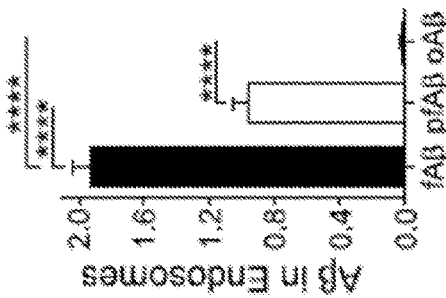
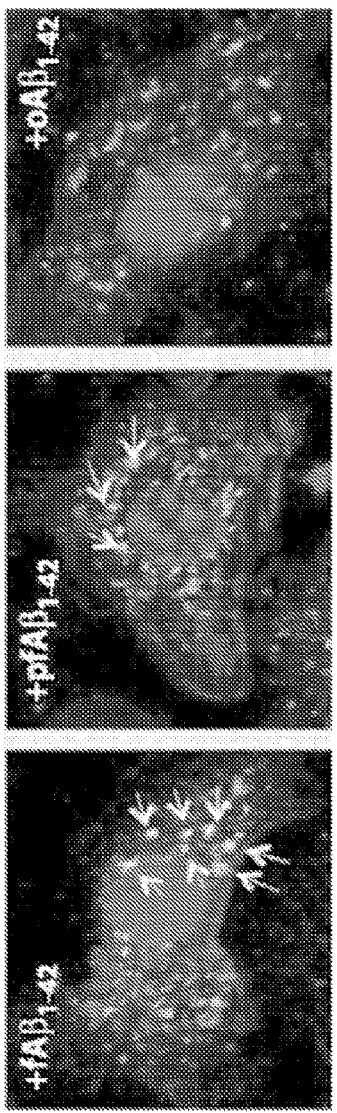
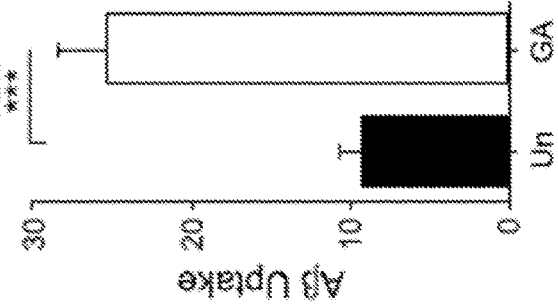
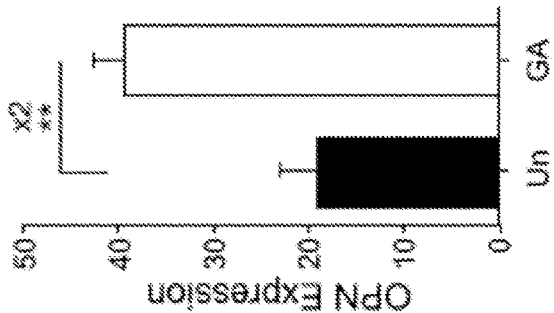
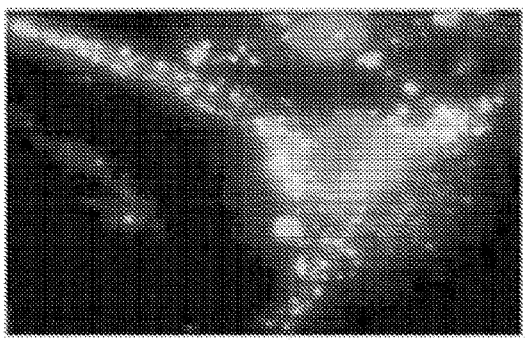
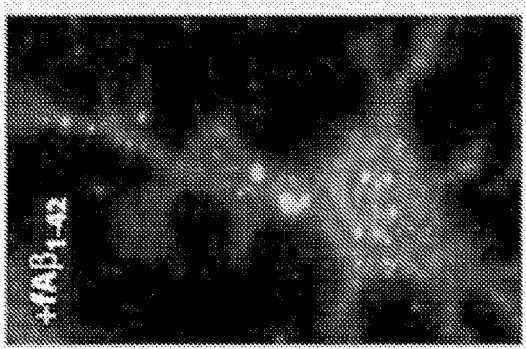

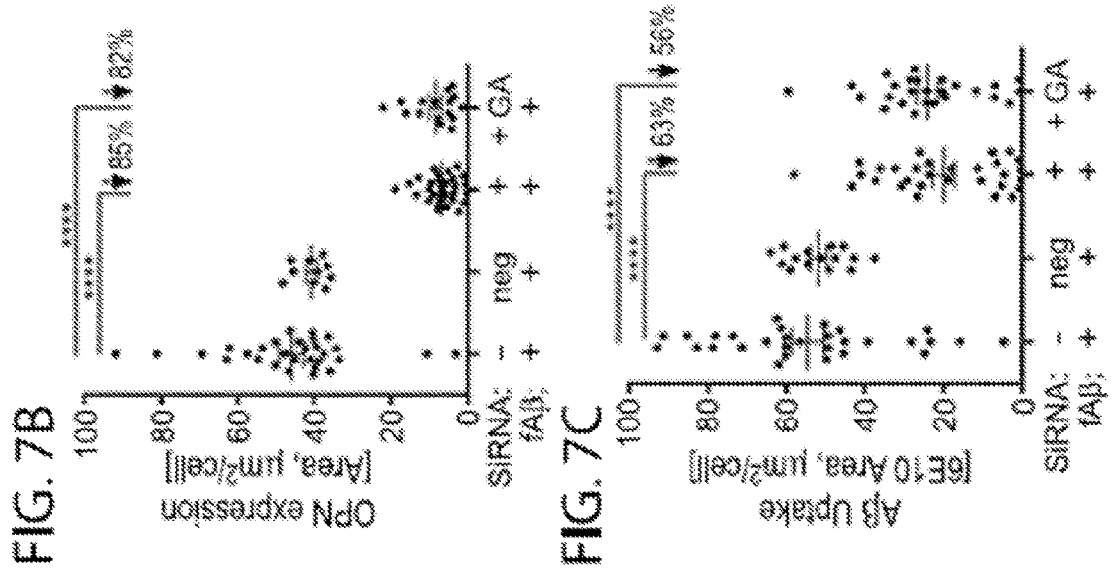
FIG. 7B
FIG. 7C
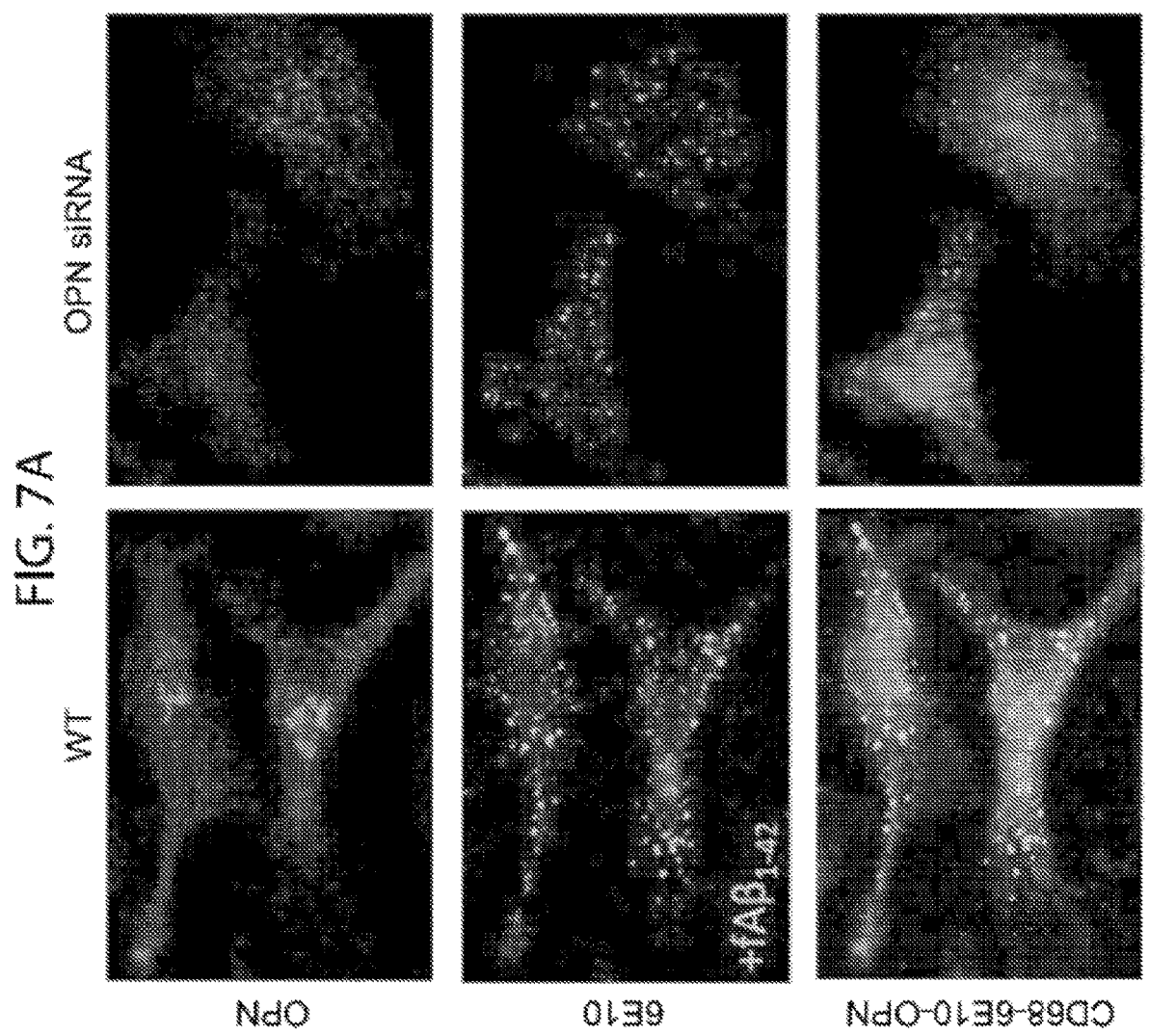
FIG. 7A

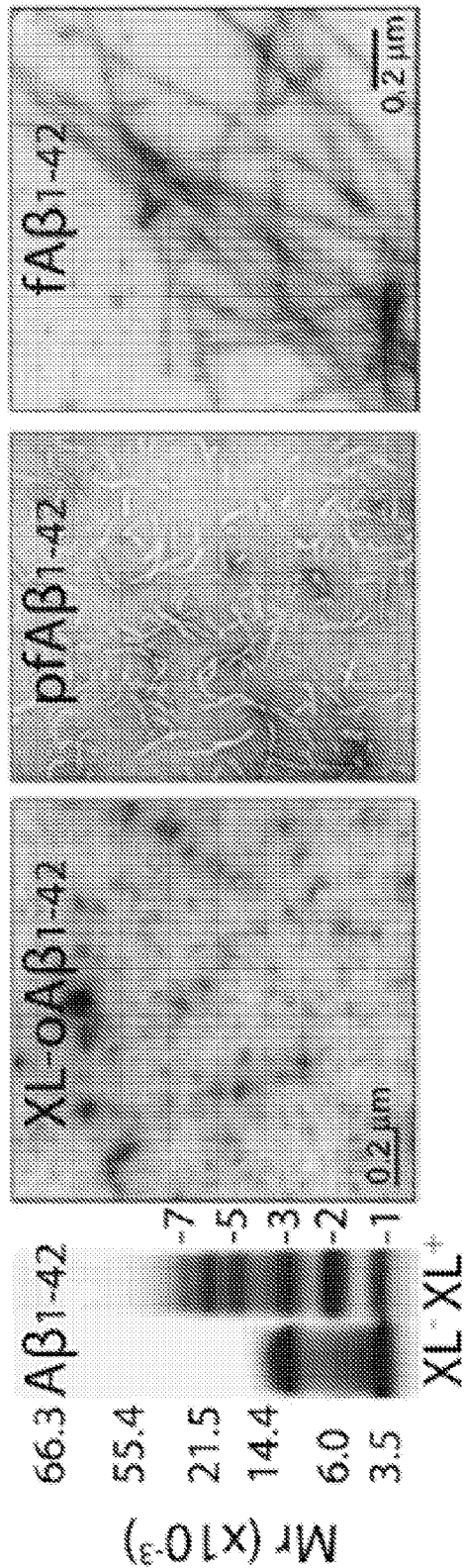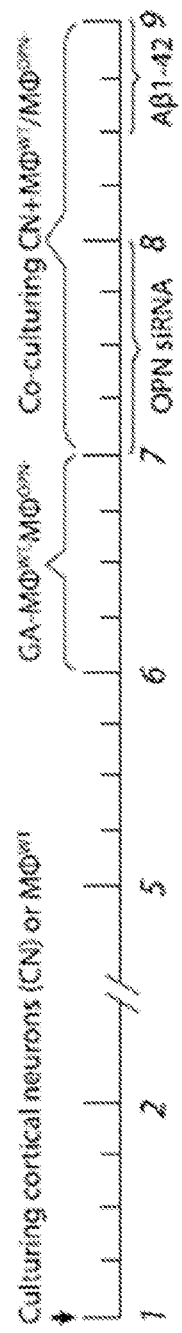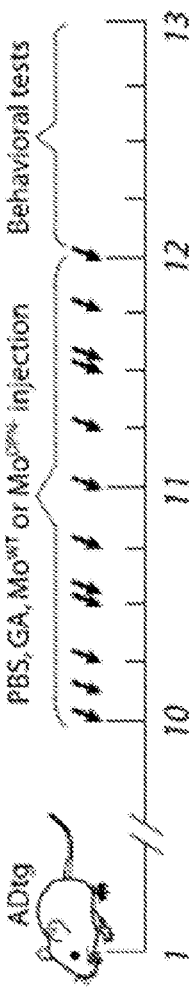

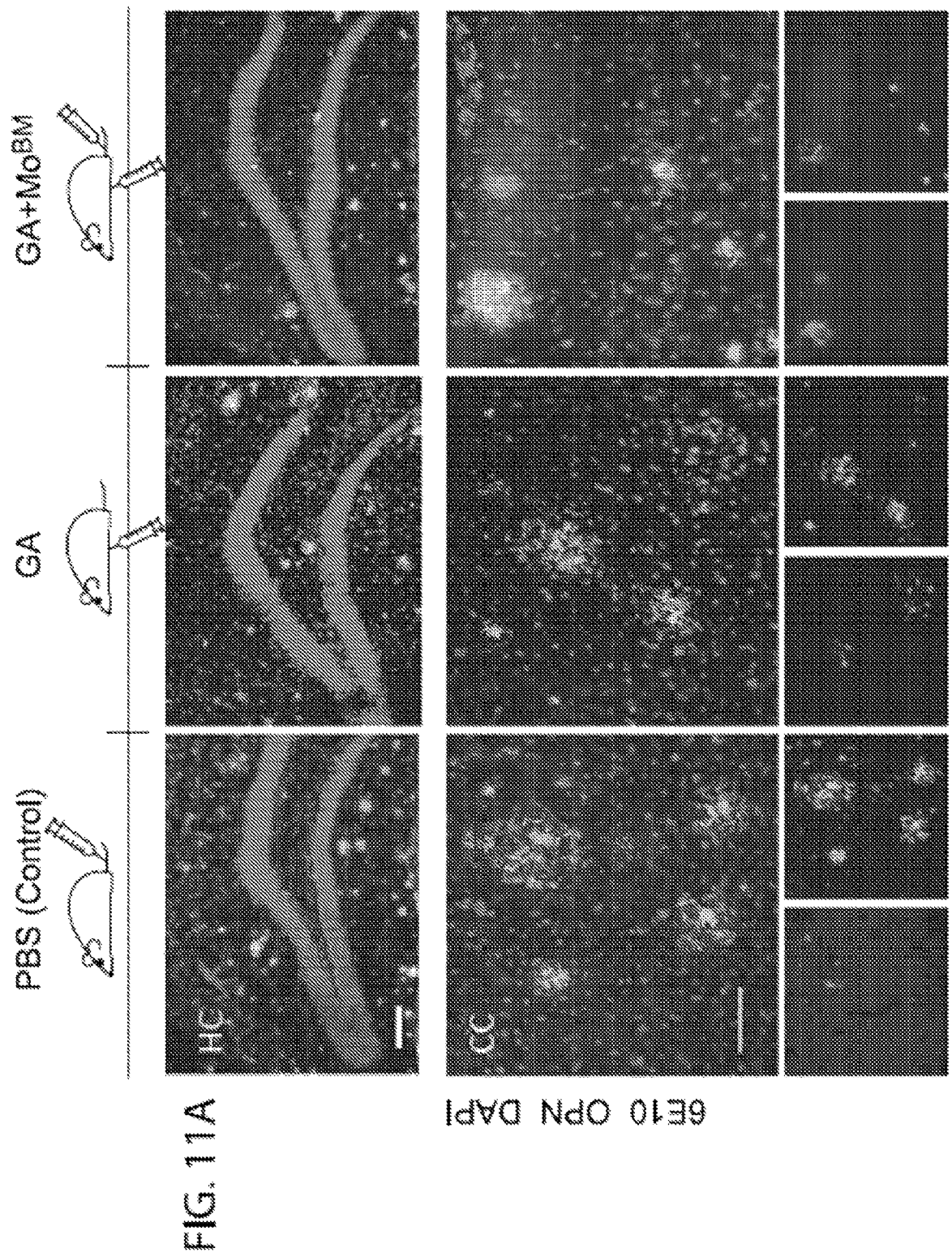

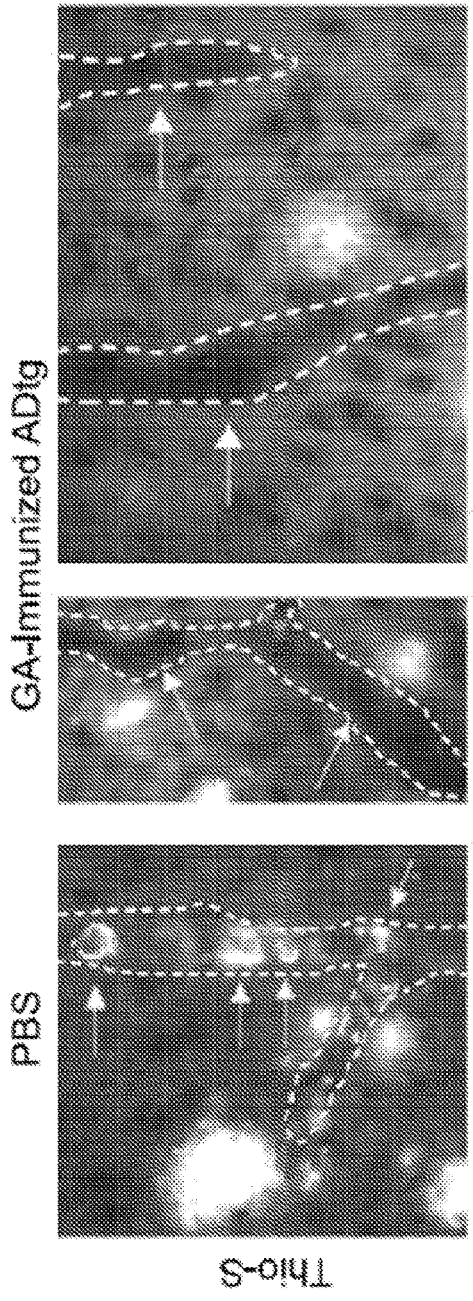
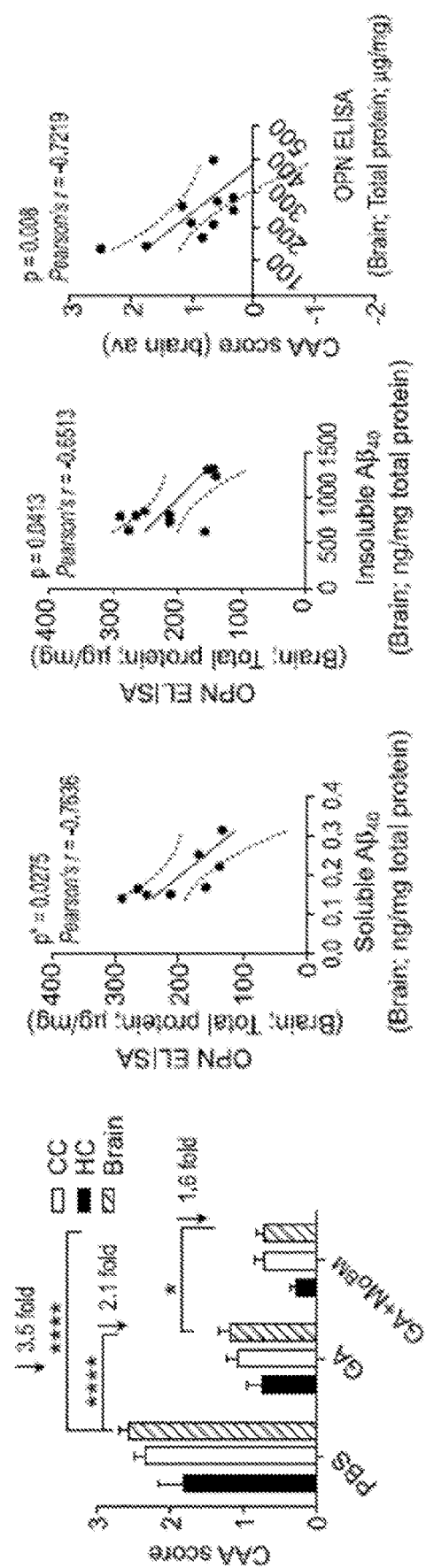
FIG. 12A
FIG. 12B

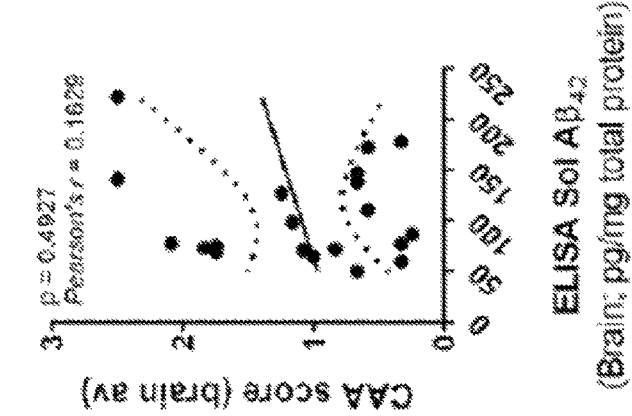
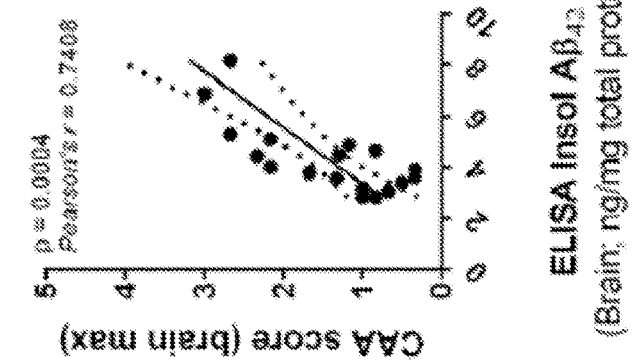
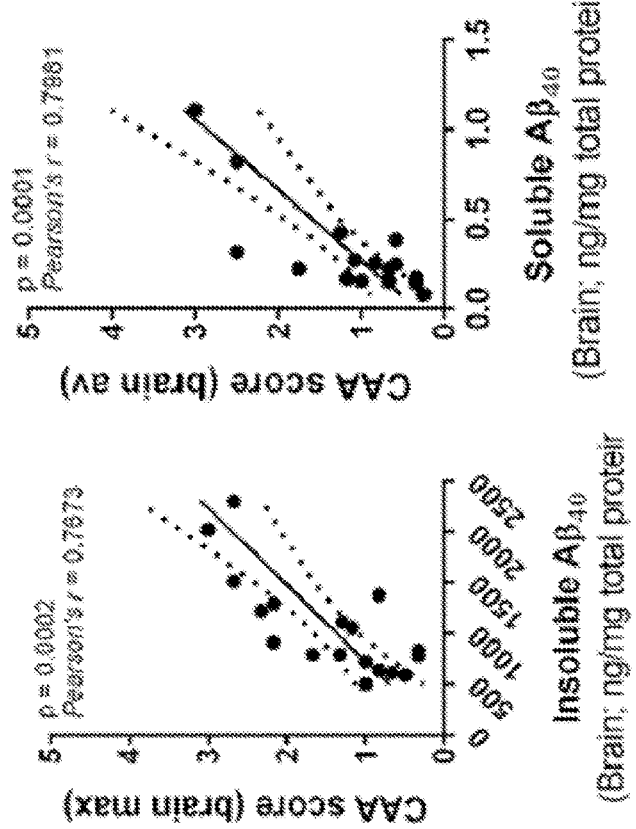
FIG. 12C    FIG. 12D    FIG. 12E    FIG. 12F

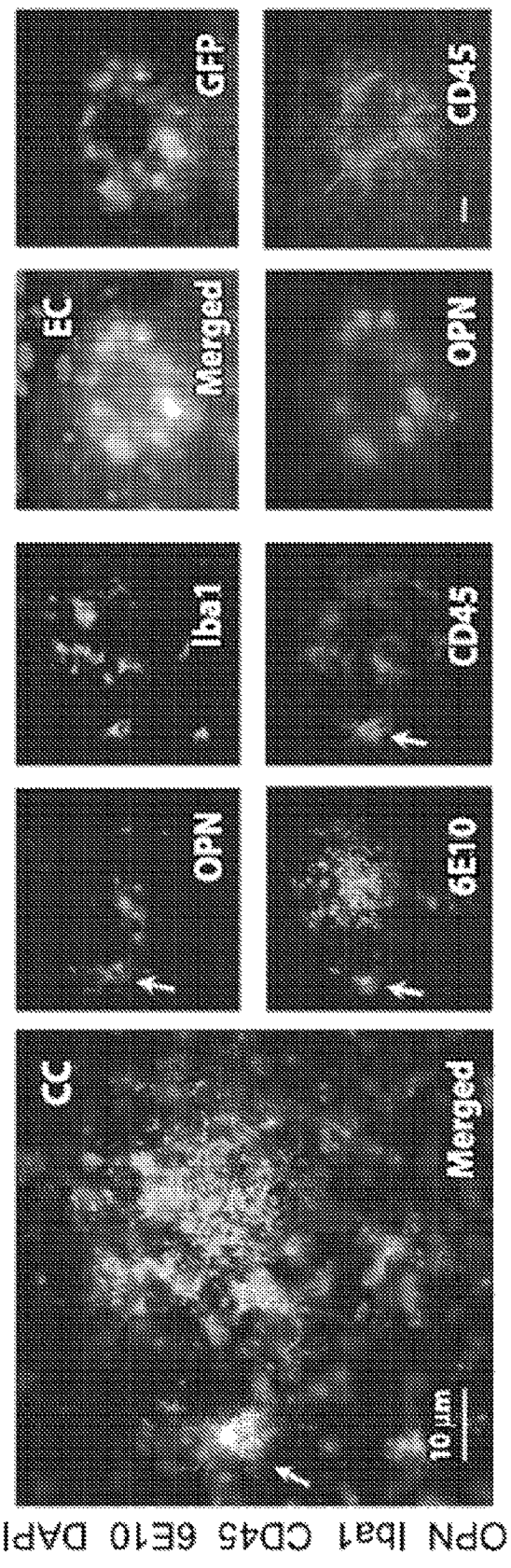
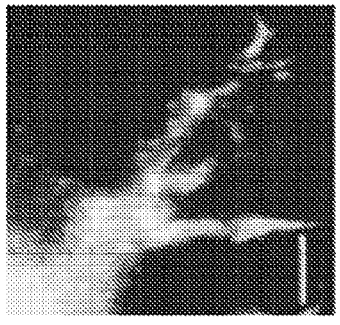
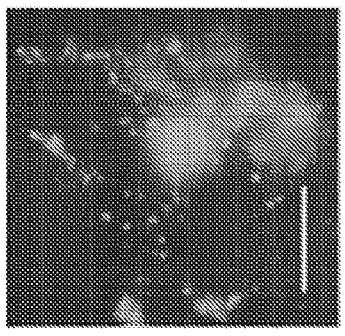
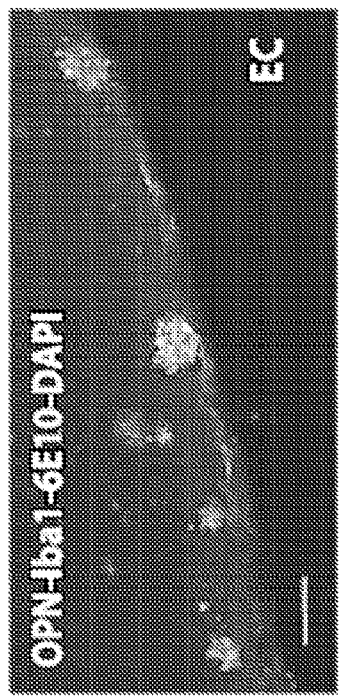
FIG. 13A  FIG. 13B  FIG. 13C  FIG. 13D  FIG. 13E

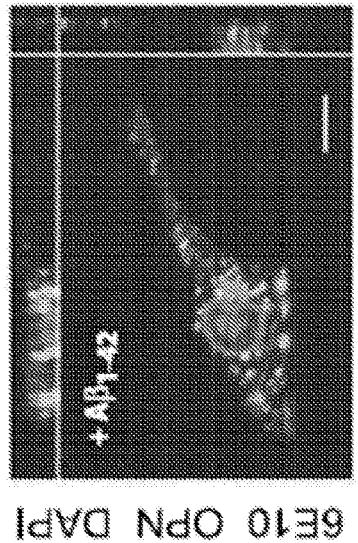
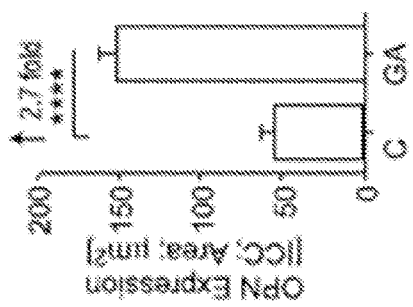
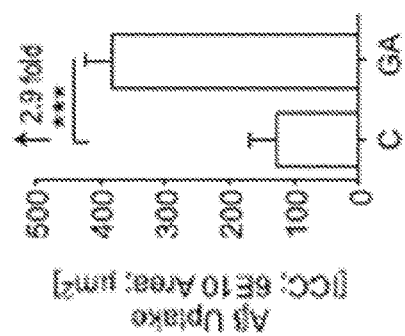
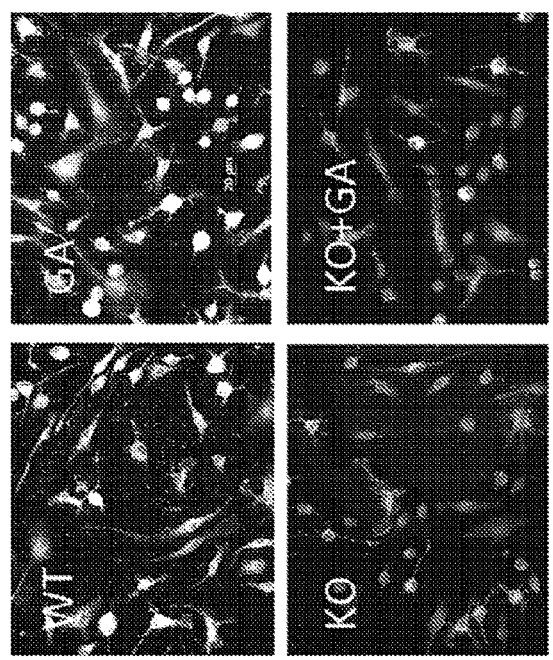
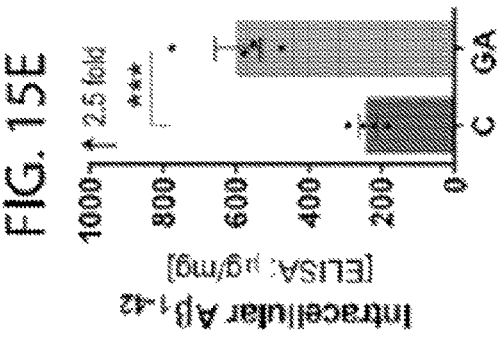
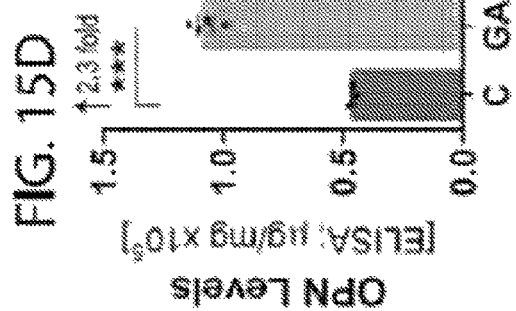

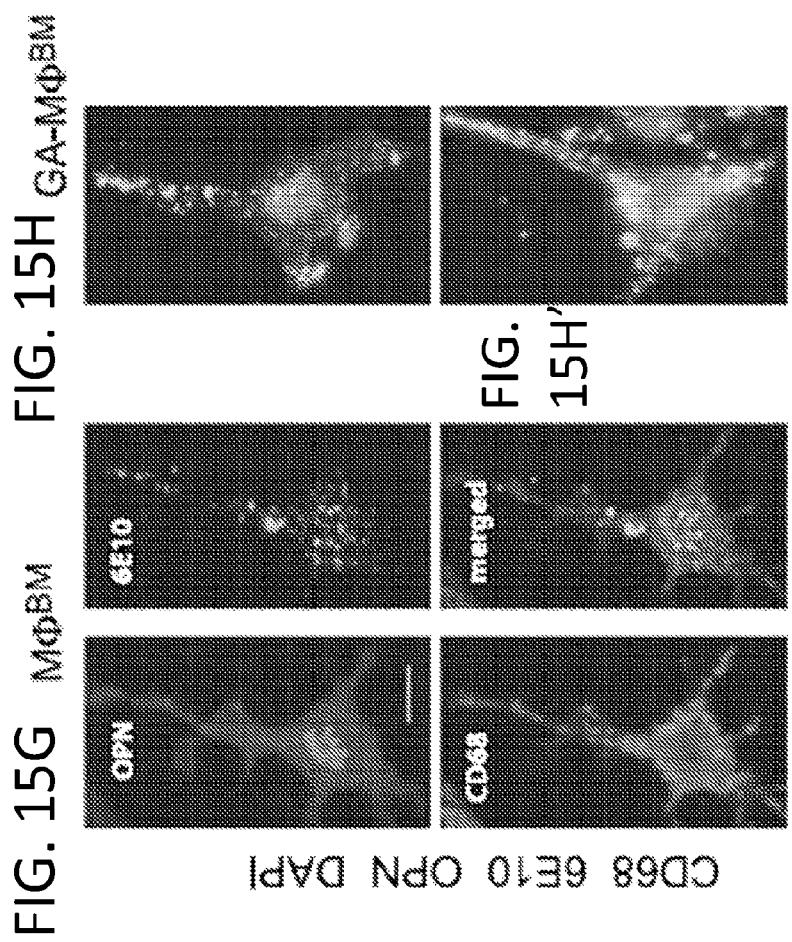
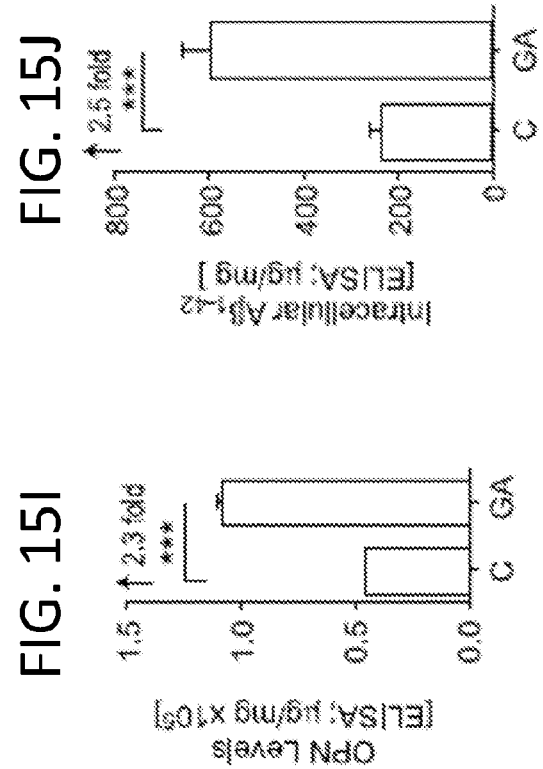
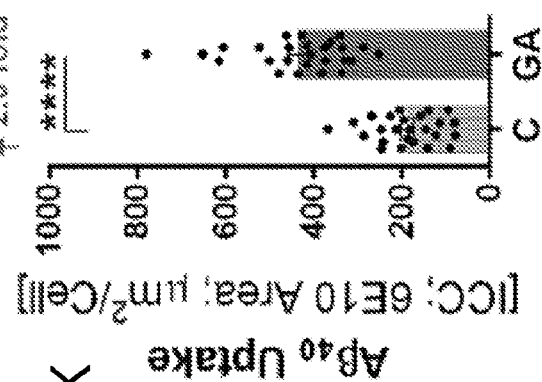
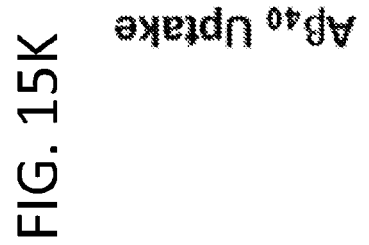

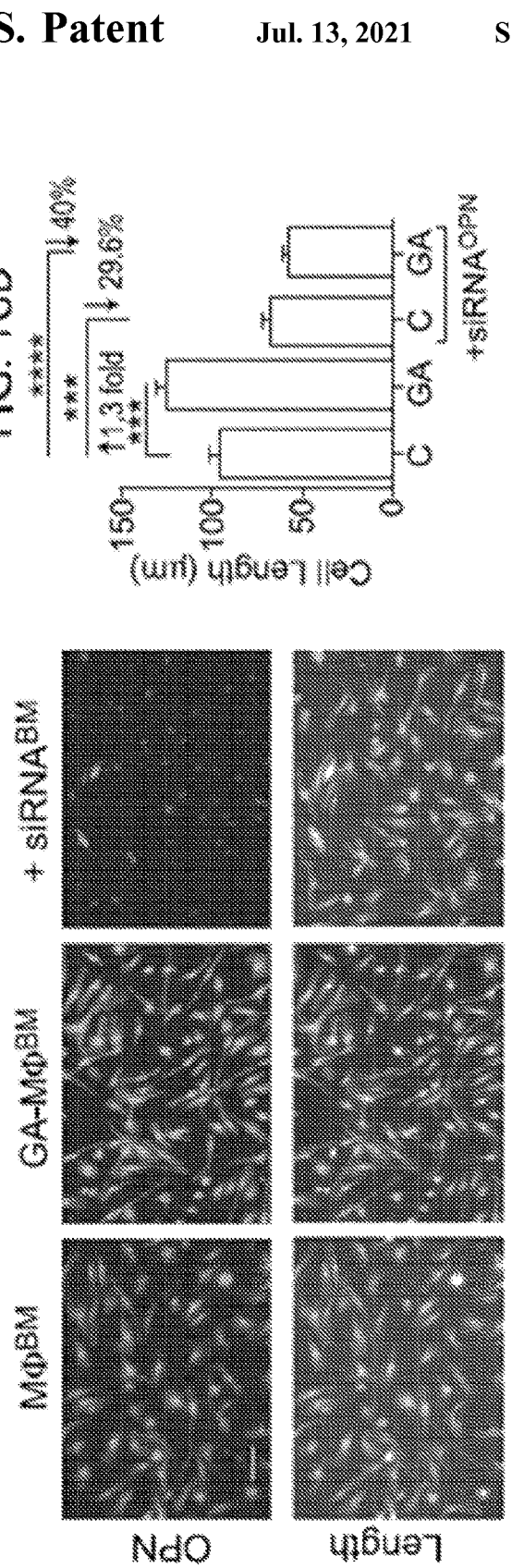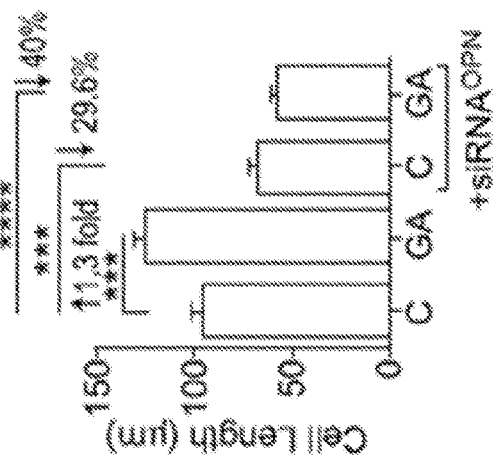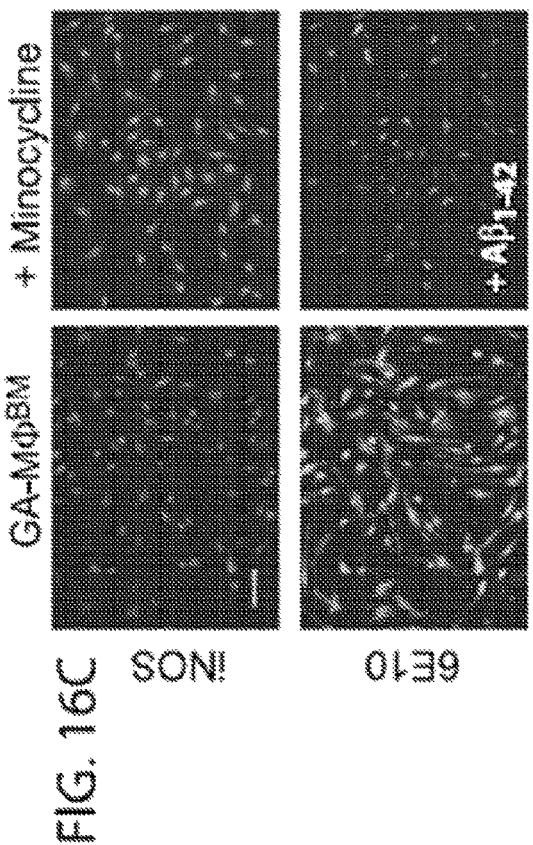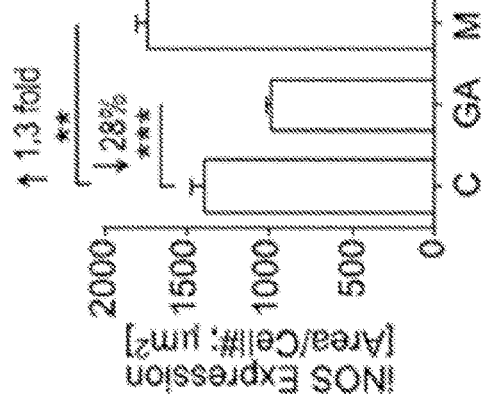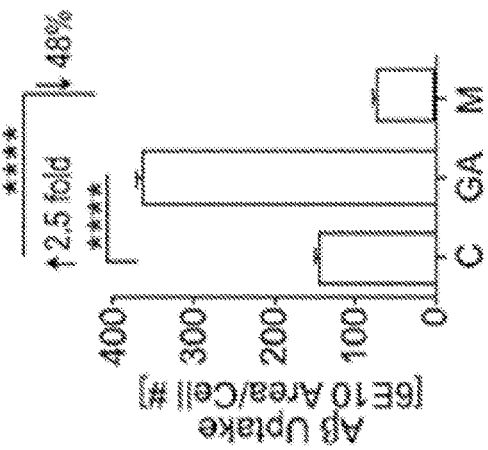

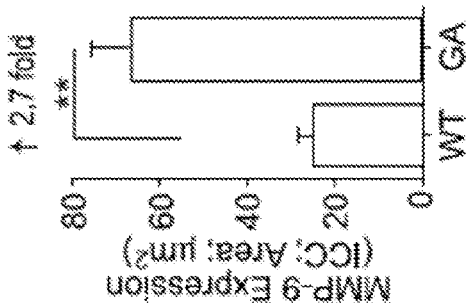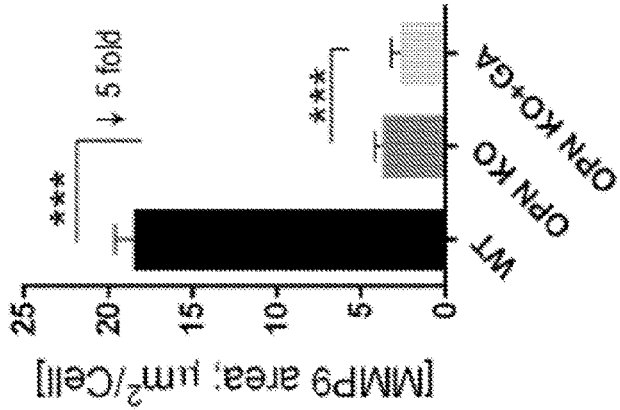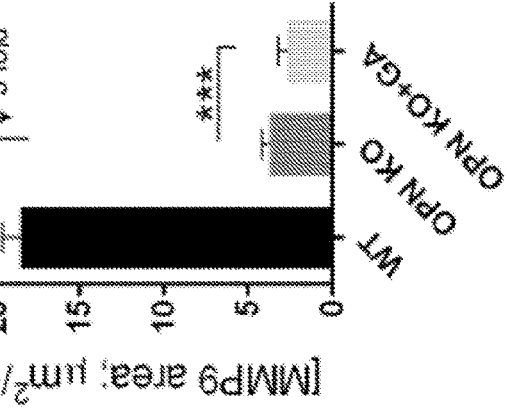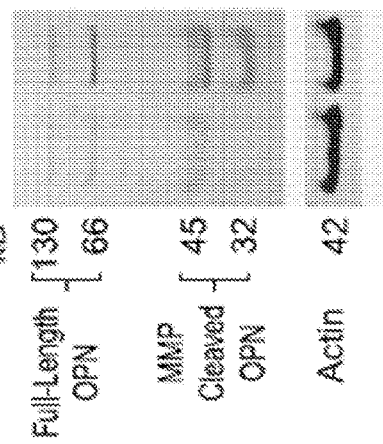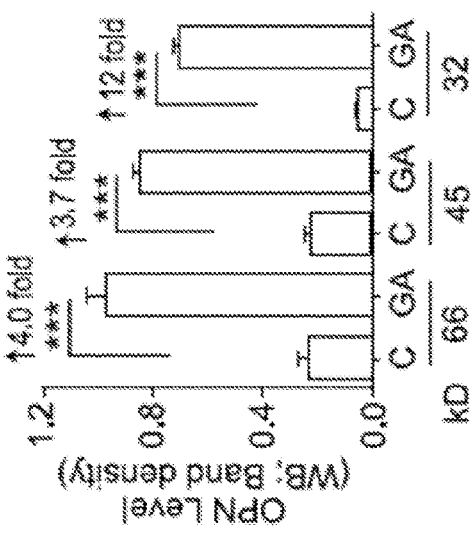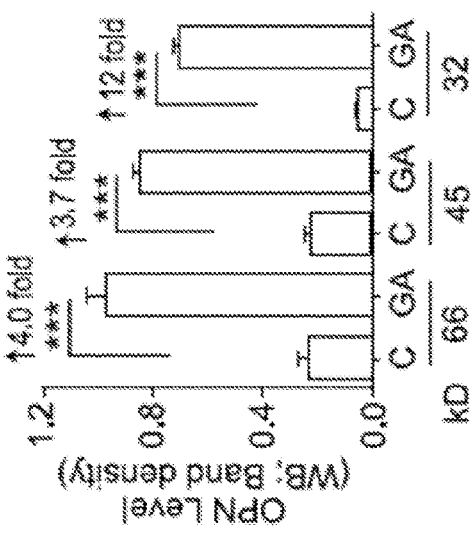

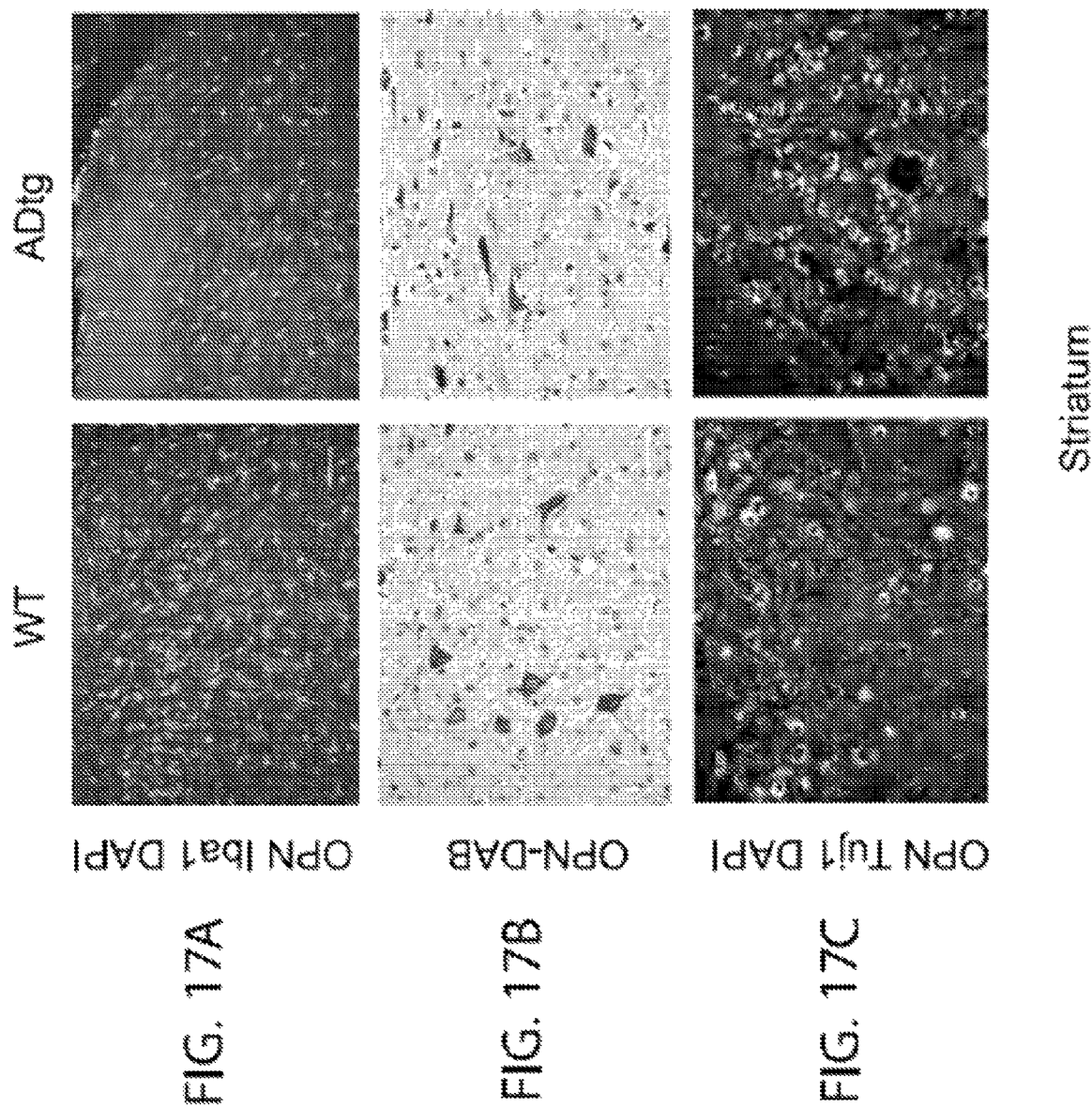

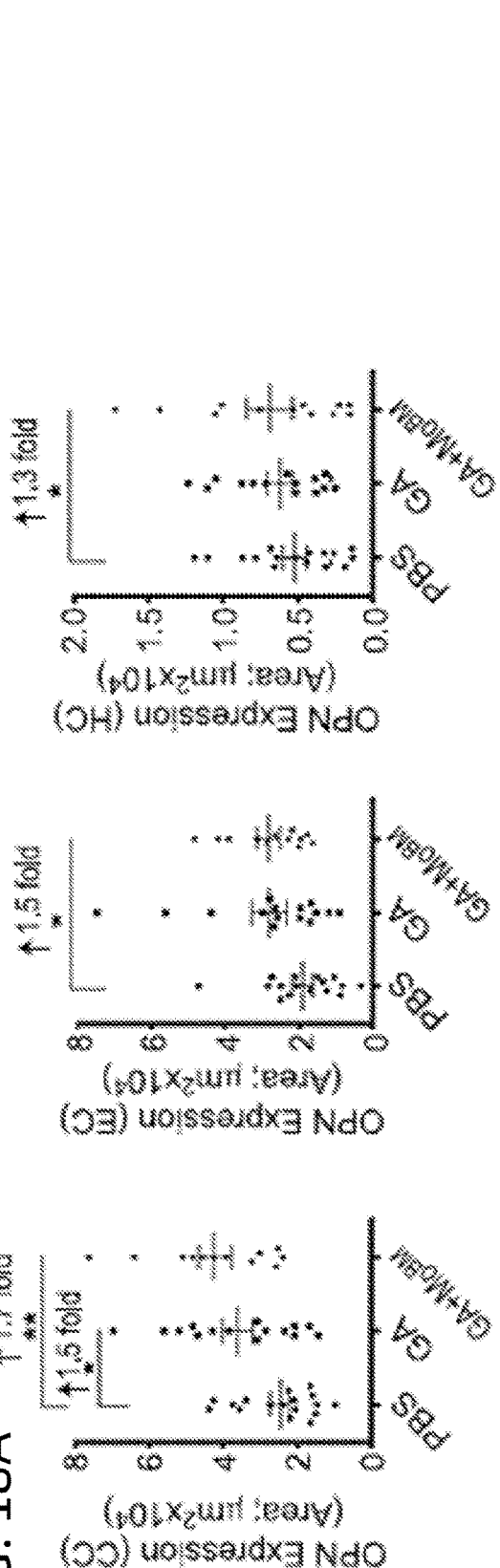
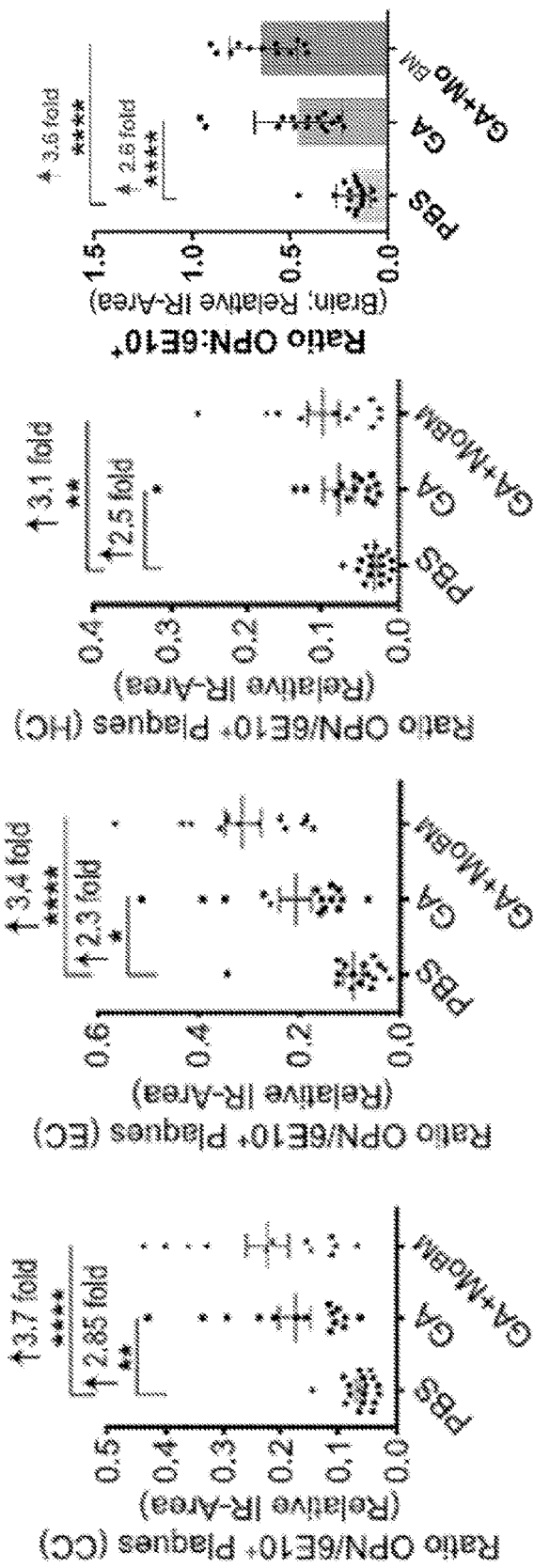
FIG. 18A
FIG. 18B

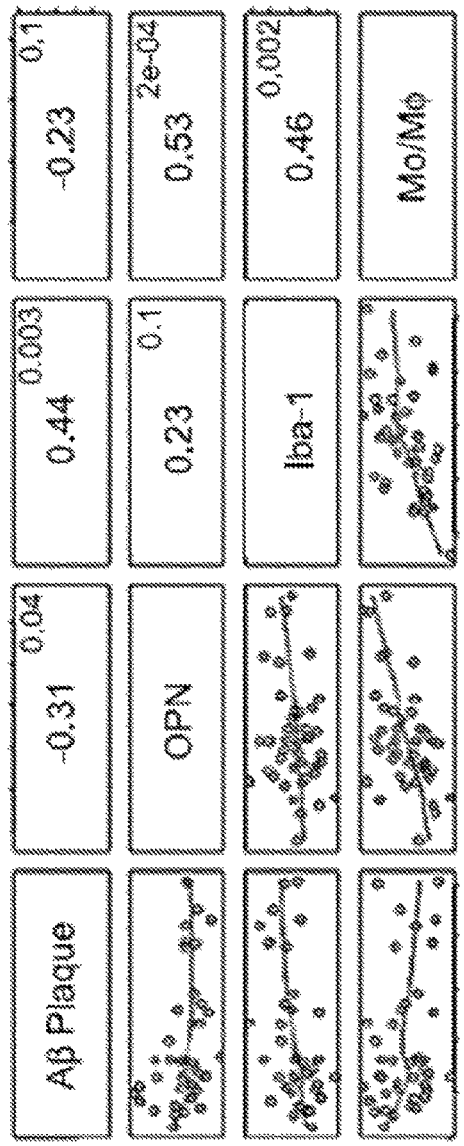
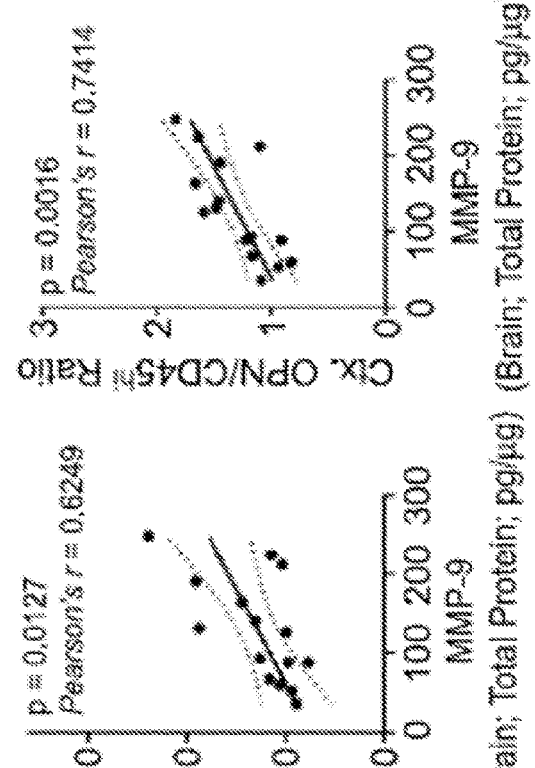
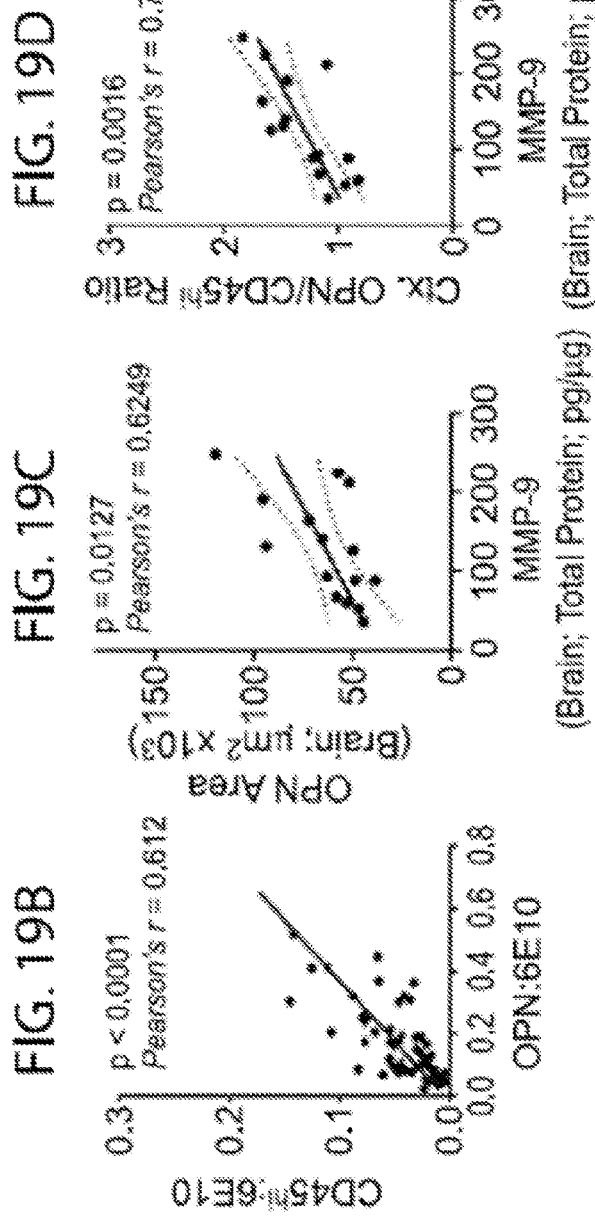
FIG. 19A
FIG. 19B
FIG. 19C
FIG. 19D

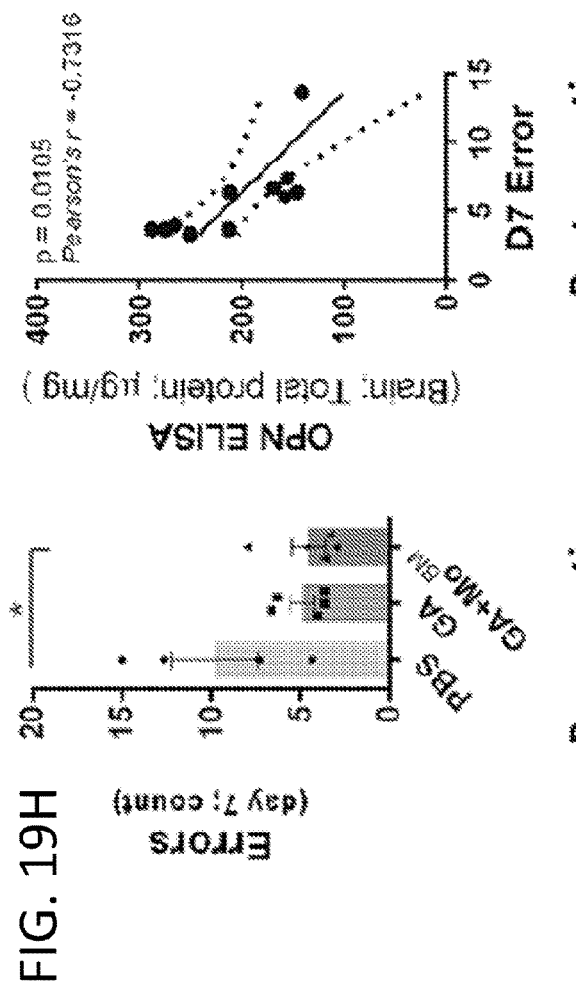
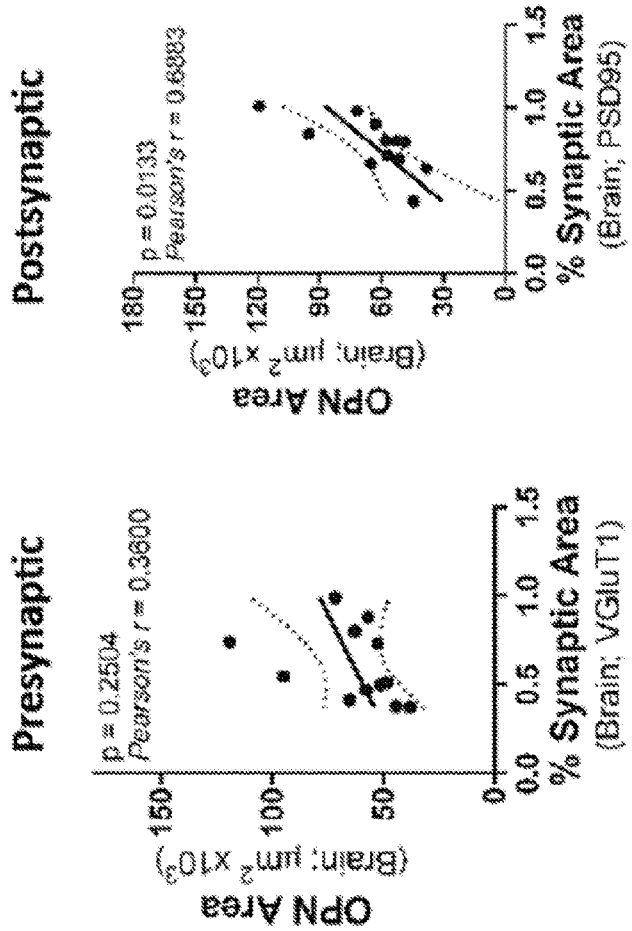
FIG. 19H
FIG. 19I

METHODS OF TREATING OR PREVENTING ALZHEIMER'S DISEASE AND ASSOCIATED CONDITIONS

CROSS-REFERENCE

This application is a U.S. National Phase of International Application No. PCT/US17/33875, filed May 22, 2017, which claims the benefit of U.S. Provisional Application No. 62/339,681 filed May 20, 2016, which is incorporated herein by reference in its entirety.

FIELD OF INVENTION

This invention relates to the treatment and prevention of Alzheimer's disease and associated conditions.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Alzheimer's disease is tightly linked to the cerebral accumulation of amyloid-β protein, particularly neurotoxic soluble amyloid-$β_{1-42}$ peptides and extracellular aggregations of amyloid-β plaques. The substantial increase in amyloidogenic amyloid-β forms is associated with neuroinflammation and downstream intracellular neurofibrillary tangles containing abnormal tau protein (encoded by MAPT). These are believed to be key contributors to synaptic and neuron loss leading to cognitive decline. Age-dependent accumulation of cerebral amyloid-β in sporadic forms of Alzheimer's disease appears to be due to insufficient clearance of amyloid-$β_{1-42}$ rather than its overproduction, as observed in cases with familial Alzheimer's disease.

Thus, there is a need in the art for methods of treating, preventing or reducing the likelihood of Alzheimer's disease, and addressing related pathologies.

BRIEF DESCRIPTION OF THE FIGURES

Exemplary embodiments are illustrated in referenced figures. It is intended that the embodiments and figures disclosed herein are to be considered illustrative rather than restrictive.

FIGS. 1A-1D depict $Aβ_{1-42}$ assemblies induce synaptic loss in primary cortical neurons in accordance with various embodiments of the present invention.

FIGS. 2A-2E show that GA-treated MΦ protect against $Aβ_{1-42}$-induced synaptic and neuritic loss in primary cortical neurons (CN) in accordance with various embodiments of the present invention.

FIGS. 3A-3E depict synaptic preservation in GA-immunized and adoptively transferred Mo in AD+ brains in accordance with various embodiments of the present invention.

FIGS. 4A-4D show that well-defined f/pf/o$Aβ_{1-42}$ assemblies are significantly engulfed by MΦ(CD36, scavenger receptor) with intracellular 6E10$^+$-Aβ in EEA1$^+$ endosomes in accordance with various embodiments of the present invention.

FIGS. 5A-5D show that GA induces OPN expression in MΦ along with enhanced cellular uptake of f$Aβ_{1-42}$ in accordance with various embodiments of the present invention.

FIG. 6A) Representative fluorescent micrographs of PBS or GA treated AD mouse brains. FIG. 6B) Quantitative multifactor correlogram analysis (Pearson's test; per animal) demonstrated significant linear associations between OPN and increased monocyte infiltration in GA immunized and GA+Mo$^{BM}$ treated ADtg mice, and reverse relations to Aβ plaque burden.

FIGS. 7A-7C depict effects of OPN inhibition on MΦ f$Aβ_{1-42}$ phagocytosis in accordance with various embodiments of the present invention.

FIGS. 8A-8D depict production and purification of stabilized Aβ assemblies in accordance with various embodiments of the present invention.

FIGS. 9A-9B depict schematics of the A) in vitro experiments (timeline in days) and B) in vivo experiments (timeline in months) in accordance with various embodiments of the present invention.

FIG. 10A) Quantification scheme for coronal brain sections. Representative Nissl stained image of mouse brain at Bregma −2.65 mm. Scale: 1 mm. Cingulate cortex (CC) (Comi et al., Journal of Alzheimer's disease: 2010 JAD 19:1143-1148), hippocampus (HC) and entorhinal cortex (EC) (Comi et al., Journal of Alzheimer's disease: 2010 JAD 19:1143-1148) were included in subsequent quantitative analyses. FIG. 10B) Representative fluorescent micrographs of brains from ADtg and age-matched WT mice, immunolabeled for anti-OPN, anti-human Aβ (6E10), and nuclei (DAPI). OPN immunostaining were detected within and around Aβ plaques in ADtg mice in all AD-associated brain regions (HC, CC and EC—arrows). In WT animals, no Aβ or OPN immunolabeling were detected. FIG. 10C) Peroxidase labeling of OPN in ADtg mice. OPN immunoreactivity (DAB) in HC and EC of ADtg mice, abundant in layers II/III of the EC and often forming plaque-like structures. FIG. 10D) OPN, NeuN, Tuj1 and GFAP expression in the CC and EC. FIG. 10E) OPN, Iba1 and DAPI expression in the CC and HC FIG. 10F) OPN ELISA in brain samples of 13 and 24 month old mice. Scale: 100 unless depicted; inserts: 10 μm.

FIGS. 11A-11L depict in accordance with various embodiments of the present invention, GA immunization in ADtg mice increases cerebral OPN expression while decreasing Aβ plaque burden. FIG. 11A) Fluorescent micrographs of coronal brain sections from HC (20×, top row) and CC (63×, middle row) regions displayed OPN and Aβ (6E10) expression patterns for all experimental groups: GA, GA+Mo$^{BM}$, and PBS control ADtg mice. DAPI was used to stain nuclei. Lower row includes single channel of OPN (lower left panel) and Aβ (lower right panel). GA-immunized groups with and without grafted Mo$^{BM}$ displayed enhanced cerebral OPN expression and reduced plaque burden compared with PBS controls. Scale: 100 FIG. 11B-11D) Quantitative IHC analyses of FIG. 11B) total OPN-immunoreactive (IR) area, FIG. 11C) 6E10$^+$-plaque area, and FIG. 11D) ratio of OPN-IR area to 6E10$^+$-plaque area for each section. FIG. 11E) ratio of OPN to 4G8 for each section. FIG. 11F) ratio of OPN to $Aβ_{42}$ levels for each section. FIG. 11G) OPN ELISA in the brain. FIG. 11H, 11I) Correlation analyses between OPN25 IR area and Aβ plaque burden FIG. 11H) in total brain regions and FIG. 11I) cortical regions. FIG. 11J) Correlation analysis between OPN ELISA and Aβ plaque area. FIG. 11K) Correlation analysis between OPN ELISA and Insoluble Aβ$_{42}$ ELISA. Correlation analyses performed with Pearson's test. FIG. 11L) OPN ELISA in the brain of WT and AD mice. The fold increases or percent reductions in mean values compared with PBS controls are indicated. n=5-8 mice per group. *p<0.05, p<0.001, *p<0.0001, ****p<0.00001.

FIGS. 12A-12F depict in accordance with various embodiments of the present invention, GA immunization of ADtg mice decreases vascular cerebral amyloid angiopathy (CAA) burden. Reduced vascular Aβ and Aβ$_{1-40}$ inverse correlation with OPN. FIG. 12A) Thio-S staining in PBS and GA-immunized ADtg mice. FIG. 12B) CAA score in PBS, GA-treated and GA-Mo$^{BM}$ treated mice. Last three graphs demonstrate the correlation of OPN ELISA to soluble Aβ$_{40}$, OPN ELISA to insoluble Aβ$_{40}$ and CAA score to OPN ELISA. FIG. 12C-F) Correlation analysis of CAA score to insoluble Aβ$_{40}$ (FIG. 12C), CAA score to soluble Aβ$_{40}$ (FIG. 12D), CAA score to ELISA insoluble Aβ$_{42}$ (FIG. 12E) and CAA score to soluble Aβ$_{42}$ (FIG. 12F).

FIGS. 13A-13G depict in accordance with various embodiments of the present invention, cerebral OPN expression by infiltrating monocyte-derived macrophages associated with Aβ plaque clearance. FIG. 13A-13C) Fluorescent micrographs of coronal brain sections from CC and EC regions of GA-immunized ADtg mice. Mo-derived macrophages (MΦ), predominantly responsible for OPN expression, were tightly associated with Aβ plaques. FIG. 13A) Infiltrating Mo/Mt identified with combined Iba1 and CD45 biomarker immunolabeling in GA-immunized ADtg mouse brains. Cerebral OPN, Aβr (6E10) and nuclei (DAPI) also shown. Arrow indicates an infiltrating OPN-expressing Iba1$^{+}$CD45$^{high}$ MΦ engulfing Aβ FIG. 13B) EC infiltrating monocytes expressing OPN were also identified in GA+Mo$^{BM}$-treated ADtg mouse brains through a second approach: adoptive transfer of a GFP-labeled CD115$^{+}$-monocyte subset injected into tail veins of symptomatic ADtg mice. GFP$^{+}$CD45$^{high}$-expressing monocytes showed high OPN expression and were distinguishable from resident microglia (GFP$^{-}$CD45$^{itermediate-low}$). FIG. 13C) OPN-expressing Iba-1$^{+}$ myelomonocytic cells were associated with plaques, especially at the border of EC. FIG. 13D-13E) Puncta staining patterns of subcellular OPN in vesicular compartments across the cell body and along Iba1$^{+}$ processes. Signal was particularly intense in the perinuclear subregion. Scale: 10 μm. FIG. 13F) OPN$^{+}$CD45$^{+}$ cell count in HC, CC, EC, and combined brain regions (Brain). GA-immunized groups had substantial increases in number of infiltrating OPN$^{+}$ myelomonocytic cells. Fold increases in mean values compared with PBS controls are indicated. FIG. 13G) Correlation analysis (Pearson's test) found a strong, significant linear association between OPN expression and infiltrating Iba1$^{+}$ CD45high macrophages. n=5-8 mice per group. *p<0.05, p<0.001, *p<0.0001, ****p<0.00001.

FIG. 14A) Experimental procedure of in vitro studies: bone marrow was isolated from WT mice (8- to 12-weeks-old) and cultured for 6-7 days in MCSF-enriched media to differentiate into macrophages (MΦ$^{BM}$). On day 6, cells were treated overnight with GA, siRNA, minocycline or GA with siRNA. On day 7, fibrillar Aβ (fAβ$_{1-42}$) was added in a subset of experiments and phagocytosis assays were carried out. Brefeldin A (BFA) treatment was performed 3 hours before phagocytosis. FIG. 14B-14C) Fluorescent micrographs of MΦ$^{BM}$ and GA-MΦ$^{BM}$ cells in vitro, before exposure to Aβ, and either without BFA treatment (FIG. 14B) or pretreatment with BFA (FIG. 14C). OPN is immunostained with anti-OPN antibody. MΦ$^{BM}$ expressed OPN, and GA treatment increased OPN expression. (FIG. 14B: insert) Subcellular OPN located inside transport vesicles in MΦ$^{BM}$. FIG. 14C) Round-shaped MΦ$^{BM}$ after BFA inhibition of OPN secretion. FIG. 14D) Quantitative ICC of OPN-immunoreactive area revealed upregulation of OPN in MΦ$^{BM}$ following GA treatment, before exposure to Aβ, with and without BFA inhibition. FIG. 14E) Quantitative ELISA of OPN levels in cell lysate from GA-treated and untreated MΦ$^{BM}$. FIG. 14F) Representative Western blot image of cell lysates from above-mentioned experimental groups, using goat monoclonal anti-OPN antibody. FIG. 14G) Quantification of Western blots. Results mirror ICC and ELISA data, indicating that regardless of Aβ exposure GA significantly induced OPN expression in MΦ$^{BM}$. Fold increases in mean values compared with PBS controls are indicated. Comparison between BFA-treated and untreated cells showed substantial accumulation of OPN in short periods (within one hour). FIG. 14H) Fluorescent micrographs of golgi, OPN and DAPI staining. FIG. 14I) Fluorescent micrographs of OPN, EEA1 and DAPI staining. FIG. 14J) OPN ELISA of WT mice treated with GA for varying time points. *p<0.05, p<0.001, *p<0.0001, ****p<0.00001. Scale: 20 μm, insert scale 5 μm.

FIGS. 15A-15P depict in accordance with various embodiments of the present invention, OPN-dependent increase of Aβ fibril uptake by GA-treated macrophages. Representative fluorescent micrographs and quantitative analyses of Aβ uptake and OPN expression in MΦ$^{BM}$ in primary cultures stimulated with fAβ$_{1-42}$ for 30 min. FIG. 15A) Higher magnification Z-stack image showing intracellular uptake of 6E10$^{+}$-Aβ along with subcellular OPN expression patterns. FIG. 15B-15C) Quantitative ICC of OPN expression and intracellular Aβ in GA-treated vs. untreated MΦ$^{BM}$. GA treatment lasted 24 hrs. Increased OPN expression and enhanced cellular uptake of fAβ$_{1-42}$ was found following GA treatment.

FIG. 15D-15E) Quantitative ELISA of OPN levels and intracellular Aβ$_{1-42}$ in GA-treated vs. untreated MΦ$^{BM}$. FIG. 15F) Fluorescent micrographs of OPN, CD36, 6E10 and DAPI staining in WT, KO and GA treated WT and KO mice. FIG. 15G-15H') Micrographs of MΦ$^{BM}$ (FIG. 15) untreated or (FIG. 15H-15H') GA-treated and co-labeled with antibodies against OPN, CD68, and 6E10. FIG. 15H-15H') MΦ$^{BM}$ pretreated with GA displaying enhanced fAβ$_{1-42}$ uptake. FIG. 15I-15J) ELISA analyses of cell lysate from MΦ$^{BM}$ and GA-MΦ$^{BM}$. FIG. 15K) Quantitative ICC of Aβ$_{40}$ uptake in GA-treated vs. untreated MΦ$^{BM}$. FIG. 15P) Aβ uptake in control, knock-out and GA-treated knock-outs. Fold increases or percent reductions in mean values compared with PBS controls are indicated. Scale: 10 μm. *p<0.05, p<0.001, *p<0.0001, ****p<0.00001.

FIGS. 16A-16J depict in accordance with various embodiments of the present invention, OPN mediates GA-acquired pro-healing phenotype in macrophages. FIG. 16A) Fluorescent micrographs of MΦ$^{BM}$ in primary cultures untreated or pretreated overnight with GA or siRNA$^{OPN}$ and immunostained for OPN. Lower row displays MΦ$^{BM}$ cell length by Zeiss Axiovision software. FIG. 16B) Quantitative analysis of cell length measurements. Polarization of MΦ$^{BM}$ towards an anti-inflammatory, pro-healing phenotype was associated with elongated cell shape, resulting from GA treatment with amplified OPN expression. OPN knockdown by siRNA produced shorter cells. FIG. 16C) Fluorescent images of MΦ$^{BM}$ treated with GA or minocycline (M) for 24 hours and then exposed to fAβ$_{1-42}$ for 30 min. Cells immunostained for iNOS and 6E10. FIG. 16D-16E) Quantitative ICC revealed that minocycline treatment increased iNOS expression, which reduced fAβ$_{1-42}$ phagocytosis in turn. FIG. 16F) Fluorescent image of MΦ$^{BM}$ immunostained for MMP-9, 6E10 and SCARA-1. FIG. 16G) Quantitative ICC revealed that GA treatment increased MMP-9 expression in vitro. FIG. 16H) MMP9 area (μm$^2$/cell) in WT, OPN KO and GA-treated OPN KO. FIG. 16I-16J) Western blot with rabbit-anti-OPN antibody and its respective quantitative band density analysis showed that OPN fragments derived from metalloproteinase (MMP) proteolysis were elevated with GA treatment, consistent with elevated MMP-9 production. OPN secretion and its proteolysis by MMP-mediated macrophage polarization towards an anti-inflammatory phenotype, resulting in amplified fAβ$_{1-42}$ phagocytosis. Fold increases or percent reductions in mean values compared with PBS controls are indicated. Scale: 50 μm. *p<0.05, p<0.001, *p<0.0001, ****p<0.00001.

FIGS. 17A-17C depict in accordance with various embodiments of the present invention, expression patterns of OPN in brain regions not associated with AD pathology. FIG. 17A) Fluorescent micrographs of coronal sections from ADtg and age-matched WT mouse brains, immuno-labeled for anti-OPN, Iba1$^+$-microglia and macrophages, and nuclei (DAPI). Patterns of OPN-immunostaining were detected in the striatum of WT and ADtg mice. OPN is not co-labeled with Iba1$^+$ microglia/macrophages, but immunolabeled the neurons. FIG. 17B) Peroxidase imaging of OPN in WT vs. ADtg mice. OPN immunoreactivity (DAB) in the striatum of WT and ADtg mice is selective to neurons and not detected in microglia or macrophages. FIG. 17C) Fluorescent micrographs of coronal sections from ADtg and age-matched WT mouse brains, immuno-labeled for anti-OPN, Tuj1-neurons and nuclei (DAPI). Scale: 100 μm.

FIGS. 18A-18D depict in accordance with various embodiments of the present invention, enhanced cerebral OPN expression by infiltrating monocytes following immune-based intervention in ADtg mice. FIG. 18A-18B) Quantitative IHC analyses of brain sections (CC, EC and HC) were assessed for FIG. 18A) OPN-positive area, and FIG. 18B) Ratios of OPN-positive area to 6E10$^+$ plaque area for each section. GA and GA+Mo$^{BM}$ groups showed increased OPN expression in all brain regions compared with PBS controls. FIG. 18B) Results showed significantly more OPN expression per plaque following GA and GA+Mo$^{BM}$ treatments. FIG. 18C) CAA score, correlation analysis of OPN ELISA to soluble Aβ$_{42}$ ELISA, correlation analysis of CAA score in HC to OPN ELISA and correlation of CAA score in CC to OPN ELISA. FIG. 18D) Correlation analysis of CAA score in HC and CC to soluble Aβ$_{40}$ and correlation of CAA score in HC and CC to insoluble Aβ$_{40}$.

Fold increases in mean values compared with PBS controls are indicated. N=5-8 mice per group. *p<0.05, p<0.001, *p<0.0001, ****p<0.00001.

Figure 19G:
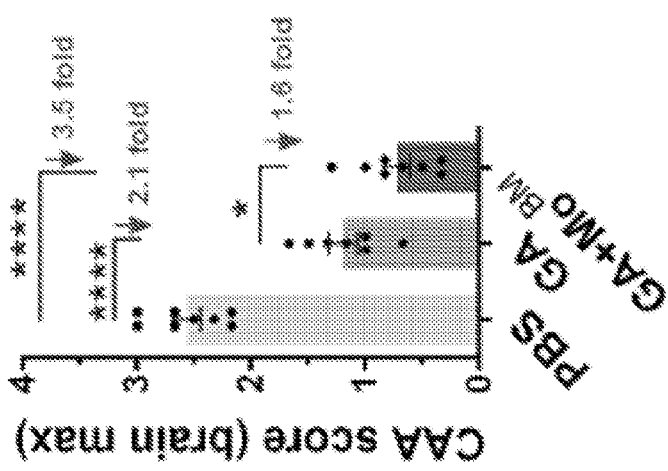
Figure 19F:
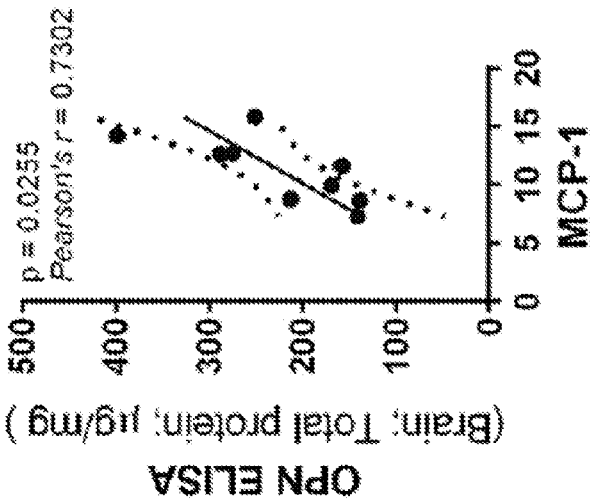
Figure 19E:
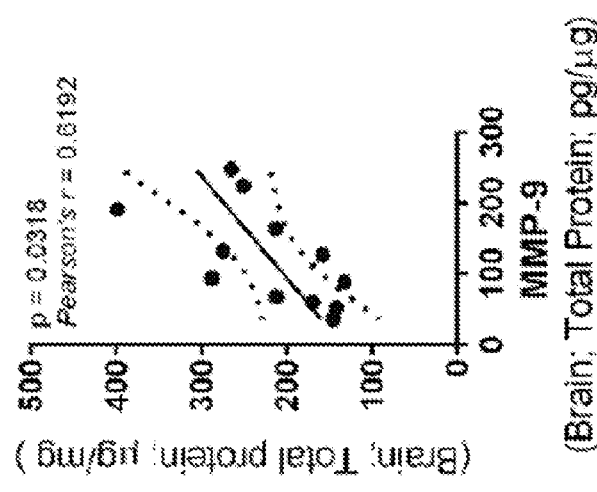
Figure 19K:
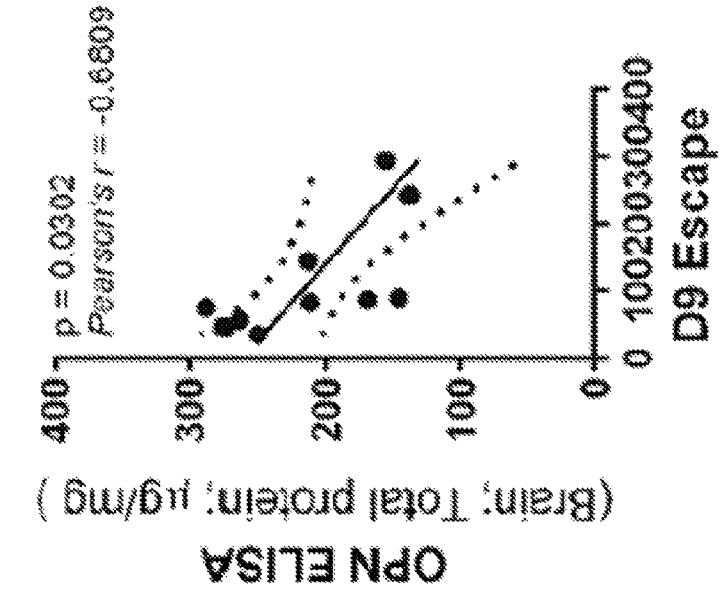
Figure 19J:
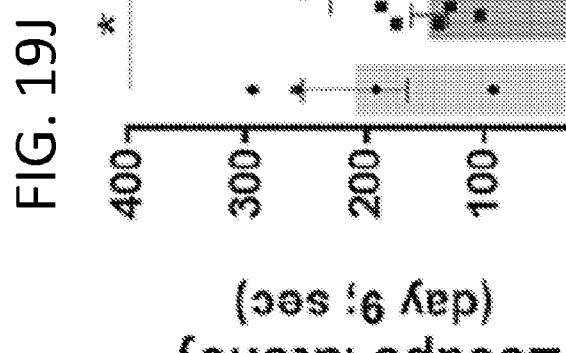

FIGS. 19A-19K depict in accordance with various embodiments of the present invention, cerebral OPN inversely correlates with plaque burden, and directly correlates with infiltrating monocytes and MMP-9. FIG. 19A) Advanced quantitative multifactor correlogram analysis demonstrated significant linear association between OPN and increased monocyte infiltration in GA-immunized and GA+Mo$^{BM}$ treated ADtg mice. An inverse relationship was found between OPN and Aβ plaque burden (correlation analysis performed per section). FIG. 19B) Additional correlation analyses validated significant positive linear correlation between OPN:6E10 and CD45hi:6E10 (infiltrating monocytes). FIG. 19C-19D) Correlation analyses demonstrating significant linear associations between OPN and MMP-9, (FIG. 19) and between OPN-expressing CD45$^{hi}$ monocytes and MMP-9 expression in ADtg mice. Results revealed a direct correlation between total brain MMP-9 and OPN levels and a stronger correlation between infiltrating OPN-expressing monocytes and cerebral MMP-9 levels. Correlation analyses performed using Pearson's test. FIG. 19E-19F) Correlation analysis of OPN ELISA to MMP-9 (FIG. 19E) and MCP-1 (FIG. 19F). FIG. 19G) Correlation analysis of CAA score in PBS, GA-treated and GA-treated Mo$^{BM}$. FIG. 19H-19K) Cerebral OPN expression correlates with post-synaptic density (FIGS. 19H-19I) and reduced cognitive function (FIG. 19J-19K). N=5-8 mice per group. *p<0.05, p<0.001, *p<0.0001, ****p<0.00001.

Figure 20:
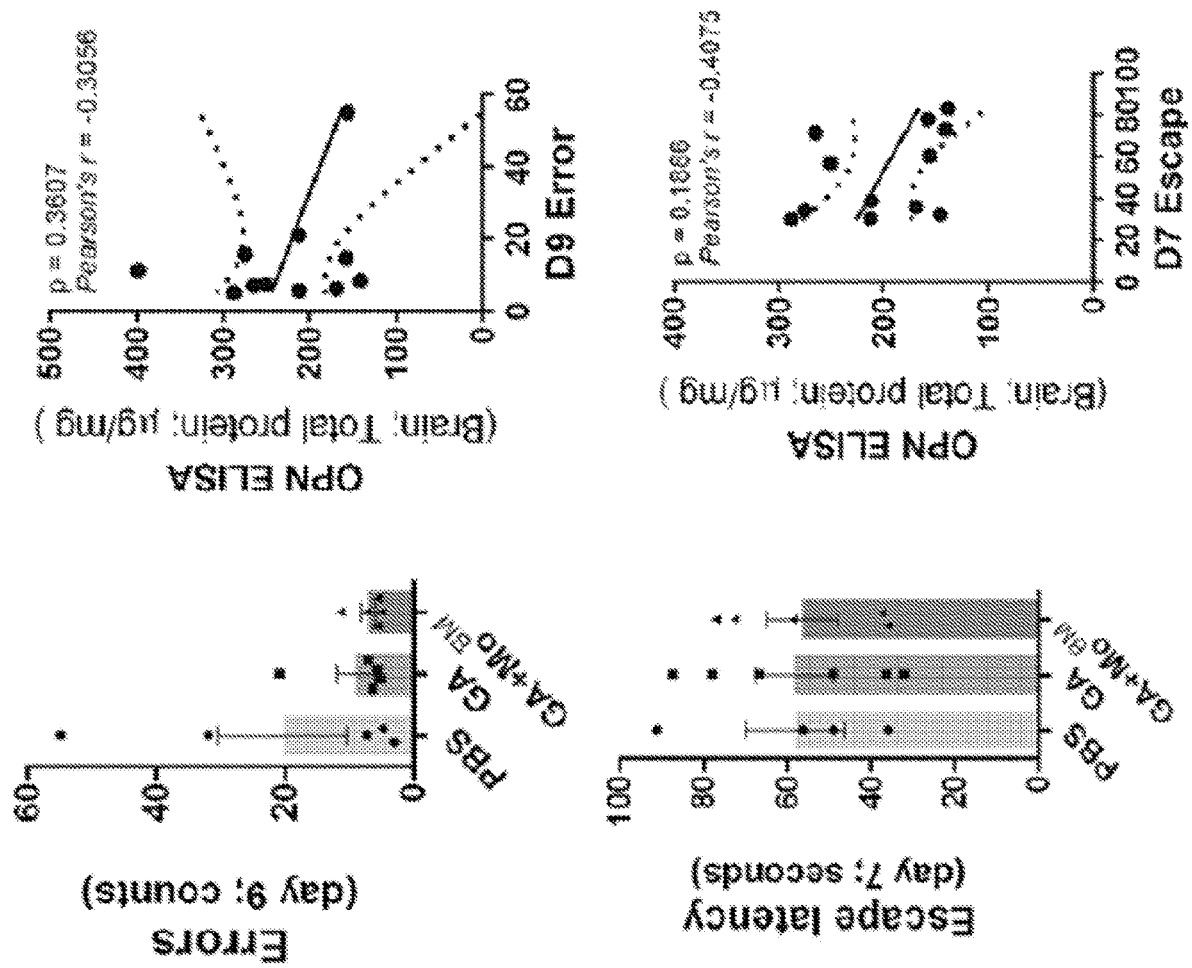

FIG. 20 depicts in accordance with various embodiments of the present invention, GA immunization and blood enrichment with monocytes of ADtg mice reduces cognitive deposit and increases postsynatptic preservation.

SUMMARY OF THE INVENTION

Various embodiments of the present invention provide for a method of treating, preventing or reducing the likelihood of Alzheimer's disease, alleviating a symptom of Alzheimer's disease, rescuing synaptic structure and/or cognitive function, enhancing the clearance of pathological amyloid-β forms or inhibiting the decline of neuronal structure and function in a subject in need thereof comprising: providing a composition that, when administered to the subject, results in increased levels of osteopontin (OPN) relative to a normal subject; and administering an amount of the composition to the subject sufficient to increase said levels of OPN.

In various embodiments, the composition comprises OPN expressing innate immune cells, recombinant OPN, OPN fragments, OPN derivatives, OPN mimetics, OPN analogues or a combination thereof.

In various embodiments, the composition stimulates expression of OPN in innate immune cells. In various other embodiments, the innate immune cells comprise monocytes, macrophages or combinations thereof.

In some embodiments, the monocytes comprise bone marrow-derived monocytes, spleen-derived monocytes, 115CD positive monocytes (CD115$^+$ monocytes) or combinations thereof. In some other embodiments, the monocytes are infiltrating monocytes and become OPN expressing macrophages in the brain. In yet other embodiments, the innate immune cells are phagocytic.

In various embodiments, glatiramer acetate (GA) is administered to stimulate expression of OPN in innate immune cells. In some embodiments, the innate immune cells are stimulated ex vivo or in vivo.

In various embodiments, innate immune cells expressing OPN are administered to the subject by adoptive cell transfer or bone marrow transplantation. In various embodiments, the innate immune cells over-express OPN.

In various embodiments, the composition is administered by a method selected from the group consisting of direct delivery to the subject, viral vector delivery, a liposomal delivery system, or nanodrug delivery system.

In various embodiments, the symptom of Alzheimer's disease is selected from the group consisting of memory loss, decline in non-memory aspects of cognition, impaired reasoning or judgment, behavior changes, carry out multi-step tasks, hallucinations, delusions, paranoia and combinations thereof.

In various embodiments, the administration of the composition results in an increase in MMP-9.

In various embodiments, elevated OPN expression results in decreased levels of a misfolded protein in the subject. In various other embodiments, the misfolded protein is amyloid beta (Aβ). In yet other embodiments, the Aβ is $A\beta_{40}$ and/or $A\beta_{42}$.

Various embodiments of the present invention also provide for a method of improving cognitive function in a subject in need thereof, comprising: providing a composition that, when administered to the subject, results in increased levels of osteopontin (OPN) relative to a normal subject; and administering an amount of the composition to the subject sufficient to increase said levels of OPN.

In various embodiments, the composition comprises OPN expressing innate immune cells, recombinant OPN, OPN fragments, OPN derivatives, OPN mimetics, OPN analogues or a combination thereof.

In some embodiments, the composition stimulates expression of OPN in innate immune cells. In various other embodiments, the innate immune cells comprise monocytes, macrophages or combinations thereof. In other embodiments, the monocytes comprise bone marrow-derived monocytes, spleen-derived monocytes, CD115 positive monocytes (CD115+ monocytes) or combinations thereof. In yet other embodiments, the monocytes are infiltrating monocytes and become OPN expressing macrophages in the brain. In certain embodiments, the innate immune cells are phagocytic.

In various embodiments, the composition comprises glatiramer acetate (GA). In various other embodiments, the innate immune cells are stimulated ex vivo or in vivo.

In various embodiments, the innate immune cells expressing OPN are administered to the subject by adoptive cell transfer or bone marrow transplantation. In various embodiments, the innate immune cells over-express OPN.

In various embodiments, the composition is administered by a method selected from the group consisting of direct delivery to the subject, viral vector delivery, a liposomal delivery system, or nanodrug delivery system.

In various embodiments, the symptom of Alzheimer's disease is selected from the group consisting of memory loss, decline in non-memory aspects of cognition, impaired reasoning or judgment, behavior changes, carry out multi-step tasks, hallucinations, delusions, paranoia and combinations thereof.

In various embodiments, the administration of the composition results in an increase in MMP-9. In various other embodiments, increased levels of OPN results in decreased levels of a misfolded protein in the subject, decreased inflammation in the subject, increased synaptic regeneration in the subject, recruitment of macrophages to an amyloid beta (Aβ) plaque site in the subject, or combinations thereof.

In other embodiments, wherein the misfolded protein is Aβ. In yet other embodiments, the Aβ is $A\beta_{40}$ and/or $A\beta_{42}$.

In various embodiments, the innate immune cells with increased OPN expression can be administered to the blood and/or brain of the subject in need thereof.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., Revised, J. Wiley & Sons (New York, N.Y. 2006); March, *Advanced Organic Chemistry Reactions, Mechanisms and Structure* $7^{th}$ ed., J. Wiley & Sons (New York, N.Y. 2013); and Sambrook and Russel, *Molecular Cloning: A Laboratory Manual* $4^{th}$ ed., Cold Spring Harbor Laboratory Press (Cold Spring Harbor, N.Y. 2012), provide one skilled in the art with a general guide to many of the terms used in the present application. For references on how to prepare antibodies, see D. Lane, *Antibodies: A Laboratory Manual* $2^{nd}$ ed. (Cold Spring Harbor Press, Cold Spring Harbor N.Y., 2013); Kohler and Milstein, (1976) Eur. J. Immunol. 6: 511; Queen et al. U.S. Pat. No. 5,585,089; and Riechmann et al., Nature 332: 323 (1988); U.S. Pat. No. 4,946,778; Bird, Science 242:423-42 (1988); Huston et al., Proc. Natl. Acad. Sci. USA 85:5879-5883 (1988); Ward et al., Nature 334:544-54 (1989); Tomlinson I. and Holliger P. (2000) Methods Enzymol, 326, 461-479; Holliger P. (2005) Nat. Biotechnol. September; 23(9):1126-36).

One skilled in the art will recognize many methods and materials similar or equivalent to those described herein, which could be used in the practice of the present invention. Indeed, the present invention is in no way limited to the methods and materials described.

As used herein, "OPN" refers to osteopontin, whose reference encompasses full length, functional fragments, biologically active fragments. In some embodiments, OPN analogues, derivatives and/or mimetics can also be referenced.

As used herein, "adoptive cell transfer" refers to the transfer of cells into a subject. The cells may have originated from the subject or from another individual (donor).

As used herein, "innate immune cells" refers to cells of the innate immune system, which include, but are not limited to monocytes, macrophages, neutrophils, eosinophils, basophils and/or natural killer cells.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

The term "therapeutically effective amount" refers to an amount of a cell population, stimulated or genetically modified cells, an antibody, polypeptide, polynucleotide, small organic molecule, or other drug effective to "treat" a disease or disorder in a subject or mammal. In the case of Alzheimer's Disease, the therapeutically effective amount of OPN can reduce the severity of Alzheimer's Disease symptoms. These include, but are not limited to, memory loss, decline in non-memory aspects of cognition, impaired reasoning or judgment, behavior changes, carrying out multistep tasks, hallucinations, delusions, and paranoia.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. "Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

Described herein, the inventors found an upregulation of osteopontin along with reduced amyloid β-protein (Aβ) plaques in the entorhinal cortex, cingulate cortex, and hippocampus of GA-immunized ADtg mice. Treatment combining GA and peripheral blood enrichment of $CD115^+$ monocytes further increased osteopontin levels surrounding residual Aβ plaques. Osteopontin was predominantly expressed by infiltrating monocyte-derived macrophages involved in Aβ-plaque uptake. In vitro studies, corroborating the in vivo findings, showed that GA directly upregulates osteopontin expression in bone marrow-derived macrophages and further promotes an anti-inflammatory phenotype highly phagocytic of Aβ. Without being bound to any particular theory, this study suggests a novel role for osteopontin as a mediator of the therapeutic effects of GA-activated macrophages in AD models.

Various embodiments of the present invention are based, at least in part, on these findings and addresses the need in the art for methods of elevating OPN, methods of treating, preventing or reducing the likelihood of Alzheimer's disease, and methods of improving cognitive function in a subject in need thereof.

Treatment of Alzheimer's Disease

Various embodiments of the present invention provide for a method of treating, preventing or reducing the likelihood of Alzheimer's disease, alleviating a symptom of Alzheimer's disease, rescuing synaptic structure and/or cognitive function, enhancing the clearance of pathological amyloid-β forms or inhibiting the decline of neuronal structure and function in a subject in need thereof comprising: providing a composition that, when administered to the subject, results in increased levels of osteopontin (OPN) relative to a normal subject; and administering an amount of the composition to the subject sufficient to increase said levels of OPN.

Various embodiments of the present invention also provide for a method of treating Alzheimer's disease, comprising: providing a composition that, when administered to the subject, results in increased levels of osteopontin (OPN) relative to a normal subject; and administering an amount of the composition to the subject sufficient to increase said levels of OPN.

Various embodiments of the present invention also provide for a method of preventing Alzheimer's disease, comprising: providing a composition that, when administered to the subject, results in increased levels of osteopontin (OPN) relative to a normal subject; and administering an amount of the composition to the subject sufficient to increase said levels of OPN.

Various embodiments of the present invention also provide for a method of reducing the likelihood of Alzheimer's disease, comprising: providing a composition that, when administered to the subject, results in increased levels of osteopontin (OPN) relative to a normal subject; and administering an amount of the composition to the subject sufficient to increase said levels of OPN.

Various embodiments of the present invention also provide for a method of alleviating a symptom of Alzheimer's disease, comprising: providing a composition that, when administered to the subject, results in increased levels of osteopontin (OPN) relative to a normal subject; and administering an amount of the composition to the subject sufficient to increase said levels of OPN.

Various embodiments of the present invention also provide for a method of rescuing synaptic structure in Alzheimer's disease, comprising: providing a composition that, when administered to the subject, results in increased levels of osteopontin (OPN) relative to a normal subject; and administering an amount of the composition to the subject sufficient to increase said levels of OPN.

Various embodiments of the present invention also provide for a method of rescuing cognitive function in Alzheimer's disease, comprising: providing a composition that, when administered to the subject, results in increased levels of osteopontin (OPN) relative to a normal subject; and administering an amount of the composition to the subject sufficient to increase said levels of OPN.

Various embodiments of the present invention provide for a method of enhancing the clearance of pathological amyloid-β forms comprising: providing a composition that, when administered to the subject, results in increased levels of osteopontin (OPN) relative to a normal subject; and administering an amount of the composition to the subject sufficient to increase said levels of OPN.

Various embodiments of the present invention provide for a method of inhibiting the decline of neuronal structure and function comprising: providing a composition that, when administered to the subject, results in increased levels of osteopontin (OPN) relative to a normal subject; and administering an amount of the composition to the subject sufficient to increase said levels of OPN.

In various embodiments, the composition comprises OPN expressing innate immune cells, recombinant OPN, OPN fragments, OPN derivatives, OPN mimetics, OPN analogues or a combination thereof.

In various embodiments, the composition stimulates expression of OPN in innate immune cells. In various other embodiments, the innate immune cells comprise monocytes, macrophages or combinations thereof.

In some embodiments, the monocytes comprise bone marrow-derived monocytes, spleen-derived monocytes, CD115 positive monocytes (CD115$^+$ monocytes) or combinations thereof. In some other embodiments, the monocytes are infiltrating monocytes and become OPN expressing macrophages in the brain. In some embodiments, the monocytes over-express OPN. In other embodiments, the macrophages over-express OPN. In yet other embodiments, the innate immune cells are phagocytic.

In various embodiments, the composition comprises glatiramer acetate (GA). In some embodiments, the innate immune cells are stimulated ex vivo or in vivo.

In various embodiments, innate immune cells expressing OPN are administered to the subject by adoptive cell transfer or bone marrow transplantation. In various embodiments, the innate immune cells over-express OPN.

In various embodiments, the composition is administered by a method selected from the group consisting of direct delivery to the subject, viral vector delivery, a liposomal delivery system, or nanodrug delivery system.

In various embodiments, the symptom of Alzheimer's disease is selected from the group consisting of memory loss, decline in non-memory aspects of cognition, impaired reasoning or judgment, behavior changes, carry out multistep tasks, hallucinations, delusions, paranoia and combinations thereof.

In various embodiments, the administration of the composition results in an increase in MMP-9.

In various embodiments, elevated OPN expression results in decreased levels of a misfolded protein in the subject. In other embodiments, the misfolded protein is amyloid beta (Aβ). In yet other embodiments, the Aβ is Aβ$_{40}$ and/or Aβ$_{42}$. In various embodiments, the misfolded Aβ protein comprises plaques and/or vascular Aβ deposits.

Various embodiments of the present invention also provide for a method of treating, preventing or reducing the likelihood of Alzheimer's disease, alleviating a symptom of Alzheimer's disease, rescuing synaptic structure and/or cognitive function, enhancing the clearance of pathological amyloid-β forms or inhibiting the decline of neuronal structure and function comprising: enriching the blood with monocytes; and stimulating the monocytes thereby increasing osteopontin (OPN) expression in the brain.

In various embodiments, adoptive cell transfer or bone marrow transplantation is performed to administer the monocytes and enrich the blood with monocytes. In various embodiments, the monocytes over-express OPN. In some embodiments, the monocytes administered using adoptive cell transfer are bone marrow-derived monocytes, spleen-derived monocytes, CD115 positive monocytes (CD115$^+$ monocytes) or combinations thereof. In other embodiments, the monocytes are stimulated with glatiramer acetate (GA). In various embodiments, the monocytes are stimulated ex vivo or in vivo.

In various embodiments, enriching the blood with monocytes comprises administering stem cells collected from the bone marrow and/or the blood. In various other embodiments, enriching the blood with monocytes comprises administering CD115 positive monocytes (CD115$^+$ monocytes). In yet other embodiments, the monocytes are infiltrating monocytes and become OPN expressing macrophages in the brain. In some embodiments, the monocytes over-express OPN. In other embodiments, the macrophages over-express OPN.

In various embodiments, the symptom of Alzheimer's disease is selected from the group consisting of memory loss, decline in non-memory aspects of cognition, impaired reasoning or judgment, behavior changes, unable to carry out multistep tasks, hallucinations, delusions, paranoia and combinations thereof.

In various embodiments, stimulating the monocytes causes an increase in MMP-9.

Various embodiments of the present invention also provide for a method of treating Alzheimer's disease. Various embodiments of the present invention provide for a method of alleviating a symptom of Alzheimer's disease. Symptoms of Alzheimer's disease include but are not limited to memory loss, decline in non-memory aspects of cognition (e.g., word-finding, vision/spatial issues), impaired reasoning or judgment, behavior changes, carry out multistep tasks, hallucinations, delusions, and paranoia. Various embodiments of the present invention provide for a method of rescuing synaptic structure and/or cognitive function. Various embodiments of the present invention provide for a method of enhancing the clearance of pathological amyloid-β forms and inhibit the decline of neuronal structure and function.

In various embodiments, the method comprises performing bone marrow transplantation on a subject. In further embodiments, the method further comprises administering glatiraer acetate (GA). Administering the GA does not necessarily need to occur after the bone marrow transplantation. Indeed, GA can be administered before, substantially with, and/or after the bone marrow transplantation.

In some embodiments, the bone marrow transplant is an allogeneic bone marrow transplant. In some embodiments, the bone marrow transplant is an autologous bone marrow transplant. In some embodiments, performing the bone marrow transplantation comprises administering stem cells collected from the bone marrow. In other embodiments, performing the bone marrow transplantation comprises administering stem cells collected from the blood (e.g., via leukapheresis).

In various embodiments, the method comprises performing adoptive cell transfer on a subject.

In some embodiments, performing adoptive cell transfer comprises administering macrophages to the subject. In further embodiments, the method further comprises administering glatiraer acetate (GA). Administering the GA does not necessarily need to occur after the adoptive cell transfer. Indeed, GA can be administered before, substantially with, and/or after the adoptive cell transfer.

In some embodiments, the macrophages are autologous macrophages. In other embodiments, the macrophages are allogeneic macrophages. In some embodiments, the macrophages are monocyte-derived macrophages. Monocyte-derived macrophages as used herein refer to macrophages that differentiated from monocytes. In particular embodiments, performing the performing adoptive cell transfer comprise administering to the subject monocyte-derived macrophages, wherein the monocytes were obtained from bone marrow. In some embodiments, the macrophages have been treated with glatiramer acetate (GA). In particular embodiments, the method comprises administering to the subject monocyte-derived macrophages that have been treated with GA.

In some embodiments, performing adoptive cell transfer comprises administering bone marrow derived monocytes to the subject. In further embodiments, the method further comprises administering glatiraer acetate (GA). Administering the GA does not necessarily need to occur after the adoptive cell transfer. Indeed, GA can be administered before, substantially with, and/or after the adoptive cell transfer.

In some embodiments, the bone marrow derived monocytes are autologous bone marrow derived monocytes. Bone marrow derived monocytes as used herein refer to monocytes that are obtained from the bone marrow. In other embodiments, the bone marrow derived monocytes are allogeneic bone marrow derived monocytes. In some embodiments, the bone marrow derived monocytes are CD115 positive monocytes (CD115$^+$ monocytes). In some embodiments, the bone marrow derived monocytes have been treated with glatiramer acetate (GA). In particular embodiments, the method comprises administering to the subject CD115$^+$ bone marrow derived monocytes that have been treated with GA.

Method of Elevating Osteopontin

Various embodiments of the present invention provide for a method of elevating osteopontin (OPN), comprising stimulating an increase in the expression of OPN in innate immune cells, thereby elevating OPN.

Various embodiments of the present invention provide for a method of elevating osteopontin (OPN), comprising administering OPN expressing innate immune cells, thereby elevating OPN.

In various embodiments, the OPN is full length OPN or functional fragments thereof. In various embodiments, OPN expression is increased by stimulating the innate immune cells with glatiramer acetate (GA). In some embodiments, the innate immune cells are stimulated ex vivo or in vivo.

In various embodiments, the method further comprises administering the innate immune cells with increased OPN expression to a subject in need thereof. In some embodiments, the innate immune cells with increased OPN expression are administered to the blood and/or to the brain of the subject in need thereof.

In various embodiments, the innate immune cells are phagocytic. In other embodiments, the innate immune cells comprise monocytes, macrophages or combinations thereof. In yet other embodiments, the monocytes comprise bone marrow-derived monocytes, spleen-derived monocytes, CD115 positive monocytes (CD115$^+$ monocytes) or combinations thereof. In some other embodiments, the monocytes are infiltrating monocytes and become OPN expressing macrophages in the brain.

In various embodiments, the method further comprises the targeted delivery of full length OPN or functional fragments thereof. In various embodiments, the method for targeted delivery of full length OPN or functional fragments thereof is selected from the group consisting of delivery of recombinant OPN, viral vector delivery, via a liposomal delivery system, delivery of exosomes containing OPN or nanodrug delivery systems.

In various embodiments, elevating OPN results in the treatment, the prevention or reduction of the likelihood of Alzheimer's disease and/or the amelioration of Alzheimer's Disease symptoms in the subject.

Various embodiments of the present invention provide for a method of elevating osteopontin (OPN), comprising stimulating an increase in the expression of OPN in innate immune cells, thereby elevating OPN.

Various embodiments of the present invention provide for a method of elevating osteopontin (OPN), comprising administering OPN expressing innate immune cells, thereby elevating OPN.

In various embodiments, the OPN is full length OPN or functional fragments thereof.

In various embodiments, the method further comprises administering the innate immune cells with increased OPN expression to a subject in need thereof. In some embodiments, the innate immune cells with increased OPN expression are administered to the blood and/or to the brain of the subject in need thereof.

In various embodiments, the innate immune cells are phagocytic. In other embodiments, the innate immune cells comprise monocytes, macrophages or combinations thereof. In yet other embodiments, the monocytes comprise bone marrow-derived monocytes, spleen-derived monocytes, CD115 positive monocytes (CD115$^+$ monocytes) or combinations thereof. In some other embodiments, the monocytes are infiltrating monocytes and become OPN expressing macrophages in the brain.

In various embodiments, elevating OPN results in the treatment, the prevention or reduction of the likelihood of Alzheimer's disease and/or the amelioration of Alzheimer's Disease symptoms in the subject.

Various embodiments of the present invention provide for a method of elevating osteopontin (OPN), comprising stimulating an increase in the expression of OPN in innate immune cells, thereby elevating OPN.

Various embodiments of the present invention provide for a method of elevating osteopontin (OPN), comprising administering OPN expressing innate immune cells, thereby elevating OPN.

In various embodiments, the OPN is full length OPN or functional fragments thereof.

In various embodiments, OPN is elevated by the targeted delivery of full length OPN or functional fragments thereof. In various embodiments, the method for targeted delivery of full length OPN or functional fragments thereof is selected from the group consisting of delivery of recombinant OPN, viral vector delivery, via a liposomal delivery system, delivery of exosomes containing OPN or nanodrug delivery systems.

In various embodiments, elevating OPN results in the treatment, the prevention or reduction of the likelihood of Alzheimer's disease and/or the amelioration of Alzheimer's Disease symptoms in the subject.

In various embodiments, the delivery of OPN elevates OPN in the brain and results in the treatment, and/or the prevention or reduction of the likelihood of Alzheimer's disease in the subject. More specifically, the invention includes a method of treating Alzheimer's disease and reducing the progression of Alzheimer's disease by administering a therapeutically effective amount of an OPN based therapy to a mammal. The invention also includes a method of delivering OPN to brain tissue of a mammal having Alzheimer's disease. In various embodiments, the mammal is a human. While not wishing to be bound by any particular theory, it is believed that the administration of OPN based therapies will modulate the levels of amyloid plaques in the brain and/or by preventing the additional build-up thereof, and can be effective in the treatment of Alzheimer's disease by favorably modifying the phenotype of circulating monocytes and/or monocyte derived macrophages. As shown herein, the administration of OPN based therapies mediates Aβ clearance via macrophages that are polarized toward a more pro-healing, anti-inflammatory and highly phagocytic phenotype. One of ordinary skill in the art will readily appreciate that these effects are beneficial to the treatment of Alzheimer's disease.

Methods for elevating OPN include, but are not limited to, 1) subcutaneous immunizations with GA resulting in the elevation of endogenous OPN, 2) peripheral blood or nasal delivery of recombinant OPN expressed in a viral vector (i.e., AAV8 or AAV9), 3) peripheral injection of exosomes containing OPN, 4) adoptive transfer to the peripheral blood of monocytes pre-treated with GA to overexpress OPN and 5) encapsulate OPN in a liposomal delivery system to be injected peripherally to the blood or given orally.

In various embodiments, elevating OPN in the brain is accomplished by delivery of recombinant OPN, viral vector delivery, via a liposomal delivery system, delivery of exosomes containing OPN or nanodrug delivery systems.

Various embodiments of the present invention provide for a method of elevating osteopontin (OPN) by delivering OPN to the brain of a subject by administering a therapeutically effective amount of recombinant OPN.

The term "recombinant DNA molecule", as used herein, refers to a DNA molecule which is comprised of segments of DNA joined together by means of molecular biological techniques known to one of skill in the art, including but not limited to genetic recombination (i.e., molecular cloning).

The term "recombinant protein" or "recombinant polypeptide", as used herein, refers to a protein molecule which is expressed from a recombinant DNA molecule.

Recombinant OPN can be synthesized by using well known methods including recombinant methods and chemical synthesis. Recombinant methods of producing a peptide through the introduction of a vector including nucleic acid encoding the peptide into a suitable host cell is well known in the art and can also be chemically synthesized using methods well known in the art. See for example, Bodanszky, M., Principles of Peptide Synthesis, Springer-Verlag, New York, N.Y. (1984); W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, $2^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference.

Systems for cloning and expressing a recombinant protein/polypeptide of the invention include various microorganisms and cells that are well known in recombinant technology. These include, for example, various strains of *E. coli, Bacillus, Streptomyces*, and *Saccharomyces*, as well as mammalian, yeast and insect cells. OPN can be produced as a polypeptide or fusion protein. Suitable vectors for producing peptides are known and available from private and public laboratories and depositories and from commercial vendors. Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques.

Recombinant OPN can comprise of full length OPN or functional fragments thereof. The recombinant OPN generated can be expressed in a viral vector, encapsulated in a liposome, expressed on an exosome or included in a nanodrug delivery system.

Various embodiments of the present invention also provide for a method of elevating osteopontin (OPN) by delivering OPN to the brain of a subject using viral vector delivery. In various embodiments, an OPN viral vector is administered to the subject.

"Vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

In various embodiments, the viral vector is an AAV vector. "AAV vector" refers to any vector derived from any adeno-associated virus serotype, including, without limitation, AAV-1, AAV-2, AAV-3, AAV-4, AAV-5, AAV-7, AAV-8, AAV-9, and AAV-10 and the like. AAV vectors can have one or more of the AAV wild-type genes deleted in whole or in part, preferably the Rep and/or Cap genes, but retain functional flanking ITR sequences. Functional ITR sequences are generally necessary for the rescue, replication, packaging and potential chromosomal integration of the AAV genome. Thus, an AAV vector is defined herein to include at least those sequences required in cis for replication and packaging (e.g., functional ITRs) of the virus. The ITRs need not be the wild-type nucleotide sequences, and may be altered (e.g., by the insertion, deletion or substitution of nucleotides) so long as the sequences provide for functional rescue, replication and packaging.

"Recombinant virus" refers to a virus that has been genetically altered (e.g., by the addition or insertion of a heterologous nucleic acid construct into the particle).

"AAV virion" refers to a complete virus particle, such as a wild-type ("wt") AAV virus particle (i.e., including a linear, single-stranded AAV nucleic acid genome associated with an AAV capsid protein coat). In this regard, single-stranded AAV nucleic acid molecules of either complementary sense (i.e., "sense" or "antisense" strands) can be packaged into any one AAV virion; both strands are equally infectious. In addition, the AAV capsid protein coat can be from any of the various AAV serotypes depending on the target of the AAV virion.

A "recombinant AAV virion" or "rAAV virion" is defined herein as an infectious, replication-defective virus composed of an AAV protein shell, encapsulating a heterologous DNA molecule of interest (e.g., genes encoding OPN) which is flanked on both sides by AAV ITRs. A rAAV virion may be produced in a suitable host cell which has had an AAV vector, AAV Rep and Cap functions and helper virus functions introduced therein. In this manner, the host cell is rendered capable of producing AAV replication and capsid proteins that are required for replicating and packaging the AAV vector (i.e., containing a recombinant nucleotide sequence of interest) into recombinant virion particles for subsequent gene delivery. The complete transgene may consist of a promoter, the coding sequences, usually a cDNA and a polyadenylation signal.

A transgene may also include regulatory sequences and intron regions. Promoters that would regulate transgene expression may include constitutive, inducible and tissue-specific promoters. The term "promoter region" is used herein in its ordinary sense to refer to a nucleotide region including a DNA regulatory sequence, wherein the regulatory sequence is derived from a gene which is capable of binding RNA polymerase and initiating transcription of a downstream (3'-direction) coding sequence.

A "gene" or "coding sequence" or a sequence which "encodes" a particular protein is a nucleic acid molecule that is transcribed (in the case of DNA) and translated (in the case of mRNA) into a polypeptide in vitro or in vivo when placed under the control of appropriate regulatory sequences.

The term "transfection" is used herein to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties, such as a plasmid vector and other nucleic acid molecules, into suitable host cells. The term refers to both stable and transient uptake of the genetic material.

The term "transduction" denotes the delivery of a DNA molecule to a recipient cell either in vivo or in vitro, via any method of gene delivery, including viral vector delivery.

AAV vectors are constructed using known techniques to at least provide, components in the direction of transcription, (a) control elements including a transcriptional initiation region, (b) the OPN DNA of interest and (c) a transcriptional termination region. Moreover, any coding sequence sufficiently homologous to the OPN coding sequence so as to exhibit functional properties substantially similar to the OPN coding sequence can be used in connection with alternate embodiments of the present invention. The control elements are selected to be functional in the targeted cell(s). The resulting construct, which contains the components, may be bounded (5' and 3') with functional AAV ITR sequences. AAV ITRs used in the vectors of the invention need not have a wild-type nucleotide sequence, and may be altered (e.g., by the insertion, deletion or substitution of nucleotides). Additionally, AAV ITRs may be derived from any of several AAV serotypes, including, without limitation, AAV-1, AAV-2, AAV-3, AAV-4, AAV-5, AAVX7, AAV-8, AAV-9, AAV-10 and the like.

For instance, AAV vectors including heterologous DNA corresponding to an OPN coding sequence may be generated by any conventional technique known in the art. In various embodiments the AAV vector is produced by the process of: (i) providing a first plasmid that comprises OPN or a fragment thereof, (ii) providing a second plasmid that is complementary to the first plasmid and which comprises components for rescue and packaging, (iii) co-transfecting the first and second plasmids into a host cell, and (iv) generating a quantity of said AAV vector from said co-transfected host cell, wherein the pair of said first and second plasmids is selected such that said rAAV vector is targeted for delivery to a specific tissue type. Any number of other approaches may also be used, as will be readily recognized by one of skill in the art.

An active fragment of OPN gene refers to a nucleotide sequence that encodes a fragment of OPN or an amino acid sequence that retains the same or substantially the same biological activity of OPN protein. In various embodiments, the OPN protein is loaded on the viral vector under the control of a promoter targeted to the brain.

Various embodiments of the present invention also provide for a method of elevating osteopontin (OPN) by delivering OPN to the brain of a subject using a liposome delivery system.

A liposomal delivery system is capable of entrapping both lipophilic and hydrophilic compounds which enables a diverse range of drugs to be encapsulated by the liposome.

The term "liposome", as used herein refers to a phospholipid vesicles consisting of one or more concentric lipid bilayers enclosing discrete aqueous spaces. The large aqueous center and biocompatible lipid exterior permits the delivery of a variety of macromolecules, such as DNA, proteins and imaging agents.

As a drug delivery system, liposomes offer several advantages including biocompatibility, capacity for self-assembly, ability to carry large drug payloads, and a wide range of physicochemical and biophysical properties that can be modified to control their biological characteristics. Encapsulation within liposomes protects compounds from early inactivation, degradation and dilution in the circulation.

Liposomes may be produced by a wide variety of methods. Methods of preparing liposome delivery systems are known. See for example in Gabizon et al., Cancer Research (1982) 42:4734; Cafiso, Biochem Biophys Acta (1981) 649:129; Szoka, Ann Rev Biophys Eng (1980) 9:467; U.S. Pat. No. 4,882,165, and Deamer and User, "Liposome Preparation: Methods and Mechanisms," in Liposomes, Marcel Dekkev, Inc., New York (1983).

Multilamellar vesicles (MLV) are formed by hydration of dry lipid powders. Ultrasonication with probe type sonicators or processing through a French press produces small, unilamellar vesicles (SUV). Extrusion techniques are the most widely used methods for SUV liposome production for in vitro and in vivo studies due to their ease of production, readily selectable particle diameters, batch-to-batch reproducibility, and freedom from solvent and/or surfactant contamination. Solvent injection and detergent dialysis techniques for liposome production give heterogeneous distributions of particle sizes and are not commonly used for biophysical or biochemical experimentation due to the retention of membrane impurities in these particles. Materials to be encapsulated may be passively entrapped or "remote" loaded.

Methods of loading drugs into liposomes are known in the art. See for example Ostro and Cullis, Am. J. Hosp. Pharm. 456:1567-1587 (1989) and Juliano, "Interactions of Proteins and Drugs with Liposomes," in Liposomes, Ibid. Most drugs are loaded at the time the liposome is formed by co-solubilizing the drug with the starting materials. The site of the liposome (cavity or membrane) into which the drug is located depends on the properties of the drug.

The liposomal delivery system can be utilized to deliver a variety of exogenous molecules to the cytoplasm of cells, including diagnostic agents, molecules capable of modulating or otherwise modifying cell function, and molecules for treatment of a disease. These agents/molecules can be entrapped by the liposome vesicles either by encapsulating water-soluble compounds in their aqueous cavities, or by carrying lipid soluble compounds within the membrane itself. Exogenous molecules can include, but are not limited to: peptides, oligopeptides, proteins, apoproteins, glycoproteins, antigens and antibodies thereto, receptors and other membrane proteins, protein analogs, enzymes, coenzymes, enzyme inhibitors, amino acids and their derivatives, hormones, lipids, and phospholipids. Other molecules include nucleotides; oligonucleotides; polynucleotides; and their art-recognized and biologically functional analogs and derivatives including, for example; methylated polynucleotides and nucleotide analogs having phosphorothioate linkages; plasmids, cosmids, artificial chromosomes, and other nucleic acid vectors.

In various embodiments, the agent/molecule is OPN, a functional/biologically active fragment thereof. In various embodiments, the agent/molecule is an Alzheimer's disease treatment. Alzheimer's therapeutics include, but are not limited to cholinesterase inhibitors, such as donepezil (Aricept), galantamine (Razadyne) and rivastigmine (Exelon); Memantine (Namenda); antidepressants and anti-anxiety medications such as, clonazepam (Klonopin) and lorazepam (Ativan). In yet other embodiments, the agent/molecule is the combination of an Alzheimer's treatment and OPN.

In various embodiments, OPN is encapsulated within liposomes to enhance its delivery to the brain of the subject. In various other embodiments, the delivery of liposomal OPN to the brain results in the treatment and/or the prevention or reduction of the likelihood of Alzheimer's disease in the subject.

Various embodiments of the present invention provide for a method of elevating osteopontin (OPN) by delivering OPN to the brain of a subject using a nanodrug delivery systems.

Nanodrug delivery systems are useful in the delivery to the brain of therapeutically active molecules across the blood-brain barrier to treat a subject in need thereof.

In various embodiments, the nanodrug delivery system includes recombinant OPN or a functional/biologically active fragment thereof. In various embodiments, the nanodrug delivery system is targeted to cross the blood brain barrier to reach the brain. In various other embodiments, the nanodrug delivery system is released in the brain at amyloid plaque sites in the brain.

Methods of nanodrug delivery include, but are not limited to the use of exosomes to deliver treatment, pro-drugs, peptide masking, receptor-mediated permabilitizer, or nanoparticles.

Exosomes can be modified to contain recombinant OPN or a functional/biologically active fragment thereof. In various embodiments, OPN is elevated in the brain of a subject by administering exosomes containing OPN. In some embodiments, the exosomes containing OPN are injected systemically (i.e., intravenously).

Pro-drugs are therapeutic molecules disguised with lipophilic molecules that allow it to cross through the blood-brain barrier. Once in the brain, the lipophilic molecules are removed by either enzyme degradation or some other mechanism to release the drug into its active form. In various embodiments an OPN pro-drug is used to elevate OPN expression in the brain of the subject in need thereof. In some embodiments, OPN is recombinant OPN or a functional/biologically active fragment thereof.

Peptide Masking is a way of masking the therapeutic molecule with a molecule that is more likely to pass through the blood-brain barrier. An example of a molecule more likely to pass through the blood-brain barrier includes but is not limited to, cholesteryl.

Receptor-mediated permabilitizers are drug compounds that increase the permeability of the blood-brain barrier making it easier to get a molecule to pass through it. In various embodiments, OPN is elevated in the brain by administering a receptor-mediated permabilizer to the subject in need thereof, thereby increasing permeability of the blood-brain barrier and allowing OPN in the brain.

Nanoparticles are particles bound to the therapeutic molecule that are capable of traversing the blood-brain barrier. There are various types of nanoparticles that can be used, which includes, but is not limited to lipid-based, cationic liposomes, solid lipids, nanoemulsions, polymer based, or a polymer branch nanoparticle. Common polymer materials include, but are not limited to, polybutyl cyanoacrylate (PBCA), poly(isohexyl cyanoacrylate) (PIHCA), polylactic acid (PLA), or polylactide-co-glycolide (PLGA)

In various embodiments, the nanoparticle is biodegradable. In various other embodiments, the nanoparticles can be coated to with surfactants to aid in crossing the blood-brain barrier. Examples of surfactants include, but are not limited to polysorbate 80, 20, 40, 60, and poloxamer 188. In some embodiments, the nanoparticles are targeted to the brain.

Improving Cognitive Function

Various embodiments of the present invention also provide for a method of improving cognitive function in a subject in need thereof, comprising: providing a composition that, when administered to the subject, results in increased levels of osteopontin (OPN) relative to a normal subject; and administering an amount of the composition to the subject sufficient to increase said levels of OPN.

In various embodiments, the composition comprises OPN expressing innate immune cells, recombinant OPN, OPN fragments, OPN derivatives, OPN mimetics, OPN analogues or a combination thereof.

In some embodiments, the composition stimulates expression of OPN in innate immune cells. In various other embodiments, the innate immune cells comprise monocytes, macrophages or combinations thereof. In other embodiments, the monocytes comprise bone marrow-derived monocytes, spleen-derived monocytes, CD115 positive monocytes (CD115+ monocytes) or combinations thereof. In yet other embodiments, the monocytes are infiltrating monocytes and become OPN expressing macrophages in the brain. In certain embodiments, the innate immune cells are phagocytic.

In various embodiments, the composition comprises glatiramer acetate (GA). In various other embodiments, the innate immune cells are stimulated ex vivo or in vivo.

In various embodiments, the innate immune cells expressing OPN are administered to the subject by adoptive cell transfer or bone marrow transplantation.

In various embodiments, the composition is administered by a method selected from the group consisting of direct delivery to the subject, viral vector delivery, a liposomal delivery system, or nanodrug delivery system.

In various embodiments, the symptom of Alzheimer's disease is selected from the group consisting of memory loss, decline in non-memory aspects of cognition, impaired reasoning or judgment, behavior changes, carry out multi-step tasks, hallucinations, delusions, paranoia and combinations thereof.

In various embodiments, the administration of the composition results in an increase in MMP-9. In various other embodiments, increased levels of OPN results in decreased levels of a misfolded protein in the subject, decreased inflammation in the subject, increased synaptic regeneration in the subject, recruitment of macrophages to an amyloid beta (Aβ) plaque site in the subject, or combinations thereof.

In other embodiments, wherein the misfolded protein is Aβ. In yet other embodiments, the Aβ is $A\beta_{40}$ and/or $A\beta_{42}$.

Various embodiments of the present invention also provide for a method of improving cognitive function in a subject in need thereof, comprising: providing a composition that, when administered to the subject, results in increased levels of osteopontin (OPN) relative to a normal subject; and administering an amount of the composition to the subject sufficient to increase said levels of OPN.

In various embodiments, the composition comprises OPN expressing innate immune cells.

In some embodiments, the composition stimulates expression of OPN in innate immune cells. In various other embodiments, the innate immune cells comprise monocytes, macrophages or combinations thereof. In other embodiments, the monocytes comprise bone marrow-derived monocytes, spleen-derived monocytes, CD115 positive monocytes (CD115+ monocytes) or combinations thereof. In yet other embodiments, the monocytes are infiltrating monocytes and become OPN expressing macrophages in the brain. In certain embodiments, the innate immune cells are phagocytic.

In various embodiments, the composition comprises glatiramer acetate (GA). In various other embodiments, the innate immune cells are stimulated ex vivo or in vivo.

In various embodiments, the innate immune cells expressing OPN are administered to the subject by adoptive cell transfer or bone marrow transplantation.

In various embodiments, the administration of the composition results in an increase in MMP-9. In various other embodiments, increased levels of OPN results in decreased levels of a misfolded protein in the subject, decreased inflammation in the subject, increased synaptic regeneration in the subject, recruitment of macrophages to an amyloid beta (Aβ) plaque site in the subject, or combinations thereof.

In other embodiments, wherein the misfolded protein is Aβ. In yet other embodiments, the Aβ is $A\beta_{40}$ and/or $A\beta_{42}$.

Various embodiments of the present invention also provide for a method of improving cognitive function in a subject in need thereof, comprising: providing a composition that, when administered to the subject, results in increased levels of osteopontin (OPN) relative to a normal subject; and administering an amount of the composition to the subject sufficient to increase said levels of OPN.

In various embodiments, the composition comprises recombinant OPN, OPN fragments, OPN derivatives, OPN mimetics, OPN analogues or a combination thereof.

In various embodiments, the composition is administered by a method selected from the group consisting of direct delivery to the subject, viral vector delivery, a liposomal delivery system, or nanodrug delivery system.

In various embodiments, the administration of the composition results in an increase in MMP-9. In various other embodiments, increased levels of OPN results in decreased levels of a misfolded protein in the subject, decreased inflammation in the subject, increased synaptic regeneration in the subject, recruitment of macrophages to an amyloid beta (Aβ) plaque site in the subject, or combinations thereof. In other embodiments, wherein the misfolded protein is Aβ. In yet other embodiments, the Aβ is $A\beta_{40}$ and/or $A\beta_{42}$.

Monocyte Enrichment

Various embodiments of the present invention provide for a method of monocyte enrichment, comprising: obtaining a blood sample from a subject, isolating the blood cells from the sample, and increasing OPN expression by stimulating the blood cells. In various embodiments, the blood cells isolated comprise monocytes. In other embodiments, monocytes are stimulated with glatiramer acetate (GA). In some other embodiments, monocytes are stimulated ex vivo.

In some embodiments, the monocytes are bone marrow-derived monocytes, spleen-derived monocytes, and/or CD115 positive monocytes (CD115+ monocytes). In other embodiments, the monocytes become OPN expressing macrophages in the brain.

In various embodiments, the method further comprises administering the enriched monocytes to a subject in need thereof. In various embodiments, the monocytes are administered via adoptive cell transfer or bone marrow transplant. GA can be administered before, substantially with, and/or after the adoptive cell transfer or bone marrow transfer.

MMPs

As discussed herein, OPN is a known substrate for MMPs (including MMP-9). MMP-9 is a scar tissue and Aβ-degrading enzyme. OPN is known to make the immune cells more phagocytic, while MMP-9 is a protease that cleaves OPN and enhances degradation of Aβ. The administration of GA results in the increase of OPN (full-length OPN and its MMP-cleaved fragments) and MMP-9 and results in Aβ degradation.

Various embodiments of the present invention provide for a method, comprising stimulating innate immune cells in a subject in need thereof.

In various embodiments, the innate immune cells are stimulated with glatiramer acetate (GA). In some embodiments, the innate immune cells are stimulated ex vivo or in vivo.

In various embodiments, OPN is increased upon stimulation with GA. In various embodiments, MMP-9 is increased upon stimulation with GA. In various embodiments, OPN and MMP-9 are increased upon stimulation with GA.

In various embodiments, the innate immune cells comprise monocytes, macrophages or combinations thereof. In some embodiments, the monocytes comprise bone marrow-derived monocytes, spleen-derived monocytes, CD115 positive monocytes (CD115$^+$ monocytes) or combinations thereof. In other embodiments, the monocytes are infiltrating monocytes and become OPN expressing macrophages in the brain.

In various embodiments, the subject has Alzheimer's disease.

In various embodiments, the method further comprising treating the subject in need thereof. In various embodiments, an increase in OPN and/or MMP-9 results in the degradation of amyloid plaques in the subject.

Dosage and Administration

The compositions of the invention, as described herein are useful in a variety of applications including, but not limited to, methods of elevating OPN in the brain and therapeutic treatment methods, such as the treatment of Alzheimer's disease. The methods of use may be in vitro, ex vivo, or in vivo methods.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral.

"Transdermal" administration may be accomplished using a topical cream or ointment or by means of a transdermal patch.

"Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

Via the ocular route, they may be in the form of eye drops.

In various embodiments, an agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. In particular embodiments, compounds used herein are administered orally, intravenously or intramuscularly to a patient having Alzheimer's disease.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

In various embodiments, the present invention provides pharmaceutical compositions including a pharmaceutically acceptable excipient along with a therapeutically effective amount of OPN. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. The active ingredient can be mixed with excipients which are pharmaceutically acceptable and compatible with the active ingredient and in amounts suitable for use in the therapeutic methods described herein. Such excipients may be solid, liquid, semisolid, or, in the case of an aerosol composition, gaseous. Suitable excipients are, for example, starch, glucose, lactose, sucrose, gelatin, malt, rice, flour, chalk, silica gel, sodium stearate, glycerol monostearate, talc, sodium chloride, dried skim milk, water, saline, dextrose, propylene glycol, glycerol, ethanol, mannitol, polysorbate or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts. Pharmaceutically acceptable salts include the acid addition salts formed with inorganic acids such as, for example, hydrochloric or phosphoric acids, organic acids, for example, acetic, tartaric or mandelic, salts formed from inorganic bases such as, for example, sodium, potassium, ammonium, calcium or ferric hydroxides, and salts formed from organic bases such as isopropylamine, trimethylamine, 2-ethylamino ethanol, histidine, procaine and the like. Liquid compositions can contain liquid phases in addition to and in the exclusion of water, for example, glycerin, vegetable oils such as cottonseed oil, and water-oil emulsions. Physiologically tolerable carriers are well known in the art. The amount of an active agent used in the invention that will be effective in the treatment of a particular disorder or condition will depend on the nature of the disorder or condition, and can be determined by one of skill in the art with standard clinical techniques.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages can be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biological samples obtained, or the responses observed in the appropriate animal models.

For the treatment of the disease, the appropriate dosage depends on the type of disease to be treated, the severity and course of the disease, the responsiveness of the disease, whether the antibody is administered for therapeutic or preventative purposes, previous therapy, and patient's clinical history. The dosage can also be adjusted by the individual physician in the event of any complication and at the discretion of the treating physician. The administering physician can determine optimum dosages, dosing methodologies and repetition rates. The pharmaceutical composition can be administered one time or over a series of treatments lasting from several days to several months, or until a cure is effected or a diminution of the disease state is achieved (e.g., treatment or amelioration of Alzheimer's Disease). The duration of treatment depends upon the subject's clinical progress and responsiveness to therapy. In certain embodiments, dosage is from 0.01 µg to 100 mg per kg of body weight, and can be given once or more daily, weekly, monthly or yearly.

In various embodiments, a therapeutically effective amount of recombinant OPN is administered to the subject by any appropriate technique, as will be readily appreciated by those of skill in the art. In some embodiments, the recombinant OPN is administered via the nasal, parenteral or ocular route. In some embodiments, the parental route is an intravenous injection. In various embodiments, the ocular route is via eye drops.

In various embodiments, an OPN viral vector may be administered by any appropriate technique, as will be readily appreciated by those of skill in the art. In various embodiments, administering the composition comprises administering by intravenous injection. In various embodiments, the composition is administered by intramuscular injection. In various embodiments, the composition is administered nasally. These methods result in the delivery of the OPN gene or a gene encoding an active fragment of OPN to brain tissue. These methods also result in secretion of OPN or an active fragment thereof directly into the circulation. The AAV vector, AAV helper construct and the helper virus or accessory function vector(s) can be introduced into the host cell either simultaneously or serially, using standard transfection techniques. Further, the viral vector can be delivered as a single administration or as a treatment regimen, e.g., daily, weekly, or at any other suitable time interval, as will be readily recognized by one of skill in the art. The dosage depends on various factors such as the age, weight, severity of vascular condition, and other factors a doctor might identify.

In various embodiments, the liposome is modified to comprise OPN or a functional/biologically active OPN fragment. In some embodiments, the modified liposome may be administered by any appropriate technique, as will be readily appreciated by those of skill in the art. In various embodiments, the modified liposome is administered via a peripheral injection to the blood. In various other embodiments, the modified liposome is administered orally.

In various embodiments, the copolymer GA is administered to enhance natural recruitment of blood-borne monocytes. In various embodiments, the blood-borne monocytes are recruited and infiltrate the diseased brain parenchyma. In other embodiments, the infiltrating monocytes become macrophages.

In some embodiments, the copolymer GA is administered weekly. In various embodiments, the copolymer is administered for up to 10 weeks. In various embodiments, the dosage of GA administered can be in a range of about 10-150 µg. In some embodiments, the dosage of GA ranges from about 10-20 µg, 20-30 µg, 30-40 µg, 40-50 µg, 50-60 µg, 60-70 µg, 70-80 µg, 80-90 µg, 90-100 µg, 100-110 µg, 110-120 µg, 120-130 µg, 130-140 µg or 140-150 µg. In some embodiments, the GA dosage is 100 µg. In yet other embodiments, the dosage is 30 µg.

In various embodiments, GA is administered for a 6-48 hour exposure. In some embodiments, GA exposure is for 6-12 hours, 12-24 hours, 24-36 hours, or 36-48 hours. In other embodiments, GA exposure is for 12-24 hours.

In various other embodiments, a subset of bone marrow-derived $CD115^+$ monocytes are administered. In some embodiments, the bone marrow-derived $CD115^+$ monocytes are administered monthly. In some embodiments, the peripheral blood is enriched with bone marrow-derived $CD115^+$ monocytes. In various embodiments, the administration of bone marrow-derived $CD115^+$ monocytes increases cerebral recruitment of monocyte-derived macrophages.

In yet other embodiments, the copolymer GA and a subset of bone marrow-derived $CD115^+$ monocytes is administered. In other embodiments, the combined administration results in greater monocyte recruitment in the subject.

In various embodiments, the administration of the copolymer GA and/or a subset of bone marrow-derived $CD115^+$ monocytes results in retention of cognitive function, synaptic preservation, plaque removal, restriction of astrogliosis, and modulation of the immune molecular milieu. One of skill in the art can determine the appropriate amount of innate immune cells to be administered to a subject in need thereof.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Mice

Alzheimer's disease double transgenic APPK595N, M596L+PS1$_{ΔE9}$, APP/PS1 (ADtg) mice from the B6.Cg-Tg (APPswe, PSEN1E9) 85 Dbo/J strain and their age-matched non-transgenic (wild-type) litter-mates were purchased from Jackson Laboratories (Stock #005864) and then bred and maintained at Cedars-Sinai Medical Center. These ADtg mice carry the human transgene, which allows detection of amyloid-β forms using anti-human antibodies. All mice in this study have a C57BL/6 congenic back-ground. Two cohorts of mice (all male) were used for behavioral, histological, and biochemical analysis. An additional ADtg mouse cohort (equal numbers male and female) was used to evaluate innate immune infiltration to the brain by flow cytometry. For in vitro studies, primary cell cultures, and characterization of isolated CD115+ monocytes before and after magnetic-activated cell sorting (MACS) column selection, the bone marrow donor mice were young non-transgenic wild-type litter-mates (8-10 weeks of age). For adoptive transfer of bone marrow-derived monocytes, the donor mice were young (8-10 weeks of age) C57BL/6-transgenic (UBC-GFP) 30 Scha/J mice expressing enhanced green fluorescent protein (GFP) under the direction of the human ubiquitin C promoter (Stock #004353). For flow cytometry studies assessing monocyte infiltration into ADtg brains, the donors were young non-transgenic wild-type mice (8-10 weeks of age). All experiments were conducted according to regulations of the Cedars-Sinai Medical Center Institutional Animal Care and Use Committee (IACUC) under an approved protocol. In addition, all experiments were conducted and recorded by researchers blinded to the mouse genotypes.

Genotyping

Genomic DNA was extracted from the tip of the mouse tail by using a DNA extraction kit (Qiagen) and following the manufacturer's protocol. Double-transgenic $APP_{SWE}/PS1_{AE9}$ mice and non-transgenic wild-type littermates were identified by genotyping for the presence of the transgenes by PCR, as previously described (Jankowsky et al., Biomol Eng 2001; 17: 157-65, Jankowsky et al., Hum Mol Genet 2004; 13: 159-70.; Butovsky et al., Proceedings of the National Academy of Sciences of the United States of America 2006 103:11784-11789).

Glatiramer Acetate Immunization

ADtg mice (10 months old) received subcutaneous injections of GA [also known as Cop-1 and Copaxone®; 100 μg in phosphate-buffered saline (PBS)] or PBS alone (control group) twice a week for 1 week and then once a week for 8 weeks. For evaluation of innate immune infiltration to the brain by flow cytometry, 10-month-old ADtg mice received subcutaneous injections of GA (100 mg in PBS) or PBS alone twice a week for 1 week and then once a week for 3 weeks. At the end of the study, all mice were anaesthetized and then perfused with ice-cold PBS with 0.5 mM EDTA, after which their organs were collected and analyzed or fixed in 2.5% paraformaldehyde (Sigma-Aldrich), and cryoprotected with 30% sucrose for further histological analysis.

Isolation and Adoptive Transfer of Bone Marrow-Derived CD115+ Monocytes $CD115^+$ monocytes from mice donors were isolated as previously reported (Koronyo et al., Brain: a journal of neurology 2015, 138:2399-2422). In brief, bone marrow cells were harvested from the femora, tibiae, and humeri and enriched for mononuclear cells on a Ficoll-Paque® PLUS (17-1440-03, GE Healthcare) density gradient. The $CD115^+$ monocyte population was isolated through MACS enrichment column using the biotinylated anti-CD115 mAb clone AFS98 (#13-1152; eBioscience) and streptavidin-coupled magnetic beads (Miltenyi Biotec), according to the manufacturer's protocols. After this procedure, monocytes (5-6×$10^6$ cells/mouse) were injected into the tail veins of 10-month-old ADtg mice once a month for 2 months. For evaluation of innate immune infiltration to the brain by flow cytometry, 10-month-old ADtg mice received one injection of bone marrow-derived CD115+ monocytes (same dose as above).

Flow Cytometry and Immunohistochemical Characterization of Bone Marrow-Derived $CD115^+$ Monocytes Bone marrow cells were harvested from young donor wild-type mice (n=3-4 mice per experiment) as detailed above. After enrichment for mononuclear cells by Ficoll® gradient, one portion of cells was collected (before $CD115^+$ column), and a second portion of cells underwent further isolation for $CD115^+$ monocyte population (after $CD115^+$ column), using the MACS enrichment column as detailed above. Both cell portions, before and after CD115+ column, were either immediately stained and analyzed by flow cytometry or plated to generate macrophage cultures for further immunohistochemical analysis. For flow cytometry analysis, the before $CD115^+$ column cells were stained with the following antibodies: biotinylated anti-CD115 mAb clone AFS98 (#13-1152; eBioscience), APC-conjugated anti-Biotin clone Bio3-18E7 (#130-090-856; Miltenyi Biotec), PE-conjugated anti-CD36 clone REA262 (#130-102-763; Miltenyi Biotec), Viobright FITC-conjugated anti-CD36 clone REA262 (#130-104-889; Miltenyi Biotec), PE-conjugated anti-CD204 clone REA148 (#130-102-328; Miltenyi Biotec), and Alexa Fluor® 488-conjugated anti-MMP9 poly-clonal antibody (#bs-0397R-A488; Bioss). For the after $CD115^+$ column cells, we used a set of staining antibodies identical to that specified above but excluded the primary anti-CD115 mAb because this isolation procedure already linked the biotinylated anti-CD115 antibody to the cells. All antibody dilutions were 1:100. The labeled samples were analyzed on a BD LSRFortessa™ Cell Analyzer equipped with BD FACS Diva software; data were further analyzed with FlowJo software (vX.0.7r2; Tree Star, Inc.).

Both cell portions, before and after CD115+ column selection, were also differentiated into primary macrophage cultures and analyzed by immunohistochemistry. In brief, cells were differentiated into macrophages by 7-day cultivation in complete RPMI-1640 medium (#21870; Life Technologies) with 10% serum and 20 ng/ml MCSF (#315-02; PeproTech). Primary cultures of macrophage were then plated at 1.2×$10^5$ cells per well (3-4 wells for each condition) in 24-well tissue-culture plates on glass coverslips overnight. Methanol (99.8%) at −20° C. for 20 min was used for fixation of the cells followed by repeated washes with PBS. Cells were then stained using rat anti-CD36 mAb clone MF3 (1:200; ab80080; Abcam), rat anti-CD204 scavenger receptor type I/II (SCARA1) mAb (1:100; MCA1322; AbD Serotec), and goat anti-MMP9 pAb (1:100; AF909; R&D systems). Secondary polyclonal antibodies included donkey anti-rat and anti-goat conjugated with Cy2, Cy3 or Cy5 (1:200; Jackson ImmunoResearch Laboratories). The cells were mounted using ProLong® Gold with DAPI (Molecular Probes, Life Technologies). Several fields (minimum n=4 randomly selected per group) were obtained from each well using a Carl Zeiss Axio Imager Z1 Apotome-equipped microscope (an average of 120 cells in each field). Images were obtained using the same exposure time in each occasion. The fluorescent signal and its total area were determined and quantified by the conversion of the individual images to grey scale and standardizing to base-line using histogram-based thresholds with NIH ImageJ software. The 'area/cell' measures the total fluorescent signal (area) divided by the total number of cells (DAPI count) of the same field (image). For all experiments, the investigators were blinded to the treatment condition.

Barnes Maze Behavioral Test in Mice

The Barnes maze is a spatial-learning task that allows subjects to use spatial cues to locate a means of escape from a mildly aversive environment (open space with light projection); mice are required to use spatial cues to find an escape location. The mice are assessed for their ability to learn the location of an escape box over the course of 9 days in the Barnes maze apparatus. This timing was established based on significant differences between wild-type and PBS groups, and was found suitable to test the effects of our treatments. The Barnes maze apparatus is a circular table in which 20 holes are located equidistantly around the perimeter. During a trial the escape box is placed under one of these holes, whereas false boxes, too small to be entered, are placed beneath the other 19 holes. The animals are first placed into an opaque cylinder at the center of the maze for 30 s to promote initial spatial disorientation. After this time, the cylinder is removed and the animal explores the maze until it finds and enters the escape box, leading to its return to the home cage. The escape latency is the duration of time between removal of the cylinder and the animal's entry into the escape box. The errors (incorrect entries) represent the number of events in which the mouse enters a false box. Two bright lights illuminate the center of the Barnes platform. If the mouse fails to enter the escape box within 5 min (300 s), the experimenter leads it to the escape box. The animal remains in the escape box for an additional 30 s before it is removed and taken to the home cage. All boxes and the maze surface are sprayed with 70% isopropyl alcohol and wiped in a non-systematic fashion to dissipate odor cues for the subsequent trial. The location of the escape box remains the same during every trial of the training/acquisition phase and is shifted between mice to reduce the potential for unintended intra-maze cues. Training is repeated three times per day with a 15-min interval separating each trial. Data from each trial are retained and averaged. The training/acquisition phase is 4 days. Following this is a 2-day break without any exposure to the maze. On Day 7, each animal is retested during a three-trial session by using the same escape box location and method from the training/acquisition phase. On Day 8, following the memory retention phase, the reversal phase begins. The escape box is placed in a quadrant different from the original escape box location. Using the same procedure detailed above, reversal trials are repeated three times per day over two consecutive days (Days 8 and 9). The second cohort of mice underwent the same Barnes maze test, except that each session time was shortened to a maximum of 4 min (240 s), as this length of time was shown to be as effective as the longer period (5 min). All investigators were blinded to the mouse groups. Data were recorded manually, digitally, and by a video camera located above the maze.

Immunohistochemistry

Brain coronal cryosections (30-µm thick) were treated for 30 minutes in antigen-retrieval solution (DAKO) prior to application of serum-free protein block (Dako Cytomation or with a permeabilization blocking solution containing 20% normal horse serum (Invitrogen) and 0.05% Triton™ X-100 (Sigma-Aldrich). Sections were then hybridized and stained overnight at 4° C. with combinations of the following primary antibodies in 2% blocking solution in PBS, including goat polyclonal OPN (R&D systems), mouse anti-human amyloid-β [residues 17-24, mAb clone 4G8 (1:100; SIG-39220; Covance) and residues 1-16, mAb clone 6E10 (1:100; SIG-39320; Covance)], rabbit anti-GFAP pAb (1:100; G926; Sigma-Aldrich), rabbit anti-Iba1 pAb (1:250; #019-19741; Wako Chemicals), rabbit anti-GFP pAb (1:500; #598; MBL), rat anti-CD68 (1:100; Abcam), rabbit anti-iNOS (1:100; Cell signaling), rat anti-CD45 mAb clone 30-F11 (1:25; #550539; BD Pharmingen), goat anti-IL10 pAb (1:100; AF519; R&D systems), and goat anti-MMP9 pAb (1:100; AF909; R&D systems). Hybridization with primary antibodies was followed by incubation with appropriate horseradish peroxidase (HRP)- or fluorophore-conjugated secondary antibodies (donkey anti-mouse, anti-rat, anti-goat, and anti-rabbit; 1:200; Jackson ImmunoResearch Laboratories) conjugated with Cy2, Cy3, Cy5, or DyLight™ 649, were incubated for 1 hour at 37° C. The sections were washed in PBS and mounted using Vectashield (Vector Laboratories) containing 4',6-diamidino-2-phenylindole dihydrochloride (DAPI) (H-1200) or not containing DAPI (H-1000), or ProLong® Gold with DAPI (Molecular Probes, Life Technologies). Negative controls were processed using the same protocol with the omission of the primary antibody to assess non-specific labeling. For microscopic analysis, we used a Carl Zeiss Axio Imager Z1 fluorescence microscope equipped with ApoTome (Carl Zeiss MicroImaging, Inc.). For processing and analysis of the images, we used Axio-Vision (release 4.6.3) software (Carl Zeiss).

Presynaptic Labeling and Quantification of Synaptic Area in the Hippocampus

To define the synaptic area in the hippocampus of ADtg and non-transgenic (wild-type) mice, three independent coronal brain sections at bregma −2.50, −2.65, and −2.80 mm (Liang et al., 2011) per animal (n=6 mice per group) were stained with the presynaptic marker VGluT1 (encoded by Slc17a7) (Chemicon, guinea pig, 1:6000). For each hippocampal field, high-resolution scans were acquired using×100 oil objective lens and the Zeiss ApoTom mode. Optical sectioning included 15 Z-stack images, each 0.25-mm wide and covering focal planes within a tissue depth of 3.75 mm. Sections from all five groups, obtained at the same level, were identically immunostained. During all experiments, no-primary and no-secondary antibody controls were run in parallel. There was no specific staining with these controls. To cover the hippocampal area, 15 rectangle fields (each 90 µm×70 µm) were precisely selected in the lateral and medial blade molecular layer of the dentate gyrus, as well as in the stratum lacunosummoleculare, stratum radiatum, and stratum oriens of the cornu ammonis 1(CA1). The parameters for scanning remained the same across treatment conditions. Single optical section images were analyzed using the NIH ImageJ macro and batch process to quantify the synaptic area (15 optical sections/field, 15 fields/brain section, and 675 total images/brain). The average synaptic area or percentage of the area per image was calculated for each condition.

Thioflavin-S Amyloid-β Plaque Staining

Following secondary antibody staining, the brain sections were stained with thioflavin-S (Thio-S, 1% w/v in 70% ethanol) (Sigma-Aldrich) for 10 min at room temperature, washed three times in 70% ethanol, and then washed once in distilled water, for 1 min each.

Quantification and Stereological Counting Procedure

The number and area (µm$^2$) of OPN+ cells, Iba1$^+$ CD45$^{hi}$ cells, GFAP$^+$ cells, Thio-S$^+$ amyloid-β plaques and 4G8$^+$ amyloid-β plaques were determined by examining four to six coronal sections per mouse at 150-µm intervals over an area covering both the hippocampal and cortical (including entorhinal and cingulate cortex) regions. For Iba1$^+$/CD45" quantification we selected only Iba1$^+$ cells labeled intensely with CD45 antibody, while excluding Iba1$^-$ cells. The CD45$^+$ cells (out of Iba1$^+$ cells) were converted into grey-scale images, and a threshold for intense/high signal was determined in ImageJ software once and applied to all images for CD45$^{high}$ quantification. The fluorescence of specific signals was captured using the same exposure time for each image. Images were converted to grey-scale, digitalized to PC, and standardized to baseline using histogram-based thresholds with NIH ImageJ software (versions 1.38x and 1.46r). In addition, manual counting of OPN$^+$/CD45$^{hi}$ cells, Iba1$^+$/CD45$^{hi}$ cells, GFAP$^+$ cells, and amyloid-β plaques was done with the aid of ImageJ software using the 'analyze' grid. Analyzers were blinded to the mouse groups performed all counts.

Flow Cytometry Analysis of Cerebral Monocyte Infiltration

Experimental ADtg mice (n=4-6 mice/group) were perfused with cold saline supplemented with 0.5 mM EDTA (pH8.0, Invitrogen) before harvest. Whole brains were then mechanically minced in a 70-mm cell strainer (Falcon; Corning Inc.) with ice-cold 2% fetal bovine serum (Atlanta Biological) in PBS. After centrifugation, homogenization and washing, the pellet was suspended in 40% sterile Percoll (GE Healthcare) and centrifuged for 25 min at 850 g. The cell pellet was resuspended in 70% Percoll and centrifuged for another 20 min at 800 g. Cells located in the top layer after the Percoll gradient were collected and washed. Next, cells were stained with the following antibodies purchased from Biolegend: FITC-conjugated anti-CD11b clone M1/70 (1:100, #101206); PE-conjugated anti-Ly-6C clone HK1.4 (1:100, #128007); and PE/Cy7-conjugated anti-CD45.2 clone 104 (1:100, #109830). The stained samples were analyzed on a BD LSRFortessa Cell Analyzer equipped with BD FACS Diva software, and data were further analyzed with FlowJo software (vX.0.7r2; Tree Star, Inc.).

Biochemical Determination of Amyloid-$\beta_{1-40}$, Amyloid-$\beta_{1-42}$, MCP1, IL10 and MMP9 Levels by Sandwich ELISA For brain soluble and insoluble ELISA analyses, brain tissues were thoroughly homogenized (Argos homogenizer) in PBS buffer with 0.5% Triton™ X-100 (T8787; Sigma) and protease inhibitor cocktail set I (#539131; Calbiochem). After removal of cell debris, the homogenate was centrifuged at 10,000 g for 25 min at 4° C. The supernatant was considered the 'soluble' fraction and was used to assess soluble amyloid-$\beta_{1-40}$, amyloid-$\beta_{1-42}$, MCP1 (encoded by Ccl2), IL10, and MMP9 levels. The pellet was then diluted and homogenized with the above homogenizing buffer. This was the 'insoluble' fraction and was used to assess insoluble amyloid-$\beta_{1-40}$ and amyloid-$\beta_{1-42}$.

For M$\Phi^{BM}$ cells, the cells in each well were lifted by 2 mM EDTA-PBS, collected in tubes, and centrifuged. Cell pellets were lysed and re-suspended in a cocktail of RIPA buffer supplemented with 1% protease inhibitors (Thermo Scientific), and stored at −80° C. until use.

After determination of protein concentration using the Pierce BCA Protein Assay Kit (#23227; Thermo Scientific), soluble and insoluble transgenic-derived amyloid-42 and amyloid-$\beta_{1-40}$ levels, and OPN were analyzed with an anti-human amyloid-$O_{1-42}$ end-specific sandwich ELISA kit (KHB3442, Invitrogen; which does not recognize mouse amyloid-$\beta$ nor human amyloid-$\beta$40/amyloid-$\beta$43), an anti-human amyloid-$\beta_{1-40}$ end-specific sandwich ELISA kit (KHB3482, Invitrogen; which does not recognize mouse amyloid-$\beta$ nor human amyloid-$\beta_{42}$/amyloid-$\beta_{43}$) and an anti-mouse OPN quantikine ELISA kit (R&D Systems), were used according to the manufacturer's instructions.

The amyloid-$\beta$ kits use a combination of two antibodies specific for the N- and the COOH-termini of amyloid-$\beta_{1-42}$ or amyloid-$\beta_{1-40}$ sequences. The bound rabbit anti-COOH-terminus was detected through the use of a horseradish peroxidase-labeled anti-rabbit anti-body and was read at 450 nm using a microplate reader (Spectra Max 384 plus, Molecular Devices). Soluble MCP1, IL10, and MMP9 levels were measured using the mouse/rat CCL2/JE/MCP1 Quantikine® ELISA Kit (MJE00), Mouse IL10 Quantikine® ELISA Kit (M1000B), and Mouse Total MMP-9 Quantikine® ELISA Kit (MMPT90), respectively, all according to the manufacturer's instructions (R&D systems). The optical density of each well was read at 450 nm (with 540 nm correction) using the same microplate reader (Spectra Max 384 plus, Molecular Devices).

Preparation of Amyloid-$\beta_{1-42}$ Fibrils

Lyophilized non-fluoro amyloid-$\beta_{1-42}$ peptide (#20276; Anaspec) was initially monomerized by dissolving it in ice-cold HFIP (hexafluoroisopropanol) (#52512; Sigma) to a final concentration of 1 mM and then aliquoted in sterile siliconized microcentrifuge tubes. The HFIP was first evaporated while in the sterile hood and then under vacuum conditions in a SpeedVac for 2 h to remove any trace of HFIP; the peptide film was stored at −20° C. until use. To induce fibril formation, fluoro (HiLyte647; #64161; Anaspec) and non-fluoro amyloid-$\beta_{1-42}$ films were resuspended in media to which 10% of sterile NaOH 60 mM was first added and the media were vortexed for 30 s. Then, a sterile 45% H$_2$O and a sterile 45% solution of 20 mM NaH$_2$PO$_4$+Na$_2$HPO$_4$ (pH 7.4) were added, and the media were vortexed again and incubated on a shaker for 2 weeks at 37° C. Pre-formed amyloid-$\beta_{1-42}$ fibrils were then sonicated for 60 s and diluted to 100 nM using the same media prior to the phagocytosis assay.

Primary Cultures of Bone Marrow-Derived Macrophage and the Phagocytosis Assay

To test amyloid-$\beta$ phagocytosis by macrophage, in repeated experiments monocytes were isolated from the bone marrow of wild-type mice (n=18 mice) and differentiated into macro-phage by 7-day cultivation in complete RPMI-1640 medium (#21870; Life Technologies) with 10% serum and 20 ng/ml MCSF (#315-02; PeproTech). Bone marrow-derived macrophages (M$\Phi$BM) were generated from femurs and tibiae cultured for 6-7 days in complete RPMI 1640 medium (Life Technologies) with 10% FBS, 100 U/ml penicillin, 100 µg/ml streptomycin, 2 mM L-glutamine and 20 ng/ml MCSF (PeproTech). Primary cultures of macrophage were then plated at 1.2×10$^5$ cells per well (3-4 wells for each condition) in 24-well tissue-culture plates on glass cover-slips overnight. Next, macrophages were either treated with 30 µg/ml GA (Copaxone®; TEVA Neuroscience), Brefeldin A (BFA; Sigma, 1×), or 10 µM Minocycline (Sigma) for the duration of 1, 3, or 24 h, or not treated (control group). Before addition of fibrillar amyloid-$\beta_{1-42}$, the cells were chilled in a 4° C. ice bath for 5 min; immediately after addition of the preformed fibrillar amyloid-$\beta_{1-42}$ (100 nM), the plates were centrifuged at 515 g in 25° C. followed by incubation at 37° C. for 30 or 60 min. The cells were then rinsed with amyloid-$\beta$-free medium to remove non-incorporated amyloid-$\beta$ and later washed twice with PBS. Methanol (99.8%) at −20° C. for 20 min or 4% paraformaldehyde at room temperature for 12 min was used for fixation of the cells followed by repeated washes with PBS. For immunostaining, the cells were first stained using the mouse anti-human amyloid-$\beta$ mAb clone 6E10 (1:100; SIG-39320; Covance), rat anti-CD68 mAb clone FA-11 (1:100; ab53444; Abcam), rat anti-CD36 mAb clone MF3 (1:200; ab80080; Abcam), rat anti-CD204 scavenger receptor type I/II (SCARA1) mAb (1:100; MCA1322; AbD Serotec), rabbit anti-CD163 pAb (1:100; orb13303; Biorbyt), and goat anti-MMP-9 pAb (1:100; AF909; R&D systems). Secondary polyclonal antibodies included donkey anti-mouse, anti-rat, anti-rabbit, and anti-goat conjugated with Cy2, Cy3 or Cy5 (1:200; Jackson ImmunoResearch Laboratories). The cells were mounted using ProLong® Gold with DAPI (Molecular Probes, Life Technologies). Several fields (minimum n=5 randomly selected per group) were obtained from each well using a Carl Zeiss Axio Imager Z1 ApoTome-equipped microscope (an average of 120 cells in each field). Images were obtained using the same exposure time in each occasion. The fluorescent signal and its total area were determined and quantified by the conversion of individual images to greyscale and standardizing to baseline using histogram-based thresholds with NIH ImageJ software. The 'mean area per cell' was a result of a numerical average of the individual cell's immunoreactive area per field. The 'area/cell' measures the total fluorescent signal (area) divided by the total number of cells (DAPI count) of the same field (image). For all experiments, the investigators were blinded to the treatment condition.

Western Blotting

MΦ$^{BM}$ were lifted from each cell by 2 mM EDTA-PBS, collected in an Eppendorf tube, and centrifuged. Cell pellets were lysed in RIPA buffer (Thermo Scientific) and supplemented with a cocktail of protease inhibitors (Thermo Scientific). Protein concentration was determined using a BCA Protein Assay Kit (Thermo Scientific). Aliquots of protein samples were electrophoretically separated using 4-12% Bis-Tris gels (Invitrogen), then transferred to nitrocellulose membranes, blocked in Tris-buffered saline (TBS) containing 5% (w/v) non-fat dry milk, and hybridized with appropriate primary antibodies, including rabbit polyclonal OPN (Abcam), goat polyclonal OPN (R&D systems), and Actin (Abcam). Membranes were then incubated with the appropriate HRP-conjugated secondary antibody prior to development with chemiluminescent substrates. Densitometric analysis of blots was conducted using ImageJ software, and each experimental sample was normalized to Actin.

OPN Knockout by siRNA In Vitro

A set of three Stealth OPN siRNAs made up of 25-bp duplex oligoribonucleotides each were used with sequences corresponding to the sense and antisense strands of OPN (Invitrogen). Equal amounts (100 nM each) of siRNAs were mixed and diluted in OptiMEM (Gibco) to finalconcentration of 100 nmol/L, then transiently transfected into MΦ$^{BM}$ using Lipofectamine® RNAiMAX Transfection Reagent (Invitrogen), per manufacturer's protocol. Control macrophages were transfected with Stealth RNAi™ siRNA Negative Control. MΦ$^{BM}$ were incubated for 48 hours after transfection, and were used for subsequent experiments.

Cell Length Measurement

The long and short axes of cells were manually measured in μm from microscopic images (McWhorter et al., Proceedings of the National Academy of Sciences of the U.S. Pat. No. 2,013,110: 17253-17258) using length tools in the Axiovision Rel. 4.8 software package. At least 100 cells were examined in each experiment where individual cells were assayed by microscopy.

Statistical Analysis

GraphPad Prism 6.01 (GraphPad Software) was used to analyze the data. A comparison of two or more groups during several days (Barnes maze test) was performed using a two-way ANOVA followed by the Bonferroni multiple comparison post-test of paired groups. A comparison of three or more groups was performed using a one-way ANOVA followed by the Tukey or Bonferroni multiple comparison test of paired groups. Two-group comparisons were analyzed using a two-tailed unpaired Student t-test. StatPlus paired t-tests and one-way ANOVA with Tukey post hoc comparisons were conducted for quantification of the synaptic area. Correlation analysis was performed using Prism Pearson's tests. Results are expressed as means±standard deviations (SDs) or means±standard errors of the mean (SEMs) as indicated. A P-value<0.05 was considered significant. Degree of significance between groups is represented as follows: *p<0.05, p<0.001, *p<0.0001, and ****p<0.00001. A p-value lower than 0.05 was considered significant. All data analyses were led by blind examiner; code was revealed when analyses were concluded.

Example 1

The inventors investigated if and how immune modulation, achieved through glatiramer acetate (GA) or grafting of BM-CD115$^+$ monocytes (Mo), can preserve synaptic and neuritic formation and cognitive function in Alzheimer's disease (AD) murine models. AD neuropathology is tightly associated with increased amyloid β-protein (Aβ), especially highly synaptotoxic Aβ$_{1-42}$ alloforms, thought to elicit cognitive decline. GA treatment of bone marrow (BM)-derived MΦ in primary cultures substantially enhanced phagocytosis and degradation of fAβ$_{1-42}$ through upregulation of scavenger receptors and Aβ-degrading enzymes. Nonfibrillar Aβ forms, mainly oligomeric (o) Aβ$_{1-42}$, believed to be the most neurotoxic species was examined. However, their effects on cells remain largely unknown due to their highly metastable nature and existence in dynamically changing mixtures. To overcome these difficulties, technique have been pioneered to prepare stable populations of structurally characterized oligomers of specific size (number of monomers), as well as pure protofibrillar and fibrillar species. This uniquely allows us to determine the impact of nonfibrillar Aβ$_{1-42}$ assemblies on synaptic and neuritic integrity and neuronal function, and to explore the capacity of Mo/MΦ to eliminate such assemblies from the brain. Without being bound to any particular theory, the data in AD$^+$ mice suggests that accumulation of cerebral Aβ$_{1-42}$ is accompanied by synaptic loss and cognitive decline. GA or grafted Mo resulted in preservation of synapses associated with retained cognition. The studies also indicate preservation of synaptic density and neuritic length by GA-treated MΦ in primary co-cultures of MΦ and neurons in response to structurally stable and defined f/oAβ$_{1-42}$. The inventors identified upregulation of the immune modulator osteopontin (OPN) in GA-treated MΦ to be associated with increased fAβ$_{1-42}$ phagocytosis; OPN inhibition appears to impair phagocytosis. While not wishing to be bound by any particular theory, we believe that preservation of synapses and neuronal activity can be enhanced by brain-infiltrating Mo/MΦ (induced by GA or grafted Mo) that eliminate pathogenic Aβ species, regulate detrimental inflammation, and secrete neurotrophic factors.

Herein, the inventors study preservation of synaptic structure and function by GA-treated MΦ in primary co-cultures of MΦ and neurons in response to stable, structurally defined Aβ assemblies associated with AD. While not wishing to be bound by any particular theory, the inventors believe that GA-treated MΦ exhibit neuroprotective phenotype through upregulation of the immune modulator OPN, resulting in efficient clearance of pathological Aβ forms, as well as enhanced preservation of neuronal structure and function.

The magnitude of pre-synaptic, post-synaptic, and neuritic length loss, as well as neuronal dysfunction induced by o/pf/fAβ$_{1-42}$ assemblies was determined. Synaptic and neuritic protection by GA-treated MΦ) in response to Aβ$_{1-42}$ assemblies was evaluated. The inventors determined the mechanisms of GA-treated MΦ) preventing synaptic loss and neuronal dysfunction in response to neurotoxic Aβ$_{1-42}$ assemblies and assess the efficiency of MΦ) in internalizing and degrading Aβ$_{1-42}$ assemblies. The inventors determined the MΦ) neuroprotective phenotype associated with functions such as immune regulation and neurotrophic support, with focus on the role of immune modulator, OPN, related to these functions.

The inventors also investigate preservation of synapses and cognitive functions by immune modulation, achieved through GA or grafting BM-CD115$^+$ Mo in murine models, as a potential AD therapy. While not wishing to be bound by any particular theory, we believe that GA immunization or grafted Mo will increase cerebral MΦ) expressing OPN, restoring synaptic structure and preserving cognitive function following loss induced by toxic $A\beta_{1-42}$ in murine models of AD.

Ex vivo pre- and post-synaptic marker and neuritic length loss in disease-related brain regions in AD+ mouse models, as a function of the cognitive impairment was measured. Synaptic and cognitive preservation following immune modulation with either GA, or grafted WT vs. $OPN^{KO}$ CD115+-Mo was evaluated. Immune modulation mechanisms of synaptic preservation in AD+ mice through examination of cerebral MΦ) acquired phenotype(s) associated with preserved synapses were identified.

Initially, synaptic toxicity induced by stable, structurally defined $fA\beta_{1-42}$ and $oA\beta_{1-42}$ forms in primary cortical neurons (CN) was tested. Neurons were incubated for 12 hours with 250 nM of Aβ assemblies or with medium only (vehicle) during day 8 of culture. An extensive loss of pre- and post-synaptic (VGluT1 & PSD-95, respectively) area and number, induced by both $f/oA\beta_{1-42}$ forms, was clearly detected (FIG. 1A-C). Synaptic density quantification indicated a significant 50% reduction in co-localized VGluT1/PSD95+ puncta number following $fA\beta_{1-42}$. Moreover, we detected a 70% decrease in puncta number by $oA\beta_{1-42}$ when compared with CN in medium alone (FIG. 1D; p<0.0001). The statistical difference in co-localized synaptic puncta number between $fA\beta_{1-42}$ and $oA\beta_{1-42}$, suggests increased synaptotoxicity by $oA\beta_{1-42}$ (FIG. 1D). Next, Aβ-induced neuritic retraction was assessed. CN were immunolabeled with anti-Tuj1 and the total neuritic length per neuron was precisely quantified (FIG. 2A-D). Overnight incubation of $f/oA\beta_{1-42}$ led to a massive neuritic retraction compared with control CN group (FIG. 2B vs. 2A). Whether untreated- and GA-treated BM-derived MΦ (CD68+ cells) could prevent synaptic and neuritic loss was tested next. Primary CN and MΦ were co-cultured for 48 h and introduced $A\beta_{1-42}$ forms during the last 12 hours of co-culture. The data indicates that GA-treated Φ extensively protected Tuj1+ neurites in CN from loss induced by $f/oA\beta_{1-42}$ (FIG. 2D). Quantitative analysis of co-localized VGluT1/PSD95+ puncta synaptic number confirmed decreases of 32% and 65% after overnight exposure to $fA\beta_{1-42}$ or $oA\beta_{1-42}$, respectively (FIG. 2E). Interestingly, while both GA-treated MΦ and MΦ alone fully protected against synaptic loss induced by $fA\beta_{1-42}$, GA-treated MΦ were significantly more effective in preventing synaptic loss induced by $oA\beta_{1-42}$ (FIG. 2E; p<0.0001). The in vivo effects of Aβ accumulation on synaptopathy and possible synaptic rescue by GA immunization or grafted BM-CD115+ Mo was assessed. Pre- and post-synaptic alterations in coronal brain sections of 13 m old AD+ (ADtg) mice that received these immune-modulation interventions were quantified (FIG. 3A-D). High magnification z-stack images obtained from 19 predefined areas in hippocampus and entorhinal cortex were captured in respective Bregma regions (FIG. 3A-D). The data indicate a significant loss of pre- and post-synaptic density in brains of AD+ mice (PBS controls) compared to matched WT littermates (FIG. 3E). Notably, the immune modulation therapies significantly rescued synaptic formations (FIG. 3E; p<0.001). The in vitro data from the brains of 13 m old AD+ mice suggest a significant $A\beta_{1-42}$-induced loss of pre- and post-synaptic areas, and a remarkable synaptic rescue in mice receiving GA immunization or grafted Mo (FIG. 3E). These results raise the question of whether synaptic loss induced by $A\beta_{1-42}$ assemblies leads to neuronal dysfunction, and whether synaptic rescue by GA-treated MΦ will affect neuronal function preservation.

Figure 6A:
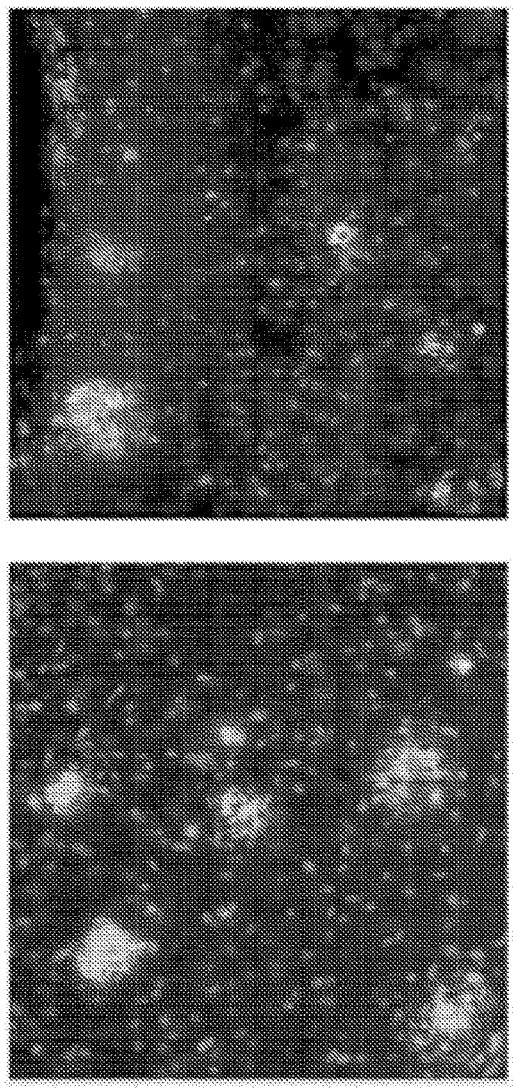
FIGS. 6A-6B depict increased OPN levels caused by infiltrating MΦ in GA-immunized AD+ mouse brains in accordance with various embodiments of the present invention.
Figure 6B:
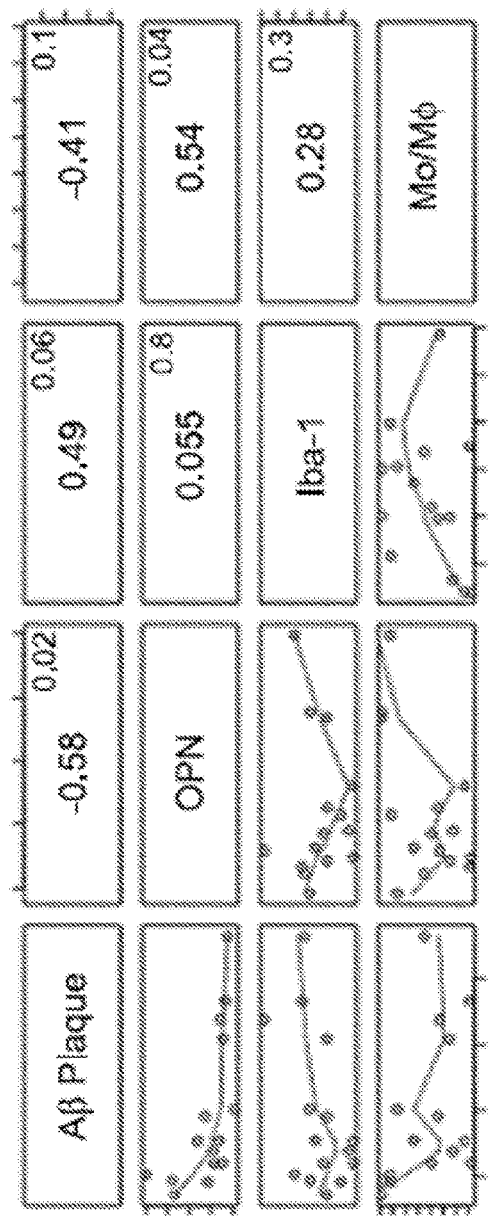

To elucidate possible mechanisms by which MΦ may exert their synaptoprotective effects, the capability of MΦ to clear Aβ1.42 assemblies via binding, internalizing, and transferring them into endosomes was assessed (FIG. 4). Quantification of Aβ co-localized within early endosomes (EEA1+ vesicles) after 15 min of MΦ uptake indicates a significantly higher endosomal presence of $fA\beta_{1-42}$ vs. $oA\beta_{1-42}$ (FIG. 4D), perhaps indicative of enhanced MΦ clearance mechanism of $fA\beta_{1-42}$. An upregulation of immune-modulator OPN in MΦ after GA treatment was also identified (FIG. 5A-D). The 2-fold increase in OPN in GA-treated MΦ was associated with a 2.8-fold rise in $fA\beta_{1-42}$ uptake (FIG. 5D). Examination of brain tissues from AD+ mice receiving GA immunization or grafted Mo also revealed upregulation of OPN, especially at Aβ plaques and expressed by MΦ (FIG. 6A). Cerebral OPN expression correlated inversely with 6E10+ plaque area, and positively correlated with infiltrated Mo/MΦ; a correlogram demonstrates the relationships between OPN levels and Aβ-plaque burden ($R^2$=−0.58; p=0.02), and OPN and infiltrating Mo/MΦ ($R^2$=0.54; p=0.04) (FIG. 6B). OPN knockdown via siRNA leads to decreased $fA\beta_{1-42}$ phagocytosis by GA-treated MΦ, suggesting a mechanism for OPN in mediating GA-enhanced Aβ phagocytosis (FIG. 7A-C).

While not wishing to be bound by any particular theory, we believe that macrophages (MΦ) treated with GA increase expression of immune modulator OPN, resulting in enhanced clearance of pathological Aβ forms and immune profile(s) in support of preserved neuronal structure and function. See Table 1 for an overview of in vitro experimental design.

TABLE 1

| Group | Synaptic & Neuritic Integrity/MEA recording |
|---|---|
| Cortical Neurons (CN) | CN + f/pf/oAβ |
| CN + MΦ/GA – MΦ | CN + MΦ/GA – MΦ + f/pf/oAβ |
| CN + MΦ/GA – MΦ + OPN siRNA | CN + MΦ/GA – MΦ + OPN siRNA + f/pf/oAβ |

P1 neurons are prepared as previously reported. Briefly, cortical neurons (CN) are obtained from 1 day old neonatal mice, dissociated, resuspended and plated in 24-well culture plate at $5\times10^4$/ml cells. BM-MΦ are obtained as described herein. In short, mononuclear enriched BM-derived cells are isolated from C57BL/6 mice and differentiated into MΦ for 7 days. Co-cultures of neurons and MΦ are prepared by suspension of primary MΦ into primary CN culture (ratio of 1:1) for 48 h. CN alone or co-cultures of CN with MΦ are incubated overnight with preformed (purified and stabilized) f-, pf- or $oA\beta_{1-42}$ (FIG. 8). For assessing GA effects and OPN inhibition, MΦ are treated with GA (30 mg/ml, TEVA Neuroscience) with and without OPN- or scrambled-siRNA (Invitrogen, Stealth Select) for 24 h before co-culturing. Experiments will be carried out after 9 days of seeding CN. Cultures are processed for quantification of synaptic density and neuritic length. Primary cultures are identically stained with presynaptic VGluT1 (Chemicon, 1:6,000), postsynaptic PSD95 (Abcam, 1:600) (for synapses) or Tuj1 (for neurites). Negative controls are processed similarly, omitting either primary or secondary antibodies. Microphotographs are shot using a Carl Zeiss ApoTome-equipped Axio Imager Z1 fluorescence microscope. Synaptic puncta number and synaptic immunoreactive area are quantified with Puncta Analyzer. Total neurite length is measured using NeuriteTracer. At least 3 coverslips, 36 images and 150 neurons for each condition are analyzed. Average puncta number, synaptic area per image or per neuron will be calculated. The spontaneous network activity of CN using microelectrode array (EMA) is performed in the lab of Dr. Clive Svendsen. The MEA recording protocol will be carried out as published. In brief, on day 9 of culture, spontaneous network activity of CN is recorded for 60 min to gain baseline. Then, those neurons incubated with f/pf/oA$\beta_{1-42}$, and co-cultured with GA-treated MΦ w/or w/o OPN siRNA or MΦ alone are recording using an Axion Maestro MEA device. Total action potential firing rates and mean neuronal firing frequencies are then determined and plotted. Intracellular A$\beta_{1-42}$ uptake by MΦ is quantitatively assessed by ELISA of A$\beta_{1-40}$/A$\beta_{1-42}$ levels in cell lysate and by ICC as described herein. See FIG. 9A for schematics of in vitro experiments.

While not wishing to be bound by any particular theory, we believe that GA immunization or blood enrichment with BM-CD115$^+$ Mo will rescue synaptic structure and cognitive function in AD$^+$ mice via increased cerebral recruitment of MΦ expressing OPN at plaque lesions and enhancing removal of A$\beta_{1-42}$. See Table 2 for an overview of in vivo experimental design.

TABLE 2

| Group | Synaptic and Neuritic Integrity/Cognitive Tests |
| --- | --- |
| Naïve WT or PBS-treated AD$^+$ mice | PBS, WT |
| Blood grafted MO$^{wt}$ or Mo$^{OPN-}$ in AD$^+$ mice | GA MO$^{wt}$, Mo$^{OPN-}$ |

All experiments using AD$^+$, OPN knockout (OPN$^{KO}$) and GFP line mice (Jackson Labs) are conducted according to regulations of the Cedars-Sinai Medical Center IACUC. Mouse tissues will be processed as described herein. Brain sections are identically stained with VGluT1 and PSD95 (for synapses) or Tuj1 (for neurites), and images captured as described above. To cover the hippocampal area, 15 identical rectangular fields (90 μm×70 μm) under a 100× objective lens are precisely selected in ML of DG, and SLM, SR and SO of CA1, respectively. In addition, 4 identical fields are carefully chosen in entorhinal cortex layers 2 and 3. Single optical section images at 0.25 μm intervals and 3.75 μm Zeiss ApoTom high resolution scans are performed (FIG. 3A-D). Synaptic puncta number/area and total neurite length are quantified with Puncta Analyzer and NeuriteTracer. Average puncta number, synaptic area per image or per neuron are calculated for each condition. Barnes maze behavioral tests are performed as we previously described. See FIG. 9B for the schematics of in vivo experiments. To study mechanisms of action, we propose, as mentioned above, to assess efficiency of A$\beta_{1-42}$ assembly clearance, and determine Φ neuroprotective phenotype associated with functions such as immune regulation, neurotrophic support. We specifically study the role of an immune modulator OPN in these functions. See the Table 3 overview of experimental design for both in vitro and in vivo mechanisms. Levels of scavenger receptors (Scara-1, CD36, CD163) and degrading enzymes (MMP-9, ACE, neprilysin) will be also determined by sandwich ELISA according to the manufacturer's protocols (R&D system). Expression of pro- and anti-inflammatory cytokines, OPN, IL-10, TGFβ1, iNOS, and TNFα (R&D system) will be examined through ELISA and/or IHC. In addition to TGFβ1 and OPN, measurement of neurotrophic support by IGF-1 is also carried out. Using markers including GFP-labeling, Iba-1, CD11b, Ly6C and/or CD45, cerebral infiltration of Mo/MΦ populations is determined by FACS and IHC.

TABLE 3

| Mechanism | Molecules studied |
| --- | --- |
| Ab clearance | Ab, Scara-1, CD36, CD163 and MMP-9 |
| Immune regulation | OPN, IL-10, TGFb1, iNOS, and TNFa |
| Neurotrophic support | IGF-1, TGFb1, OPN |
| Mo/MΦ populations | GFP, Iba-1, CD11b, Ly6C, CD45 by FACS & IHC |

Example 3

OPN Expression Pattern is Associated with Amyloid Plaques in AD-Related Brain Regions OPN expression patterns in various brain regions of ADtg and age- and gendermatched non-Tg, wild-type (WT) mice was analyzed (FIG. 10). Immunohistochemistry (IHC) revealed distinct OPN expression patterns in all AD-associated brain regions (hippocampus, cingulate cortex, and entorhinal cortex; FIG. 10A) within or in close proximity to Aβ plaques (FIG. 10B). OPN immunolabeling was largely undetectable in control WT mice. Similar patterns of OPN expression were observed in brains of ADtg mice with peroxidase labeling (FIG. 10C). In brain regions not typically associated with AD (i.e. striatum), OPN immunostaining was predominantly confined to neurons in both ADtg and WT mice (FIG. 17A-17B). Without being bound to any particular theory, these results demonstrate that in AD-associated brain regions of ADtg mice, OPN was selectively expressed by myeloid cells associated with Aβ plaques.

Figure 10C:
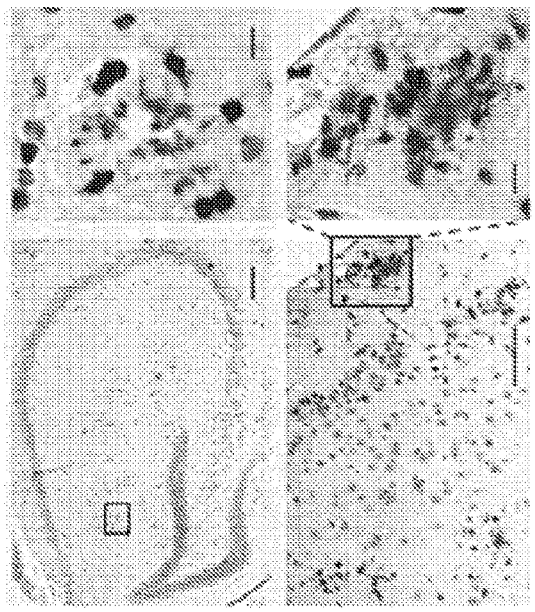
FIGS. 10A-10F depict in accordance with various embodiments of the present invention, OPN expression patterns in brains of ADtg (AD) and Wild-Type (WT) mice.
Figure 10A:
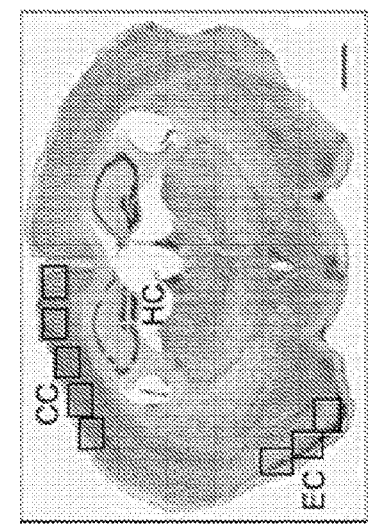
Figure 10B:
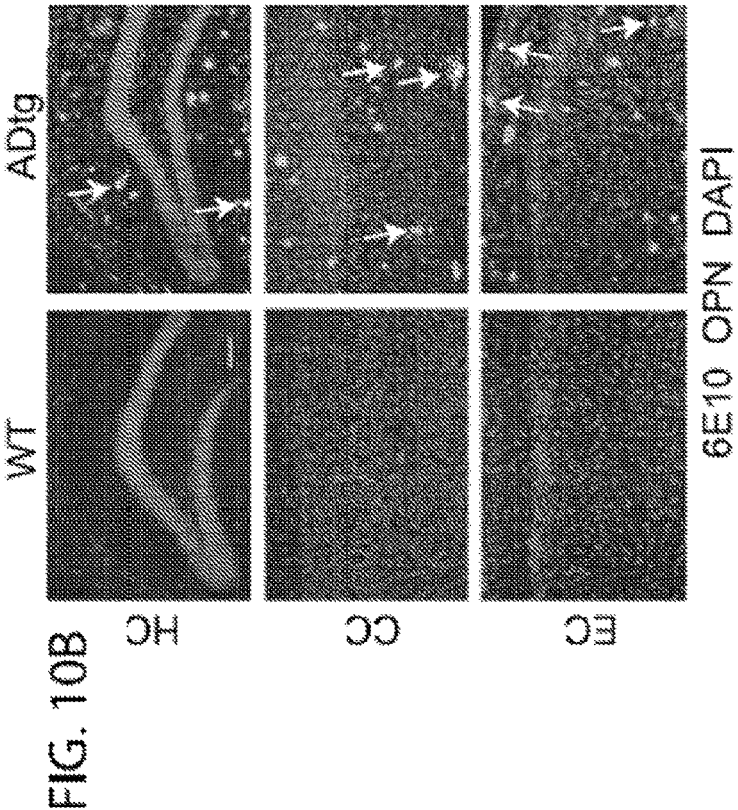
Figure 10E:
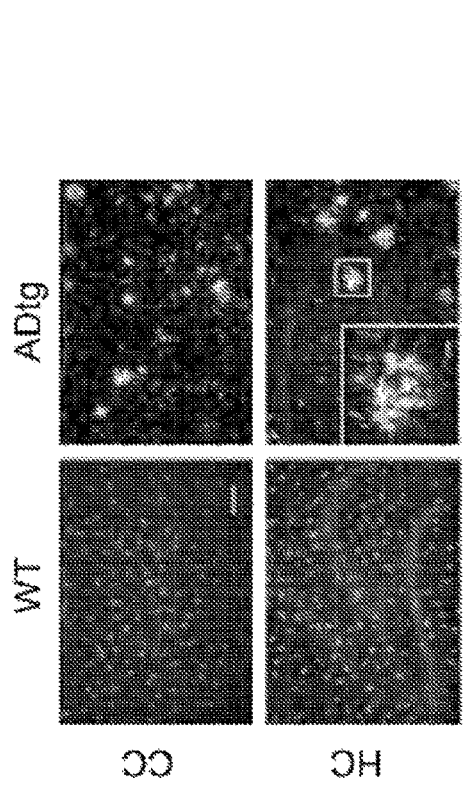
Figure 10F:
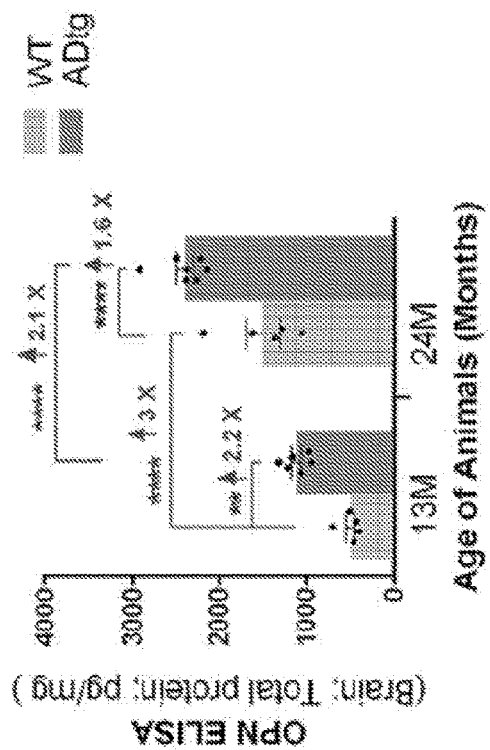
Figure 10D:
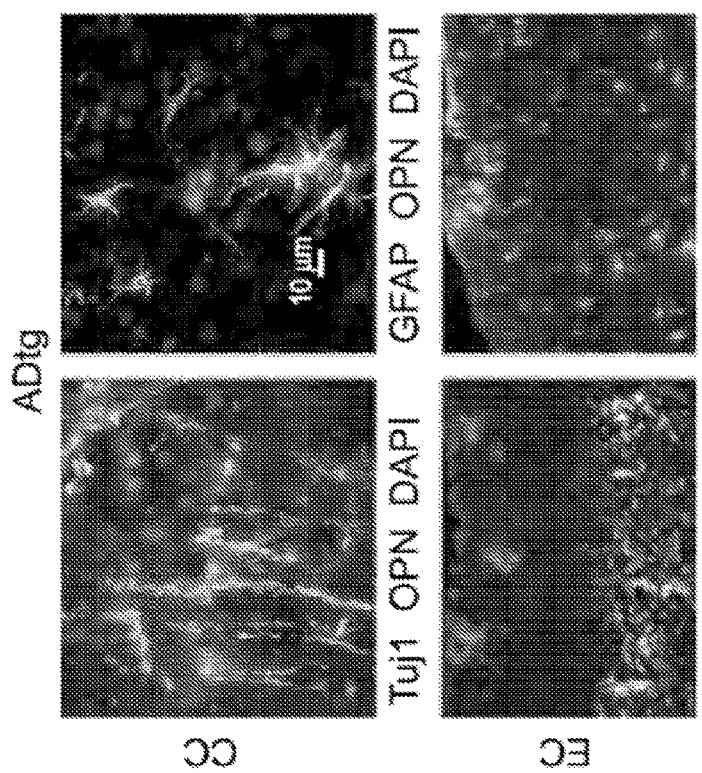

Upregulation of Cerebral OPN Expression by GA Immunization is Inversely Correlated with Aβ Plaque Burden To study the effect of GA immunization on OPN expression in the brain, three treatment groups in symptomatic ADtg mice: GA immunized (s.c. once a week for 2 months), GA+Mo$^{BM}$ combined treatment (weekly s.c. GA plus monthly i.v. injections of a Mo$^{BM}$ subset for 2 months) and PBS control groups (i.v. injected with PBS monthly for two months) were analyzed. Representative micrographs of coronal brain sections covering hippocampal (HC) and cingulate cortical regions revealed elevated OPN immunoreactivity along with reduced 6E10$^+$-Aβ plaque burden in GA- and GA+Mo$^{BM}$-immunized mice compared with PBS controls (FIG. 10A). Similar results were observed in the entorhinal cortex (EC; not shown).

Figure 11B:
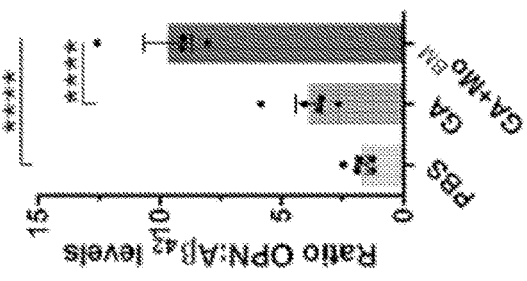
Figure 11D:
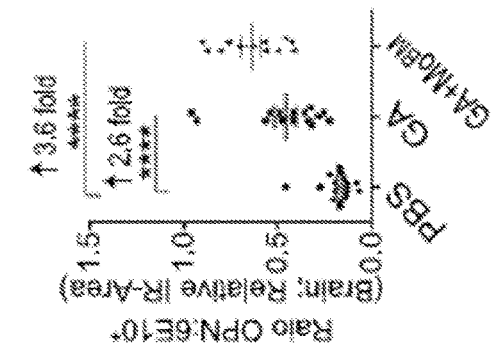
Figure 11C:
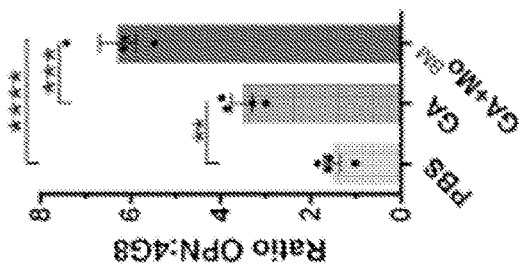
Figure 11F:
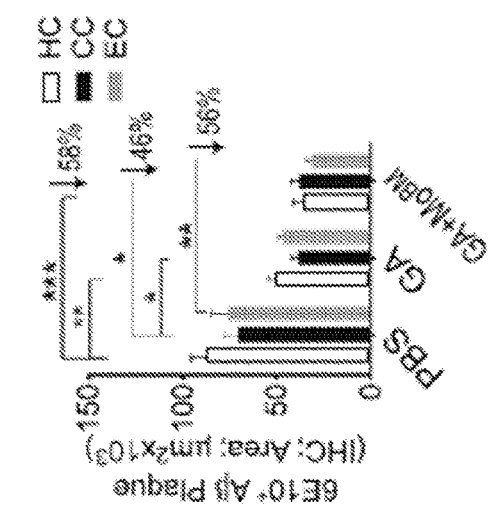
Figure 11E:
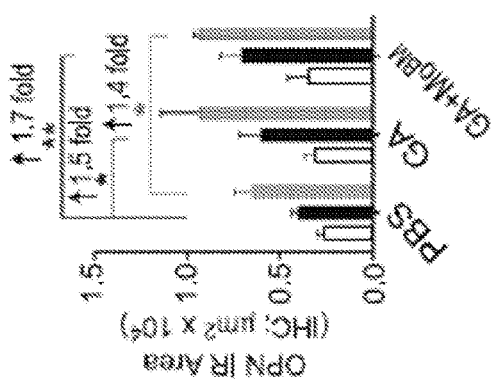
Figure 11G:
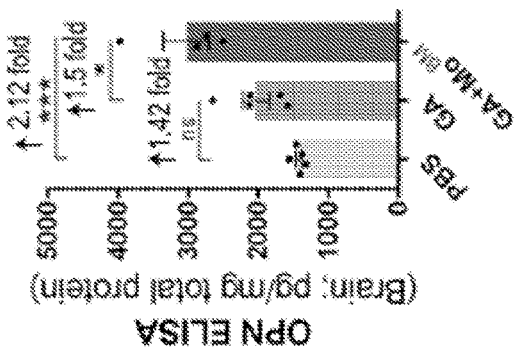
Figure 18C:
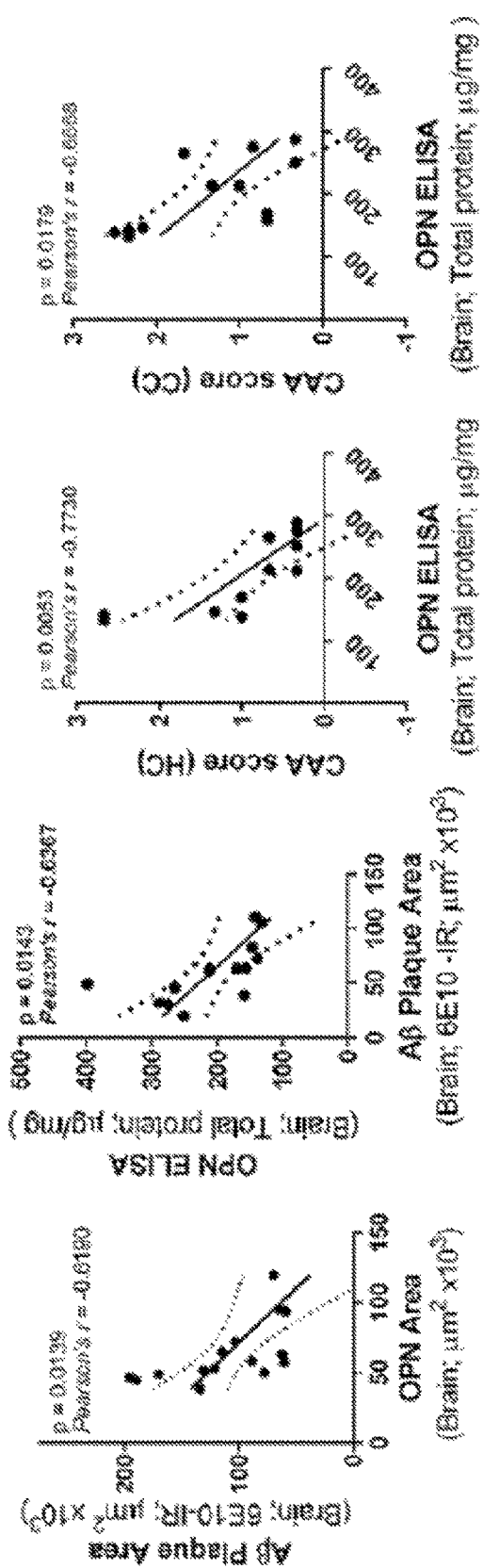
Figure 18D:
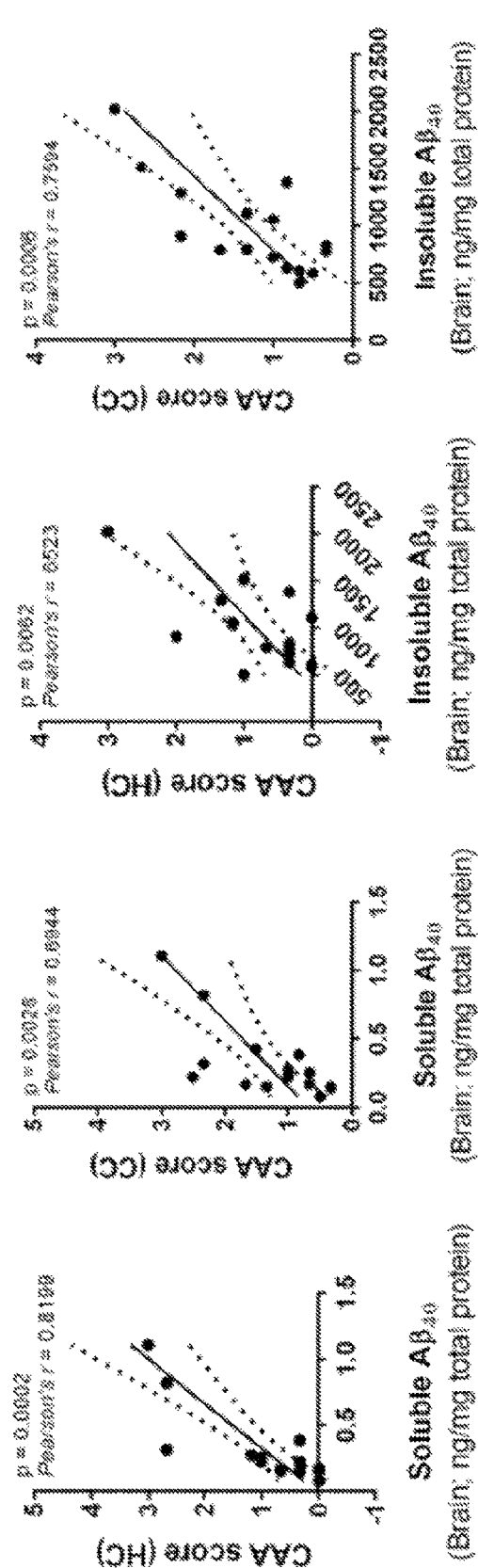

Quantitative immunohistochemistry (IHC) validated a significant increase in cerebral OPN expression in both GA-immunized ADtg mouse groups (FIG. 11B and FIG. 18A). In comparison to PBS controls, OPN expression in mice treated with GA was 1.5 times higher, and was consistently highest in the EC and lowest in the HC. This difference was even greater in the GA+Mo$^{BM}$ group, in which cerebral OPN was 1.7 times that of PBS controls (FIG. 11B). Assessment of 6E10$^+$-Aβ plaque burden in the same brain sections showed substantial reduction in GA-immunized groups (GA and GA+Mo$^{BM}$) compared with PBS controls (FIG. 11C).

Figure 11H:
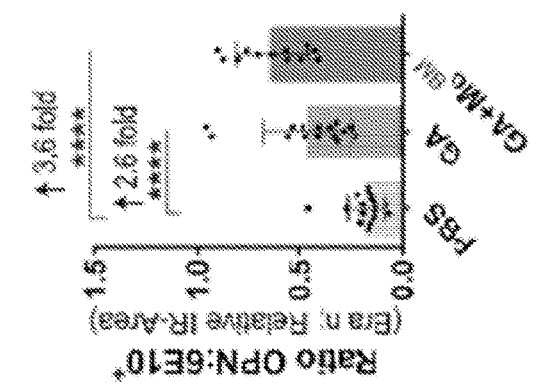
Figure 11I:
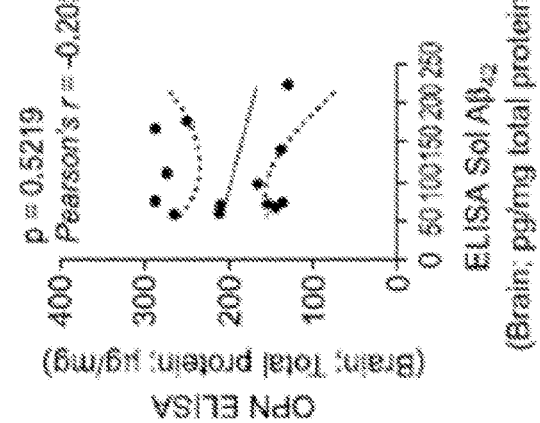
Figures 11J, 11K:
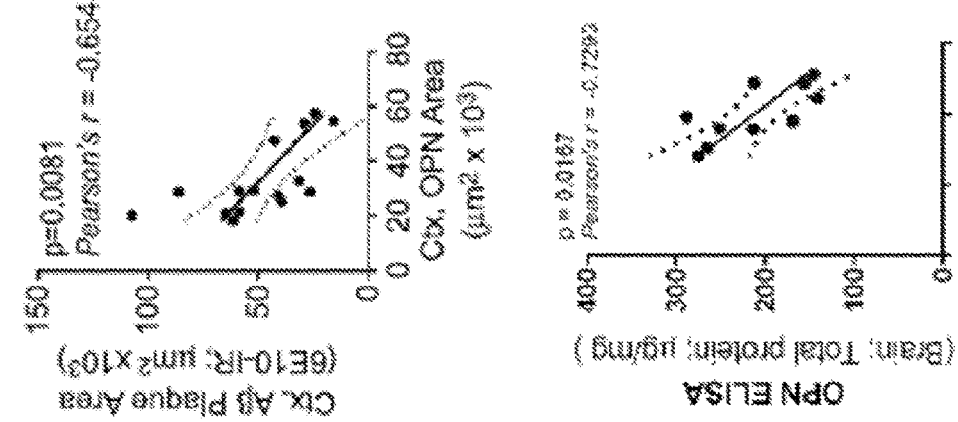
Figure 11L:
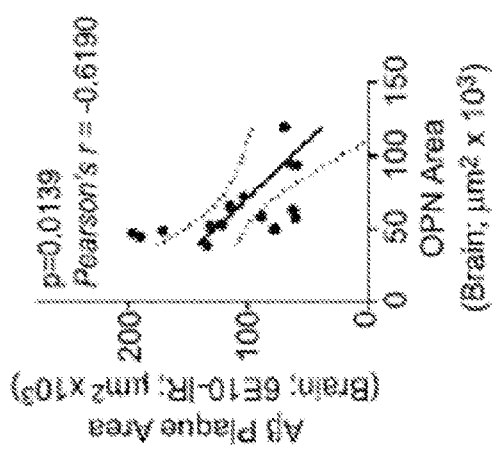

Next, OPN expression levels were measured against areas of plaque burden. The ratios of total OPN area to plaque area in total brain regions were quantified (FIG. 11D and FIG. 19B). Both of the GA-immunized groups displayed significant increase (2.6- and 3.6-fold, respectively) in total OPN expression per Aβ-plaque area. Separate cortical and hippocampal analyses showed similar results (FIG. 18B). These effects on elevated OPN expression within Aβ plaques were greater for the combined GA+Mo$^{BM}$ group (FIG. 11D). Correlation analyses using Pearson's tests indicated a significant inverse relationship between OPN expression and 6E10 plaque burden (FIG. 11H), with a stronger correlation seen in cortical regions (FIG. 11I). Without being bound to any particular theory, these results collectively indicate that GA immunization in ADtg mice leads to upregulation of cerebral OPN expression, concomitant with decreased amyloid plaque burden.

OPN is Predominantly Expressed by Infiltrating Monocyte-Derived Macrophages Involved in Aβ Clearance To identify OPN-expressing cells in ADtg mouse brains, two different approaches were used. In order to distinguish infiltrating monocytes/macrophages (Mo/MΦ) from microglia, the combined Iba-1 and CD45 markers was first used (FIG. 13A). Representative fluorescent micrographs revealed selective expression of OPN by cerebral infiltrating Iba1$^+$ CD45$^{high}$ Mo/MΦ compared with resident Iba1+ CD45$^{int-low}$ microglia (FIG. 13A). These infiltrating OPN-expressing Iba1$^+$ CD45$^{high}$ Mo/MΦ accumulated at and around plaque lesion sites, and engulfed Aβ directly (FIG. 13A, arrow). In the second approach GFP-labeled CD11b+ CD115+-Mo$^{BM}$ were isolated from young donor WT mice and injected into the tail veins of symptomatic 10-month-old ADtg mice (FIG. 13B). These GFP$^+$ CD45$^{high}$-expressing Mo/MΦ were distinguishable from GFP-microglia and intensely co-labeled with OPN. Mo/MΦ expressing high OPN were often concentrated in the EC, homing to brain parenchyma around plaque lesion sites (FIG. 13B-13C). The subcellular localization of OPN within infiltrating Mo/MΦ in ADtg mouse brains was also examined. OPN was found in vesicular compartments and across the cell body and processes (FIG. 13D-13E). OPN expression was particularly strong in the perinuclear zone.

Figure 13G:
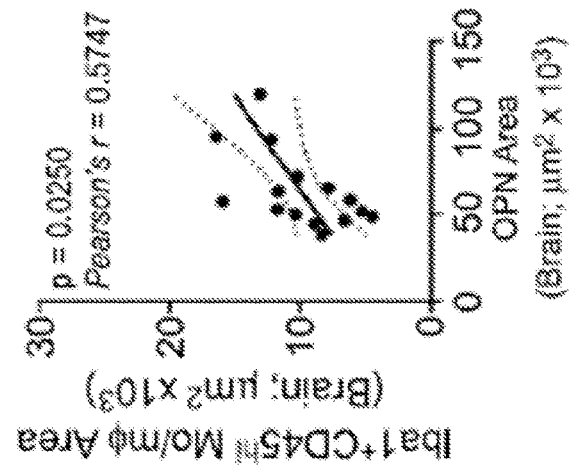
Figure 13F:
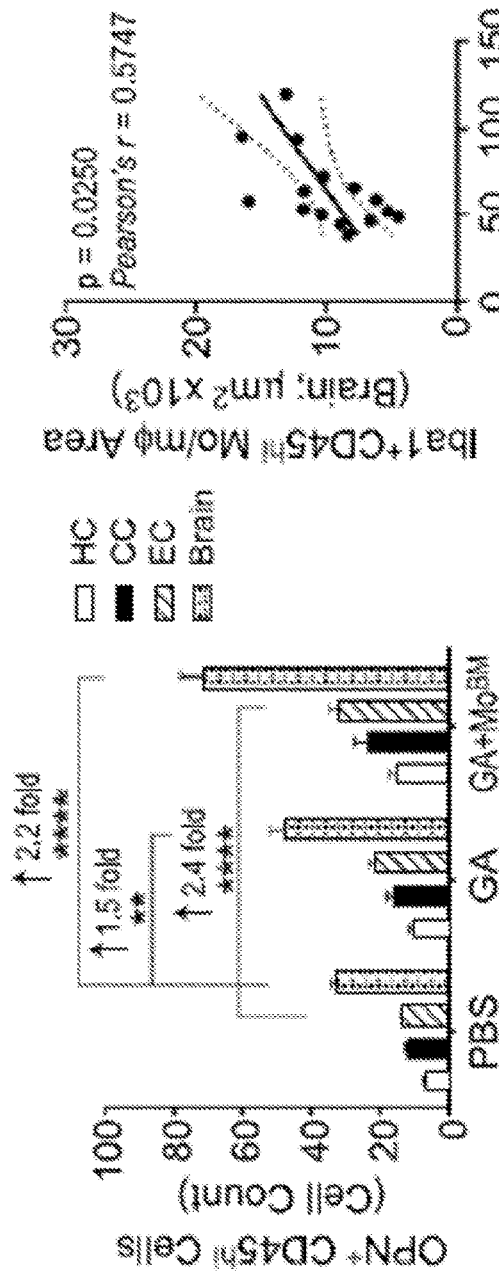

Next, OPN+CD45$^{high}$ cell count per section across the above-mentioned brain regions was quantified. Substantial 1.5- and 2.2-fold increases in number of infiltrating OPN+ CD45$^{high}$ cells were detected in GA and GA+Mo$^{BM}$ groups, respectively, in comparison to PBS controls (FIG. 13F). Correlation analysis demonstrated a significant direct linear relationship between OPN expression and infiltration by Iba1$^+$ CD45$^{high}$ Mo/MΦ in ADtg mice (FIG. 13G). A tighter association between expression of the OPN cytokine and recruited myeloid cells around plaques was indicated by ratios of CD45$^{high}$ and OPN expression per 6E10 immunoreactive area (FIG. 19B). Multifactor correlogram analyses confirmed the inverse relationship between OPN expression and Aβ plaque burden, along with a direct association between infiltrating Mo/MΦ and OPN expression (FIGS. 6B and 19A). Without being bound to any particular theory, these results suggest that GA induces cerebral recruitment of OPN-expressing Mo/MΦ in ADtg mice, which indicates that OPN expression is elevated by GA immunization in ADtg mice, predominantly in infiltrating Mo/Mt directly involved in cerebral Aβ-plaque clearance.

GA Upregulates OPN Expression in Primary Cultures of BM-Derived Macrophages

Figure 14A:
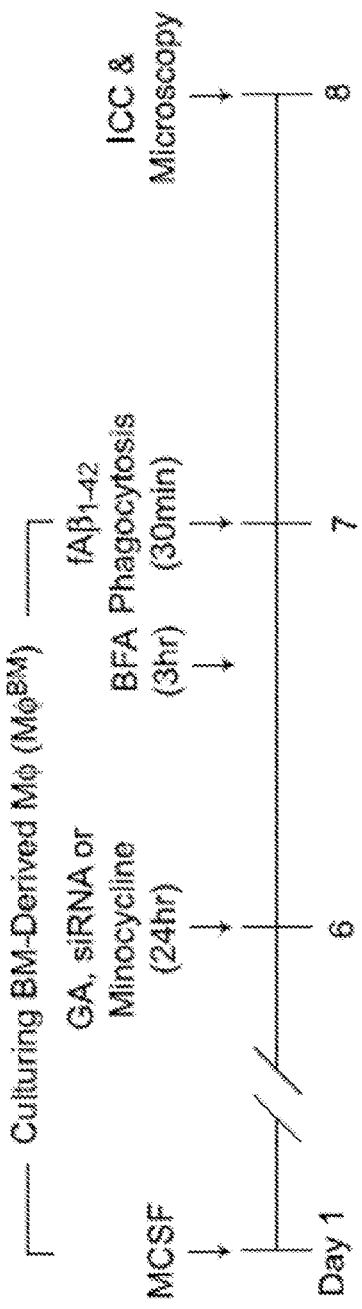
FIGS. 14A-14J depict in accordance with various embodiments of the present invention, GA upregulates OPN expression in primary cultures of BM-derived macrophages.
Figure 14D:
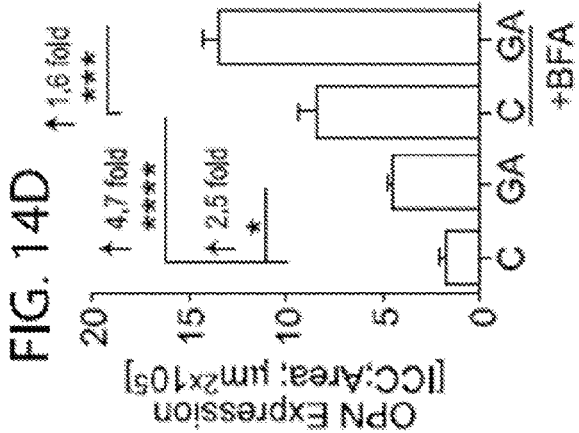
Figure 14E:
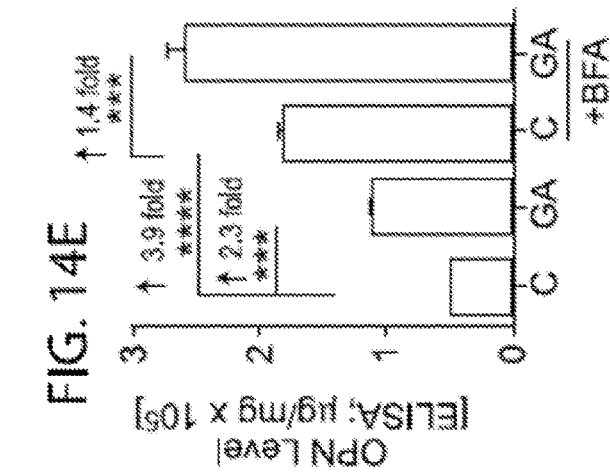
Figure 14B:
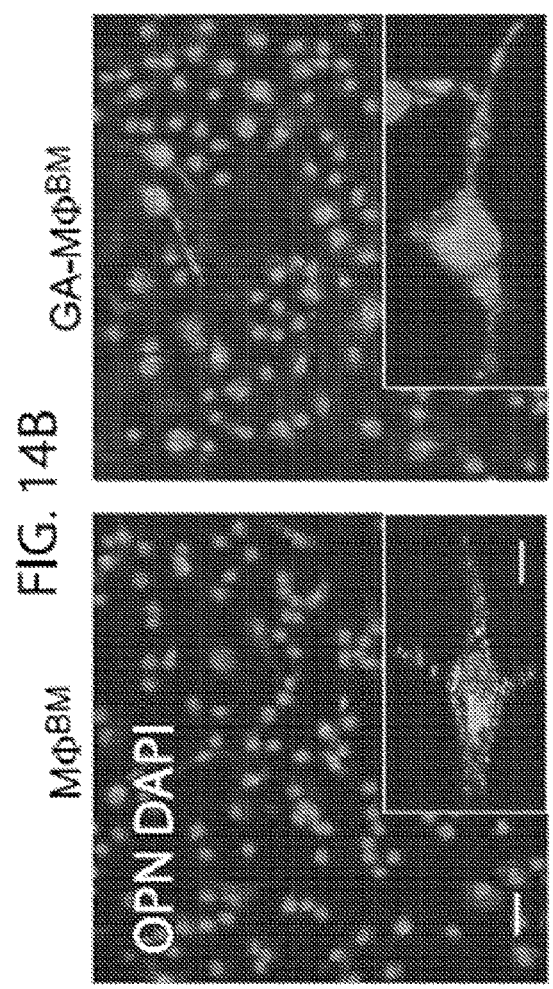
Figure 14C:
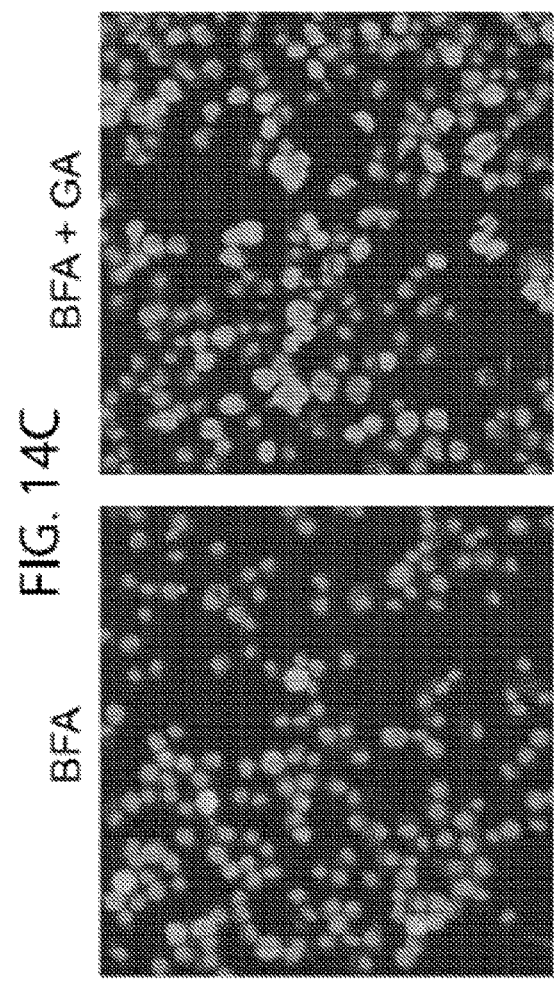
Figure 14G:
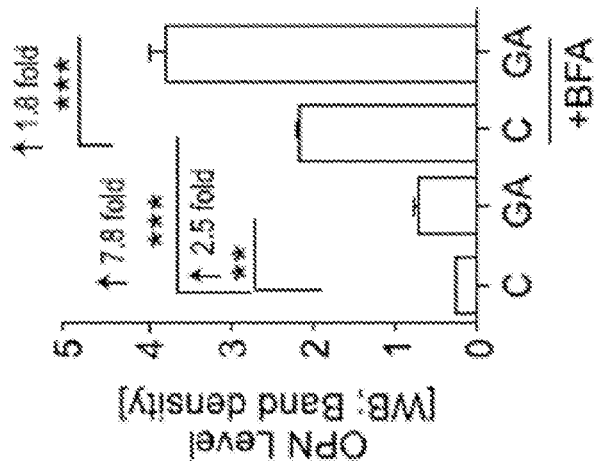
Figure 14F:
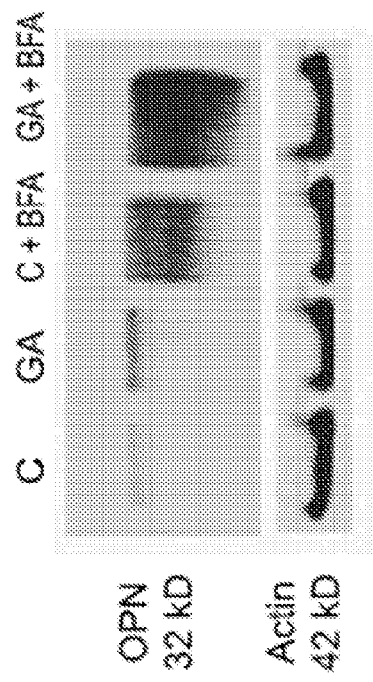
Figure 14H:
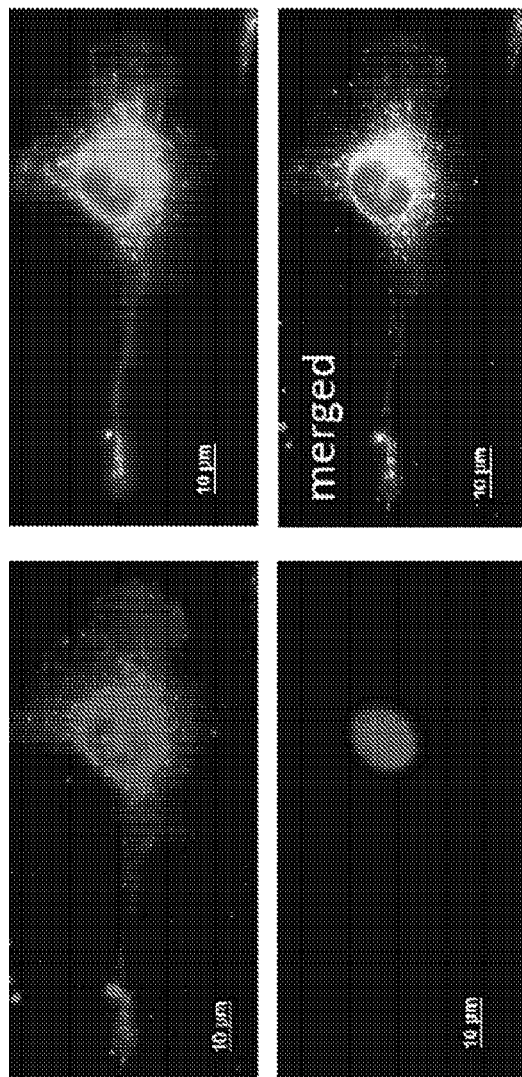
Figure 14I:
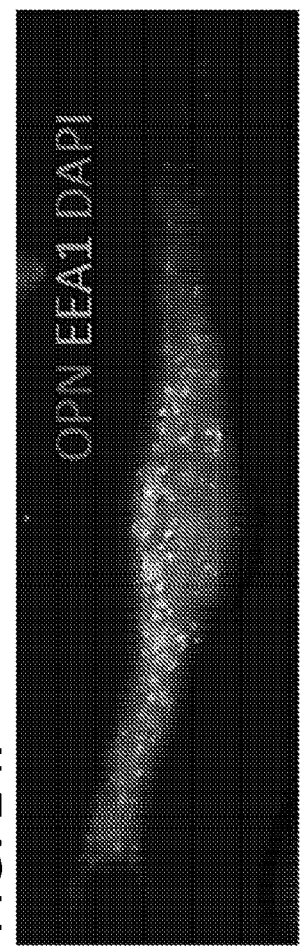
Figure 14J:
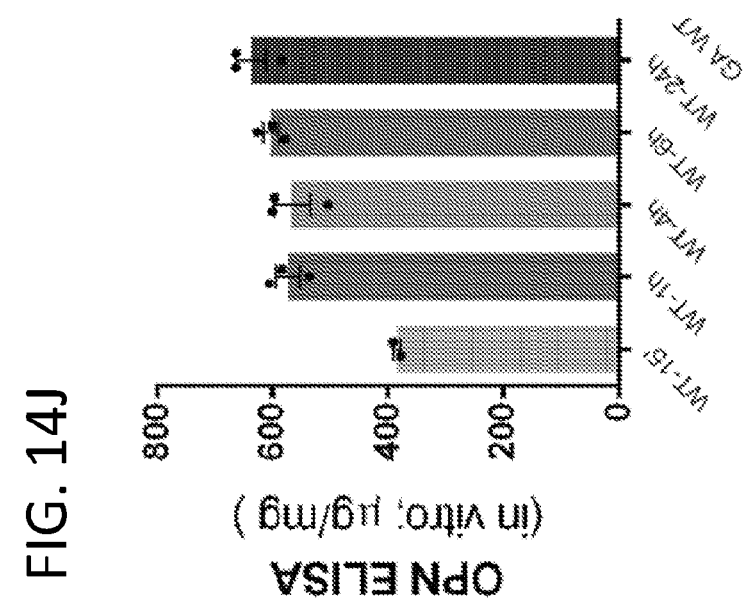

To investigate the impact of GA on OPN expression in macrophages, a series of in vitro studies using primary MΦ$^{BM}$ was performed. BM was isolated from young WT donor mice, differentiated into mature macrophages, pretreated overnight with GA (30 μg/ml; GA-MΦ$^{BM}$) and exposed to pre-formed Aβ$_{1-42}$ fibrils. Representative fluorescent images show that in initial experiments without Aβ, OPN was expressed constitutively by MΦ$^{BM}$ in culture and overexpressed upon exposure to GA (FIG. 14B). Since MΦ$^{BM}$ constitutively express and secrete OPN into the extracellular matrix, OPN production by inhibiting secretion with Brefeldin A (BFA) pretreatment was assessed (FIG. 14C). Indeed, newly generated OPN was trapped by BFA, increasing its intracellular accumulation. Subsequently, these cells exhibited decreased cell adhesion and an altered, round morphology. GA further elevated OPN production in BFA-pretreated MΦ$^{BM}$ (FIG. 14C). Quantitative immunocytochemistry (qICC) confirmed significant 1.6- and 2.5-fold increases in OPN production/expression (with and without BFA, respectively) in GA-MΦ$^{BM}$ vs. untreated MΦ$^{BM}$ (FIG. 14D). A quantitative enzyme-linked immunosorbent assay (ELISA) analysis of cell lysates validated these results, indicating increased OPN levels (1.4- and 2.3-fold, with and without BFA, respectively) following GA treatment (FIG. 14E). The BFA condition suggested a substantial accumulation of OPN in MΦ$^{BM}$ in short periods of time (i.e. within 1-3 hours). Taken together, ELISA, qICC, and Western blot assessments of OPN (FIG. 14D-14G) mirrored our in vivo results, indicating that GA markedly induces OPN expression and production in WΦ$^{BM}$.

OPN Positively Regulates Aβ Phagocytosis in GA-Activated Macrophages

Whether increased OPN expression resulting from GA activation is associated with the ability of macrophages to phagocytose pathogenic Aβ aggregates was then examined. MΦ$^{BM}$ were pretreated with GA, as previously described, and stimulated with 100 nM fibrillar Aβ$_{1-42}$ for 30 min. Representative high magnification Z-stack images demonstrated that intracellular OPN expression in MΦ$^{BM}$ was accompanied by phagocytosis of fibrillar Aβ$_{1-42}$ (FIG. 15A). Enhanced Aβ uptake was associated with increased OPN expression in GA-treated MΦ$^{BM}$, as detected by qICC analysis (FIG. 15B-15C). Representative images show a distinct pattern of OPN immunoreactivity within somas and along processes of CD68$^+$ phagocytes, with strong perinuclear and evenly distributed vesicular signals, accompanied by punctate Aβ labeling. This staining was substantially increased after GA treatment (FIG. 15G-15H'). Quantitative ELISA analyses of cell lysates validated the above qICC results, indicating increased intracellular OPN and Aβ$_{1-42}$ in GA-treated vs. untreated MΦ$^{BM}$ (FIG. 15I-15J). These results show that GA increases both OPN expression (2.3-2.7 fold) and fibrillar Aβ$_{1-42}$ uptake in MΦ$^{BM}$ (2.5-2.85 fold).

Figure 15M:
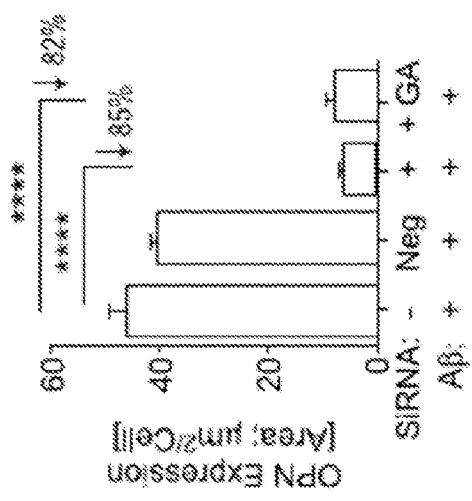
FIG. 15M-15N) Quantitative ICC revealed reduced OPN expression and impaired fAβ$_{1-42}$ phagocytosis following siRNA-mediated knockdown of OPN in MΦ$^{BM}$ and GA-MΦ$^{BM}$. Negative control scrambled siRNA (Franzen and Heinegard) had no effect on OPN expression or Aβ phagocytosis. Addition of GA had little to no impact on OPN expression or Aβ uptake after OPN knockdown.
Figure 15N:
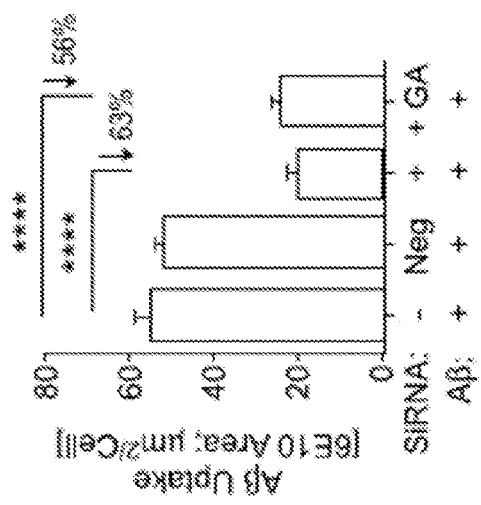
Figure 15L:
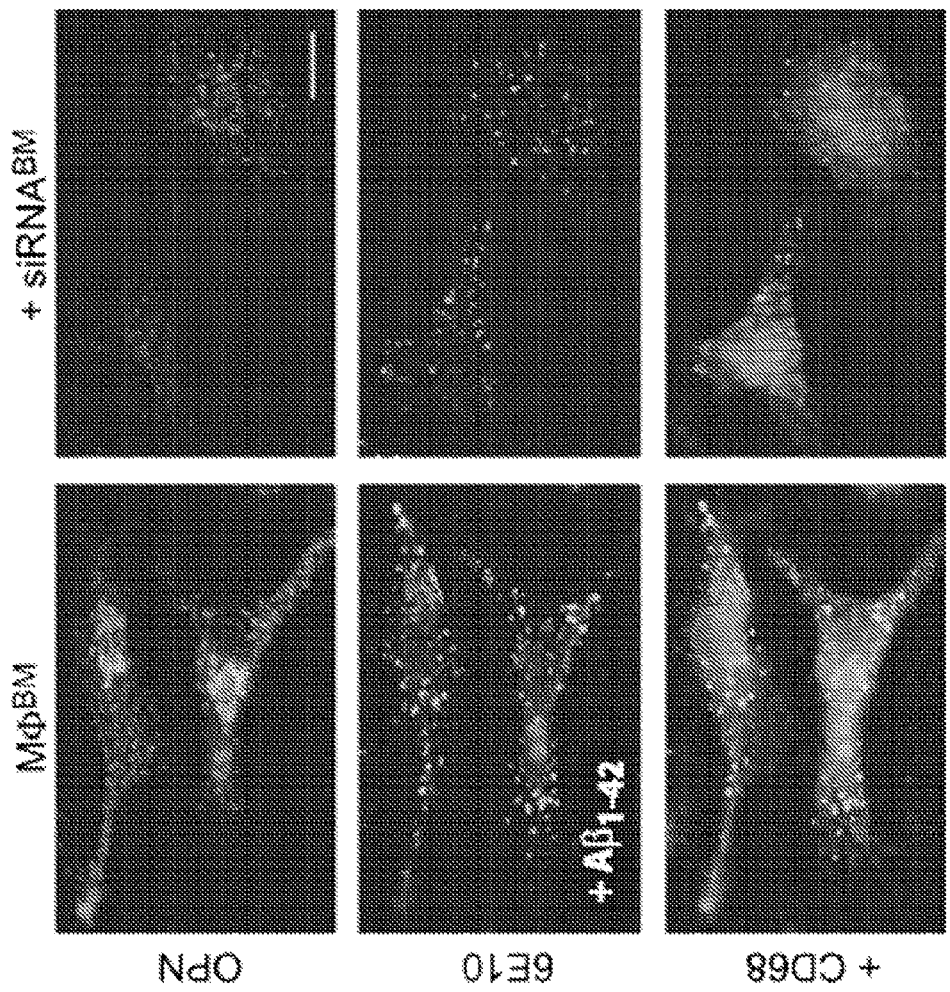
FIG. 15L) Representative micrographs of MΦ$^{BM}$ cells untreated versus transfected with siRNA$^{OPN}$, displaying fAβ$_{1-42}$ phagocytosis.
Figure 15P:
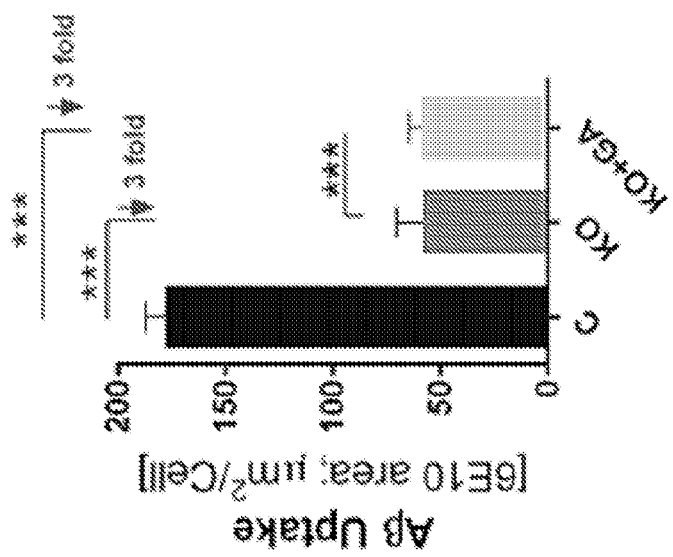
Figure 15O:
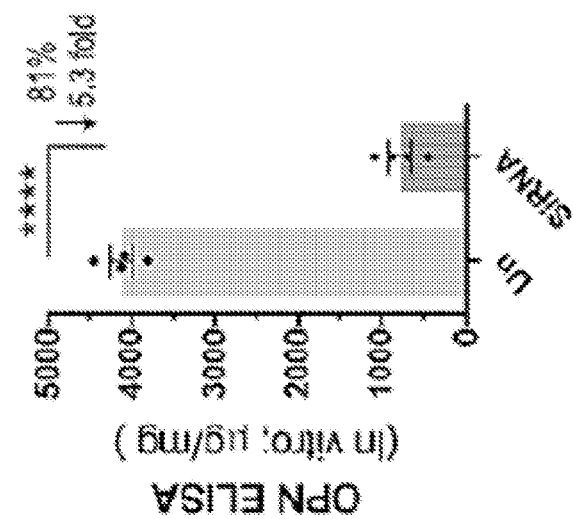
FIG. 15O) OPN ELISA in untreated and siRNA transfected.

Previous studies have suggested that intracellular OPN deletion in macrophages impairs phagocytic activity. Here, to assess OPN involvement in specific phagocytosis of Aβ, OPN expression was knocked down using siRNA (FIG. 15L-15N). MΦ$^{BM}$ cells were transfected with either siRNA$^{OPN}$ or control siRNA$^{Neg}$, and 48 hours later fibrillar Aβ$_{1-42}$ was added followed by a phagocytosis assay. Representative fluorescent images revealed substantial reduction in fibrillar Aβ$_{1-42}$ uptake by CD68$^+$ MΦ$^{BM}$ following siRNA-OPN inhibition (FIG. 15L). Quantitative ICC analyses validated the observations and indicated that 82-85% OPN inhibition was associated with 56-63% reduced intracellular uptake of Aβ$_{1-42}$ fibrils (FIG. 15M-15N). These results demonstrate that phagocytosis of fibrillar Aβ$_{1-42}$ was impaired in the absence of OPN (FIG. 15N). Negative control scrambled siRNA did not affect OPN expression or Aβ phagocytosis. Furthermore, GA had little to no impact on MΦ$^{BM}$ ability to uptake Aβ when OPN was inhibited. Overall, without being bound to any particular theory, the data suggest that OPN mediates the ability of macrophages to phagocytose fibrillar Aβ$_{1-42}$, an activity that gains function by GA-mediated OPN induction and loses function upon OPN inhibition.

GA Promotes Macrophage Polarization by Inducing OPN and its Active Fragments

Macrophages can acquire distinct phenotypes and biological functions depending on their microenvironment. Past studies reported that OPN promotes macrophages to switch to the anti-inflammatory M2 phenotype. The possible role of OPN in macrophage polarization towards an anti-inflammatory phenotype, which has been associated with elongated cell shape was explored. Cell length under various treatment conditions was analyzed and found that in cells undergoing GA treatment with amplified OPN expression, length increased 1.3-fold. In contrast, siRNA$^{OPN}$ knockdown reversed GA effects, and further decreased cell length by ~30-40% (FIG. 16A-16B). In the absence of OPN, GA did not affect macrophage cell elongation (FIG. 16B), similar to the results of our Aβ-phagocytosis following siRNA$^{OPN}$ knockdown (FIG. 15N).

The expression of inducible nitric oxide synthase (iNOS), a hallmark of the proinflammatory M1 macrophage phenotype, in different treatment groups was assessed next (FIG. 16C-16D). The tricyclic antibiotic minocycline was used to suppress OPN expression. Minocycline has been shown to modulate inflammatory responses and to reduce matrix metalloproteinase (MMP)-9 activity and generation of proteolytic OPN fragments. MΦ$^{BM}$ were either OPN-activated by GA or OPN-inhibited by minocycline and then exposed to fibrillar Aβ for 30 min. Fluorescent micrographs demonstrated that GA reduced iNOS expression and increased fibrillar Aβ$^{1-42}$ phagocytosis, while minocycline had the opposite effect. Quantitative ICC assays confirmed a significant ~1.3-fold increase in iNOS expression by minocycline-treated macrophages, and a substantial 48% reduction in Aβ$^{1-42}$ phagocytosis. Most importantly, GA treatment reduced iNOS production by 28% and increased Aβ phagocytosis 2.5-fold (FIG. 16D-16E). These studies demonstrated that GA induced OPN expression, which led to elongated pro-healing cell morphology, reduced iNOS production, and increased Aβ$^{1-42}$ phagocytosis. Without being bound to any particular theory, these changes may support a switch towards an anti-inflammatory, highly phagocytic macrophage phenotype, which is associated with neuroprotection in AD models.

Next, MMP-9 expression and OPN proteolytic fragments were analyzed. Consistent with the inventors previous results, GA treatment significantly increased MMP-9 expression 2.7-fold in macrophages (FIG. 16F-16G). OPN is a known substrate for MMPs (including MMP-9). A detailed analysis of OPN expression in macrophages was performed using a polyclonal antibody recognizing full-length OPN and its MMP-cleaved fragments, including the 32 kD form. The Western blot analysis and subsequent quantification of band densities revealed that all OPN forms, including fragments derived from MMP proteolysis, were elevated by GA treatment (FIG. 16I-16J) in concurrence with elevated MMP-9 production. Remarkably, the MMP-generated 32 kD C-terminus-containing peptide was elevated 12-fold after GA treatment. The basal levels of this fragment were very low in untreated macrophages, but became very prominent after GA activation (FIG. 16I-16J).

Finally, analysis of MMP-9 and OPN expression in ADtg mouse brains indicated a positive correlation between cerebral OPN immunoreactive area and MMP-9 protein levels (FIG. 19C). OPN expression within cerebral infiltrating CD45$^{hi}$ macrophages showed a stronger correlation with MMP-9 levels (FIG. 19D). Without being bound to any particular theory, the combined data suggest that GA induced OPN expression, including its MMP-cleaved activated fragments, and mediated polarization of macrophages toward a pro-healing, anti-inflammatory, highly phagocytic phenotype, suggesting its novel role in neuroprotection.

In this study, a novel, immunomodulatory role for OPN in AD, utilizing both in vivo and in vitro models was identified. Furthermore, the FDA-approved drug, GA, was an effective means to upregulate its expression in macrophages. The first major observation was that OPN patterns in ADtg mouse brains were detected in AD-associated regions, the hippocampus and cortex. While OPN was abundantly expressed in inflammatory cells surrounding Aβ lesion sites, non-afflicted brain regions mostly exhibited this cytokine in neurons. Among inflammatory cells, OPN was predominantly expressed by infiltrating Iba1$^+$ CD45$^{high}$ or GFP-labeled monocyte-derived macrophages. A possible immunomodulatory role for this cytokine in AD emerges from the findings that OPN correlates tightly with monocyte infiltration and Aβ plaque clearance. Increased OPN expression in brain regions rich in infiltrating Mo/MΦ (i.e. entorhinal cortex) directly involved in Aβ uptake further supports the notion that OPN contributes to macrophage-mediated clearance of Aβ.

Although increased OPN expression was reported in reactive microglia after traumatic brain injury), here it is observed that OPN expression in the ADtg mouse brain selectively occurred in macrophages. This observation is consistent with studies demonstrating that peripheral macrophages phagocytose Aβ plaques much more efficiently than resident microglia. OPN's known interactions with various surface integrins and scavenger receptors further support its direct effects on the phagocytic activity of these inflammatory cells.

It is also noted that the marked upregulation of cerebral OPN following GA immunization was even greater when combined with intravenous monocyte enrichment. These results paralleled the inventors previously reported pattern of increased monocyte recruitment to the brain, brought on synergistically by the same combined immunomodulatory approaches. Given that OPN is an integrin-binding protein expressed by macrophages, these findings could explain its action in opsonization and recruitment of immune cells to inflammatory sites. Therefore, without being bound to any particular theory, it may be concluded that when GA induces recruitment of peripheral phagocytic cell to amyloid plaques, this immunomodulatory phenomenon is mediated by OPN.

Furthermore, this study indicates that GA substantially induces OPN expression in BM-derived macrophages in a manner similar to that observed in brains of ADtg mice. The inventors demonstrate consistent evidence for increased OPN and subsequent intracellular uptake of pre-formed fibrillar Aβ$^{1-42}$ by these GA-stimulated primary cultures. By utilizing systems that negatively regulated OPN expression (siRNA or minocycline) or positively induced it (GA) OPN's crucial role in macrophage-mediated Aβ phagocytosis was demonstrated. These results, along with literature describing OPN's involvement in other phagocytic activities, reveal that fibrillar Aβ$^{1-42}$ phagocytosis may directly depend on OPN expression.

Different functions of OPN may be achieved through its complex proteolytic processing, such as cleavage by MMPs that permits diverse cellular interactions. Specifically, MMP-9 has been implicated in generating functional, more neuroprotective forms of OPN. The data indicate that GA not only induced MMP-9 expression, but also significantly increased the abundance of full-length OPN and its MMP-cleaved fragments. In particular, GA-activated macrophage cultures exhibit a profound 12-fold increase in levels of the 32 kD OPN fragment, a product of OPN implicated in neuroprotection. The examination of infiltrating Mo/MΦ in ADtg mouse brains also offered further support for the connection between MMP-9 and OPN evidenced by their tight correlation and increased expression following GA immunization. These findings agree with previous reports, which indicate MMP-9's role in generating functional forms of OPN. Future studies should ascertain how each OPN fragment may impact macrophage phenotype in the context of AD, without being bound to any particular theory, it can be postulated that GA's induction of a therapeutic macrophage phenotype was mediated by elevating these MMP-cleaved neuroprotective fragments.

Although generally regarded as a pro-inflammatory cytokine, recent studies have shown that OPN may contribute to repair-promoting processes in the brain. This study unexpectedly demonstrated that GA polarizes macrophages towards a highly phagocytic (increased uptake of fibrillar $A\beta_{1-42}$), anti-inflammatory (reduced iNOS and increased MMP-9), pro-healing (elongated) phenotype, which was dependent on OPN expression. Upon OPN inhibition, this phenotype shift was reversed. Without being bound to any particular theory, the data collectively demonstrate a novel role for OPN as a key immune-regulator of macrophage phenotype and Aβ clearance in AD models. Polarization of macrophages by GA was specifically mediated by OPN, suggesting a promising neuroprotective action of OPN in resisting AD-related pathology and promoting tissue repair.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of treating Alzheimer's disease in a subject in need thereof comprising:
   stimulating a population of innate immune cells ex vivo with glatiramer acetate to increase expression of osteopontin;
   detecting the increased expression of osteopontin in said cells; and
   administering to the subject a therapeutically effective amount of the population of innate immune cells that have been stimulated ex vivo with glatiramer acetate.

2. The method of claim 1, wherein the innate immune cells comprise monocytes, macrophages, or combinations thereof.

3. The method of claim 2, wherein the monocytes comprise bone marrow-derived monocytes, spleen-derived monocytes, CD115 positive monocytes ($CD115^+$ monocytes), infiltrating monocytes, or combinations thereof.

4. The method of claim 1, further comprising administering glatiramer acetate to the subject.

5. The method of claim 1, wherein the administering comprises adoptive cell transfer, bone marrow transplantation, or direct delivery to the subject.

6. The method of claim 1, wherein the treating of Alzheimer's disease comprises alleviating a symptom of Alzheimer's disease selected from the group consisting of memory loss, decline in non-memory aspects of cognition, impaired reasoning or judgment, behavior changes, impaired ability to carry out multistep tasks, hallucinations, delusions, paranoia and combinations thereof.

7. The method of claim 1, wherein the administering results in an increase in MMP-9 in the subject, as measured by an immunoassay.

8. The method of claim 7, wherein the administering results in decreased levels of a misfolded protein in the subject, as measured by an immunoassay.

9. The method of claim 8, wherein the misfolded protein is amyloid beta (Aβ).

10. The method of claim 9, wherein the Aβ is $A\beta_{40}$ and/or $A\beta_{42}$.

11. The method of claim 7, wherein treating Alzheimer's disease comprises enhancing clearance of pathological amyloid-β forms, as measured by an immunoassay.

12. The method of claim 7, wherein treating Alzheimer's disease comprises rescuing synaptic structure, as measured by an immunoassay or microscope analysis.

13. A method of improving cognitive function in a subject in need thereof, comprising:

stimulating a population of innate immune cells ex vivo with glatiramer acetate to increase expression of osteopontin;

detecting the increased expression of osteopontin in said cells; and administering to the subject a therapeutically effective amount of a composition comprising a the population of innate immune cells that have been stimulated ex vivo with glatiramer acetate.

14. The method of claim 13, wherein the innate immune cells comprise monocytes, macrophages, or combinations thereof.

15. The method of claim 14, wherein the monocytes comprise bone marrow-derived monocytes, spleen-derived monocytes, CD115 positive monocytes (C115+ monocytes), infiltrating monocytes, or combinations thereof.

16. The method of claim 13, wherein the innate immune cells are phagocytic.

17. The method of claim 13, further comprising administering glatiramer acetate to the subject.

18. The method of claim 13, wherein the administering comprises adoptive cell transfer, bone marrow transplantation, or direct delivery to the subject.

19. The method of claim 13, wherein the administering results in an increase in MMP-9 in the subject, as measured by an immunoassay.

20. The method of claim 13, wherein the administering results in decreased levels of a misfolded protein in the subject, decreased inflammation in the subject, increased synaptic regeneration in the subject, recruitment of macrophages to an amyloid beta (Aβ) plaque site in the subject, or combinations thereof, as measured by an immunoassay or microscope analysis.

21. The method of claim 20, wherein the misfolded protein is Aβ.

22. The method of claim 21, wherein the Aβ is $A\beta_{40}$ and/or $A\beta_{42}$.

* * * * *